US005834189A

United States Patent [19]
Stevens et al.

[11] Patent Number: 5,834,189
[45] Date of Patent: Nov. 10, 1998

[54] METHOD FOR EVALUATION OF POLYMORPHIC GENETIC SEQUENCES, AND THE USE THEREOF IN IDENTIFICATION OF HLA TYPES

[75] Inventors: John K. Stevens, Toronto; James M. Dunn, Scarborough; James Leushner, North York; Ronald J. Green, Toronto, all of Canada

[73] Assignee: Visible Genetics Inc., Toronto, Canada

[21] Appl. No.: 577,858

[22] Filed: Dec. 22, 1995

Related U.S. Application Data

[63] Continuation-in-part of Ser. No. 271,946, Jul. 8, 1994, Pat. No. 5,545,527, which is a continuation-in-part of PCT/US95/08606 Jul. 7, 1995 and Ser. No. 497,202, Jun. 30, 1995.

[51] Int. Cl.$^6$ .............................. C12Q 1/68; C12P 19/34
[52] U.S. Cl. ......................... 435/6; 435/91.1; 435/91.2
[58] Field of Search ........................ 435/6, 7.2, 91.2, 435/91.1; 536/23.1, 24.3, 24.33, 182.8

[56] References Cited

U.S. PATENT DOCUMENTS

| | | | |
|---|---|---|---|
| 4,582,788 | 4/1986 | Erlich | 435/6 |
| 4,811,218 | 3/1989 | Hunkapiller et al. | 364/413.01 |
| 4,865,968 | 9/1989 | Orgel et al. | 435/6 |
| 4,971,903 | 11/1990 | Hyman | 435/6 |
| 5,119,316 | 6/1992 | Dam et al. | 364/498 |
| 5,122,345 | 6/1992 | Tabor et al. | 422/116 |
| 5,124,247 | 6/1992 | Ansorge | |
| 5,171,534 | 12/1992 | Smith et al. | 422/82.05 |
| 5,207,880 | 5/1993 | Middendorf et al. | 204/182.8 |
| 5,365,455 | 11/1994 | Tibbets et al. | 364/497 |
| 5,424,184 | 6/1995 | Santamaria et al. | 435/6 |
| 5,451,512 | 9/1995 | Apple et al. | 435/91.2 |

FOREIGN PATENT DOCUMENTS

| | | |
|---|---|---|
| 0592060 | 9/1993 | European Pat. Off. |
| 92/10587 | 6/1992 | WIPO . |
| 9215711 | 9/1992 | WIPO . |
| 92/19771 | 11/1992 | WIPO . |

OTHER PUBLICATIONS

Langemeier et al. BioTechniques 17: 484–490, 1990.
Santamaria et al. Human Immunology 37:39–50, 1993.
Bodmer et al. Human Immunology 41:1–20, 1994.
Sarkar et al., "Dideoxy Fingerprinting (ddF): A Rapid and Efficient Screen for the Presence of Mutations" *Genomics* 13:441–443 (1992).
Lin et al., "Characterization of Genetic Defects of Hemophilia A in Patients of Chinese Origin" *Genomics* 18: 496–504 (1993).
Langemeir et al, "Application of Cycle Dideoxy Fingerprinting to Screening Heterogenous Populations of the Equine Infectious Anemia Virus", *BioTechniques* 17: 484–490 (1994).
Krishnamani et al., "Detection of a Novel Arginine Vasopressin Defect by Dideoxy Fingerprinting" *J. Clin. Endocrinol. & Metabol.* 77: 596–598 (1993).

Ellison et al., "Detection of Mutations and Polymorphisms Using Fluorescence–Based Dideoxy Fingerprinting (F–ddF)", *BioTechniques* 17: 742–753 (1994).
Bodmer et al., "Nomenclature for Factors of the HLA System" Human Immunology 1994 41: 1–20.
Bowling et al., "Neighboring nucleotide interactions during DNA sequencing gel electrophoresis" Nucleic Acids Research 1991, vol. 19 No. 11 3809–3097.
Cereb et al., "Locus–specific amplification of HLA class I genes from genomic DNA: locus–specific sequences in the first and third introns of HLA-A, -B and -C alleles" Locus–specific amplification of HLA class I genes 1995, 1–11.
Erickson, "Diagnosis by DNA," Scientific American 1992 p. 116.
Giddings et al., "An adaptive, object oriented strategy for base calling in DNA sequence analysis," Nucleic Acids Research 1993, vol. 21 No. 19 4530–4540.
Maxam et al., "A new method for sequencing DNA" Proc. Natl. Acad. Sci. USA, 1977 vol. 74, No. 2 560–564.
Runnebaum et al., "Mutations in p53 as potential molecular markers for human breast cancer," Proc. Natl. Acad. Sci. 1991 USA vol. 88 10657–10661.
Sanger et al., "NA sequencing with chain–terminating inhibitors" Proc. Natl. Acad. Sci. 1977 USA vol. 74, No. 12 5463–5467.
Santamaria et al., "HLA Class I Sequence–Based Typing" Human Immunology 1993 37, 39–50.
Summers et al., "HLA Class I Non–Coding Nucleotide Sequences" European Jour. of Immunogenetics 1993 20, 201–240.
Tibbetts et al., "Neural Networks for Automated Basecalling of Gel–based DNA Sequencing Ladders" Chapter Thirty–One 219–229.

(List continued on next page.)

*Primary Examiner*—Kenneth R. Horlick
*Attorney, Agent, or Firm*—Oppedahl & Larson

[57] ABSTRACT

The allelic type of a polymorphic genetic locus in a sample is identified by first combining the sample with a sequencing reaction mixture containing a polymerase, nucleotide feedstocks, one type of chain terminating nucleotide and a sequencing primer to form a plurality of oligonucleotide fragments of differing lengths, and then evaluating the length of the oligonucleotide fragments. As in a standard sequencing procedure, the lengths of the fragments indicate the positions of the type of base corresponding to the chain terminating nucleotide in the extended primer. Instead of performing and evaluating four concurrent reactions, one for each type of chain terminating nucleotide, however, the sample is concurrently combined with at most three, and preferably only one, sequencing reaction mixtures containing different types of chain terminating nucleotides. The information obtained from this test is evaluated prior to performing any additional tests on the sample. In many cases, evaluation of the positions of only a single base using one sequencing reaction will allow for allelic typing of the sample.

26 Claims, 7 Drawing Sheets

OTHER PUBLICATIONS

Warren et al., "Comparative Evaluation of Detection Assays for Chlamydia trachomatis" Jour. of Clinical Microbiology vol. 31 No. 6 1993, 1663–1666.

Johnston–Dow, et al. "A General Approach for Sequencing Based Typing of HLA–A" Poster Presentation, 1995 ASHI Meeting, Dallas, TX.

Weiss et al., "Organization, Sequence and expression of the HLA–B27 Gene: Moelcular Approach to Analyze HLA and Disease Associations" *Immunobiol.* 170: 367–380 (1985).

Blasczyk et al., "The Diversity of the HLA Class I Introns Reflects the Ancestral Relationships of the Coding Regions", Abstracts of the $22^{nd}$ Annual Meeting if The American Society of Histocompatability and Immunogenetics, No. 2.4–26 (1996).

"HLA Class I SSP ARMS–PCR Typing Kit", Reference Manual (1995).

Petersdorf et al., "A comprehensive approach for typing the alleles of the HLA–B locus by automated sequencing" *Tissue Antigens* 46: 73–85 (1995).

```
GENE XYZ1     nt      100      101      102

A        A        A       ALLELE 1

A        T        A       ALLELE 2
             ─────────────────────────────────────────
                       A        C        A       ALLELE 3
```

FIG. 1

```
OBSERVED DATA
4 nts              G   C   A  (t/a)   T  (g/c)   A

ALLELE 12          G   C   A  (T  )   T  (G  )   A
ALLELE 13          G   C   A  (A  )   T  (C  )   A

ALLELE 14          G   C   A  (T  )   T  (C  )   A
ALLELE 15          G   C   A  (A  )   T  (G  )   A
```

IMPOSSIBLE TO DISTINGUISH HETEROZYGOTE PAIR BY DNA SEQUENCING ALONE

FIG. 3

```
CONTROL
LANE (4nt)  | | | | | | | | | | | | | | | | | | | | |  ⎤
                                                       ⎥ AUTO-
A LANE                                                 ⎬ RADIOGRAPH
SEQUENCE                                               ⎥ RESULTS
(SAMPLE)    |   | |   |     | | |     |              ⎦

TEXT
FILE FOR
RESULTS     A — — A A — — — A — — — A A A — — — A — —
```

FIG. 4

FIG. 2A
- OBSERVED DATA  A - - - A - - A - A
- ALLELE 1       - - - - A - - A - -
- ALLELE 2       A - - - - - - A - A

FIG. 2B
- OBSERVED DATA  - - A - - - A A - A
- ALLELE 3       - A A A - - A - - -  ⎤ ELIMINATED
- ALLELE 4       - - - - A - - A - -  ⎦
- ALLELE 5       - - A - - - - - - A  ⎤
- ALLELE 6       - - - - - - A A - -  ⎥ POSSIBLE
- ALLELE 7       - - A - - - - A - -  ⎦

FIG. 2C
- OBSERVED DATA ONE nt ONLY   - - A - - - A A - A
- ALLELE 8       - - A - - - - - - A  ⎤
- ALLELE 9       - - - - - - A A - -  ⎥ UNCLEAR WHICH ALLELIC PAIR
- ALLELE 10      - - A - - - - A - -  ⎥ IS CORRECT
- ALLELE 11      - - - - - - A - - A  ⎦

- OBSERVED DATA TWO nt ONLY   - - A - T - A A - A
- ALLELE 8       - - A - - - - - T A  ⎤ INCORRECT
- ALLELE 9       - - - - - - A A - -  ⎦
- ALLELE 10      - - A - T - - A - -  ⎤ CORRECT
- ALLELE 11      - - - - - - A - - A  ⎦

FIG. 2D
- OBSERVED DATA  - A - A A -         POSSIBILITIES:
- ALLELE A       - A - A A -  HOMOZYGOTE
- ALLELE B       - A  - A -                    HETEROZYGOTE
- ALLELE C       - - - A - -                   HETEROZYGOTE

ABSENCE OF PEAK IDENTIFIED BY COMPARISON OF AREAS UNDER THE CURVE FOR EACH PEAK

POSSIBLE T TERMINATION REACTION RESULTS

```
         256 7 8 9 0 1 2 3 4 5 6 7 8 9 0 1 2 3 4 5 6 7 8 9 280
GROUP 1
B        - - - - - - - - T - - - - - T - - T - - - - - - - -
Ba       - - - - - - - - T - - - - - T - - T - - - - - - - -
D        - - - - - - - - T - - - - - T - - T - - - - - - - -
E        - - - - - - - - T - - - - - T - - T - - - - - - - -
L1       - - - - - - - - T - - - - - T - - T - - - - - - - -
L2       - - - - - - - - T - - - - - T - - T - - - - - - - -

GROUP 2
F        - - - - - T T T - - - - - - - - - T T - T - - - -
G        - - - - - T T T - - - - - - - - - T T - T - - - -

GROUP 3
C        - - - - - - - - T - - T - - - - - - - - T - T - -
A        - - - - - - - T - - T - - - - - - - - - T - T - -
H        - - - - - - - T - - T - - - - - - - - - T - T - -
I        - - - - - - - T - - T - - - - - - - - - T - T - -
J        - - - - - - - T - - T - - - - - - - - - T - T - -
K        - - - - - - - T - - T - - - - - - - - - T - T - -
L3       - - - - - - - T - - T - - - - - - - - - T - T - -

OBSERVED RESULTS
SAMPLE 1 - - - - - - - T - - T - - T - - T - - - T - T - -
SAMPLE 2 - - - - - - T - - - - - T - - T - - - - - - - - -
```

POSSIBLE C TERMINATION REACTION RESULTS

```
       256 7 8 9 0 1 2 3 4 5 6 7 8 9 0 1 2 3 4 5 6 7 8 9 280
B      - C C - - - C C - - C - - C - - C - - C - - - C -
Ba     - C C - - - C C - - C - - C - - C - - C - - - C -
D      - C C - - - C C - - C - - C - - - - - - C - - - C -
E      - C C - - - C C - - C - - - - - - C - - C - - - C -
L1     - C C - - - C C - - C - - C - - C - - C - - - C -
L2     - C C - - - C C - - C - - C - - C - - C - - - C -

F      - - - - - C - - - - - C C - - - - C - - C - - - - -
G      - - - - - C - - - - - C C - - - - C - - C - - - - -

C      - C - - C - C C - - C - - C C - - C - - - - - - - C
A      - C - - C - C C - - C - - C C - - C - - - - - - - C
H      - C - - C - C C - - C - - C C - - C - - - C - - C
I      - C - - C - C C - - C - - C C - - - - - - - - - - C
J      - C - - C - C C - - C - - C C - - C - - - - - - - C
K      - C - - C - C C - - C - - C C - - C - - - - - - - -
L3     - C C - - - C C - - C - - C C - - C - - - C - - C
```

POSSIBLE G TERMINATION REACTION RESULTS

SEQUENCE LISTING ( 1 ) GENERAL INFORMATION:

( i i i ) NUMBER OF SEQUENCES: 33

( 2 ) INFORMATION FOR SEQ ID NO: 1:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR1 alleles of HLA Class II genes ( x i ) SEQUENCE DESCRIPTION: SEQ ID NO:1:

TTGTGGCAGC TTAAGTTTGA AT        22

( 2 ) INFORMATION FOR SEQ ID NO: 2:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR1 alleles of HLA Class II genes ( x i ) SEQUENCE DESCRIPTION: SEQ ID NO:2:

CCGCCTCTGC TCCAGGAG        18

( 2 ) INFORMATION FOR SEQ ID NO: 3:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal -continued (vi) ORIGINAL SOURCE:
        (A) ORGANISM: human (ix) FEATURE:
        (D) OTHER INFORMATION: amplification primer for DR1 alleles of HLA Class II genes (xi) SEQUENCE DESCRIPTION: SEQ ID NO:3:

CCCGCTCGTC TTCCAGGAT            19

(2) INFORMATION FOR SEQ ID NO: 4:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for DR2 alleles of HLA Class II genes (xi) SEQUENCE DESCRIPTION: SEQ ID NO:4:

TCCTGTGGCA GCCTAAGAG            19

(2) INFORMATION FOR SEQ ID NO: 5:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for DR2 alleles of HLA Class II genes (xi) SEQUENCE DESCRIPTION: SEQ ID NO:5:

CCGCGCCTGC TCCAGGAT            18

(2) INFORMATION FOR SEQ ID NO: 6:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( D ) OTHER INFORMATION: amplification primer for DR2 alleles of
    HLA Class II genes ( x i ) SEQUENCE DESCRIPTION: SEQ ID NO:6:

AGGTGTCCAC CGCGCGGCG  19

( 2 ) INFORMATION FOR SEQ ID NO: 7:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR3, 8, 11,
        12, 13, 14 alleles of HLA Class II genes ( x i ) SEQUENCE DESCRIPTION: SEQ ID NO:7:

CACGTTTCTT GGAGTACTCT AC  22

( 2 ) INFORMATION FOR SEQ ID NO: 8:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR3, 8, 11,
        12, 13, 14 alleles of HLA Class II genes ( x i ) SEQUENCE DESCRIPTION: SEQ ID NO:8:

CCGCTGCACT GTGAAGCTCT  20

( 2 ) INFORMATION FOR SEQ ID NO: 9:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear (i i) MOLECULE TYPE: other nucleic acid (i i i) HYPOTHETICAL:no (i v) ANTI-SENSE: yes (v) FRAGMENT TYPE: internal (v i) ORIGINAL SOURCE:
    (A) ORGANISM: human (i x) FEATURE:
    (D) OTHER INFORMATION: amplification primer for DR4 alleles of HLA Class II genes (x i) SEQUENCE DESCRIPTION: SEQ ID NO:9:

GTTTCTTGGA GCAGGTTAAA CA    22

(2) INFORMATION FOR SEQ ID NO: 10:

(i) SEQUENCE CHARACTERISTICS:
    (A) LENGTH: 20
    (B) TYPE: nucleic acid
    (C) STRANDEDNESS: double
    (D) TOPOLOGY: linear (i i) MOLECULE TYPE: other nucleic acid (i i i) HYPOTHETICAL:no (i v) ANTI-SENSE: no (v) FRAGMENT TYPE: internal (v i) ORIGINAL SOURCE:
    (A) ORGANISM: human (i x) FEATURE:
    (D) OTHER INFORMATION: amplification primer for DR4 alleles of HLA Class II genes (x i) SEQUENCE DESCRIPTION: SEQ ID NO:10:

CTGCACTGTG AAGCTCTCAC    20

(2) INFORMATION FOR SEQ ID NO: 11:

(i) SEQUENCE CHARACTERISTICS:
    (A) LENGTH: 20
    (B) TYPE: nucleic acid
    (C) STRANDEDNESS: double
    (D) TOPOLOGY: linear (i i) MOLECULE TYPE: other nucleic acid (i i i) HYPOTHETICAL:no (i v) ANTI-SENSE: no (v) FRAGMENT TYPE: internal (v i) ORIGINAL SOURCE:
    (A) ORGANISM: human (i x) FEATURE:
    (D) OTHER INFORMATION: amplification primer for DR4 alleles of HLA Class II genes (x i) SEQUENCE DESCRIPTION: SEQ ID NO:11:

CTGCACTGTG AAGCTCTCCA    20

(2) INFORMATION FOR SEQ ID NO: 12:

(i) SEQUENCE CHARACTERISTICS:
    (A) LENGTH: 20

(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
(A) ORGANISM: human (ix) FEATURE:
(D) OTHER INFORMATION: amplification primer for DR7 alleles of HLA Class II genes (xi) SEQUENCE DESCRIPTION: SEQ ID NO:12:

CCTGTGGCAG GGTAAGTATA 20

(2) INFORMATION FOR SEQ ID NO: 13:

(i) SEQUENCE CHARACTERISTICS:
(A) LENGTH: 21
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
(A) ORGANISM: human (ix) FEATURE:
(D) OTHER INFORMATION: amplification primer for DR7 alleles of HLA Class II genes (xi) SEQUENCE DESCRIPTION: SEQ ID NO:13:

CCCGTAGTTG TGTCTGCACA C 21

(2) INFORMATION FOR SEQ ID NO: 14:

(i) SEQUENCE CHARACTERISTICS:
(A) LENGTH: 23
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
(A) ORGANISM: human (ix) FEATURE:
(D) OTHER INFORMATION: amplification primer for DR9 alleles of HLA Class II genes (xi) SEQUENCE DESCRIPTION: SEQ ID NO:14:

GTTTCTTGAA GCAGGATAAG TTT 23

( 2 ) INFORMATION FOR SEQ ID NO: 15:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR9 alleles of
            HLA Class II genes ( x i ) SEQUENCE DESCRIPTION: SEQ ID NO:15:

CCCGTAGTTG TGTCTGCACA C                                                      21

( 2 ) INFORMATION FOR SEQ ID NO: 16:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR10 alleles
            of HLA Class II genes ( x i ) SEQUENCE DESCRIPTION: SEQ ID NO:16:

CGGTTGCTGG AAAGACGCG                                                        19

( 2 ) INFORMATION FOR SEQ ID NO: 17:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR10 alleles
            of HLA Class II genes ( x i ) SEQUENCE DESCRIPTION: SEQ ID NO:17:

CTGCACTGTG AAGCTCTCAC 20

( 2 ) INFORMATION FOR SEQ ID NO: 18:

( i ) SEQUENCE CHARACTERISTICS:
          ( A ) LENGTH: 17
          ( B ) TYPE: nucleic acid
          ( C ) STRANDEDNESS: double
          ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
          ( A ) ORGANISM: human ( i x ) FEATURE:
          ( D ) OTHER INFORMATION: sequencing primer for DR alleles of HLA
              Class II genes ( x i ) SEQUENCE DESCRIPTION: SEQ ID NO:18:

GAGTGTCATT TCTTCAA 17

( 2 ) INFORMATION FOR SEQ ID NO: 19:

( i ) SEQUENCE CHARACTERISTICS:
          ( A ) LENGTH: 20
          ( B ) TYPE: nucleic acid
          ( C ) STRANDEDNESS: double
          ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
          ( A ) ORGANISM: human ( i x ) FEATURE:
          ( D ) OTHER INFORMATION: amplification primer for HLA-C gene,
              exon 2

( x i ) SEQUENCE DESCRIPTION: SEQ ID NO:19:

AGCGAGTGCC CGCCCGGCGA 20

( 2 ) INFORMATION FOR SEQ ID NO: 20:

( i ) SEQUENCE CHARACTERISTICS:
          ( A ) LENGTH: 25
          ( B ) TYPE: nucleic acid
          ( C ) STRANDEDNESS: double
          ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
          ( A ) ORGANISM: human ( i x ) FEATURE:

( D ) OTHER INFORMATION: amplification primer for HLA-C gene,
                  exon 2

( x i ) SEQUENCE DESCRIPTION: SEQ ID NO:20:

ACCTGGCCCG TCCGTGGGGG ATGAG                                                              2 5

( 2 ) INFORMATION FOR SEQ ID NO: 21:

( i ) SEQUENCE CHARACTERISTICS:
            ( A ) LENGTH: 22
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
            ( A ) ORGANISM: human ( i x ) FEATURE:
            ( D ) OTHER INFORMATION: amplification primer for HLA-C gene,
                  exon 3

( x i ) SEQUENCE DESCRIPTION: SEQ ID NO:21:

GACCGCGGGG CCGGGGCCAG GG                                                                 2 2

( 2 ) INFORMATION FOR SEQ ID NO: 22:

( i ) SEQUENCE CHARACTERISTICS:
            ( A ) LENGTH: 23
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
            ( A ) ORGANISM: human ( i x ) FEATURE:
            ( D ) OTHER INFORMATION: amplification primer for HLA-C gene,
                  exon 3

( x i ) SEQUENCE DESCRIPTION: SEQ ID NO:22:

GGAGATGGGG AAGGCTCCCC ACT                                                                2 3

( 2 ) INFORMATION FOR SEQ ID NO: 23:

( i ) SEQUENCE CHARACTERISTICS:
            ( A ) LENGTH: 18
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: human ( i x ) FEATURE:
        ( D ) OTHER INFORMATION: forward sequencing primer for HLA-C
              gene, exon 2

( x i ) SEQUENCE DESCRIPTION: SEQ ID NO:23:

CCGGGGCGCA GGTCACGA                                                              18

( 2 ) INFORMATION FOR SEQ ID NO: 24:

( i ) SEQUENCE CHARACTERISTICS:
            ( A ) LENGTH: 18
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
            ( A ) ORGANISM: human ( i x ) FEATURE:
            ( D ) OTHER INFORMATION: reverse sequencing primer for HLA-C
                  gene, exon 2

( x i ) SEQUENCE DESCRIPTION: SEQ ID NO:24:

GGAGGGTCGG GCGGGTCT                                                              18

( 2 ) INFORMATION FOR SEQ ID NO: 25:

( i ) SEQUENCE CHARACTERISTICS:
            ( A ) LENGTH: 18
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
            ( A ) ORGANISM: human ( i x ) FEATURE:
            ( D ) OTHER INFORMATION: reverse sequencing primer for HLA-C
                  gene, exon 3

( x i ) SEQUENCE DESCRIPTION: SEQ ID NO:25:

CGGGACGTCG CAGAGGAA                                                              18

( 2 ) INFORMATION FOR SEQ ID NO: 26:

( i ) SEQUENCE CHARACTERISTICS:
            ( A ) LENGTH: 20
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
          ( A ) ORGANISM: human ( i x ) FEATURE:
          ( D ) OTHER INFORMATION: amplification primer for exon 6 of
              lipoprotein lipase gene ( x i ) SEQUENCE DESCRIPTION: SEQ ID NO:26:

GCCGAGATAC AATCTTGGTG                                                                20

( 2 ) INFORMATION FOR SEQ ID NO: 27:

( i ) SEQUENCE CHARACTERISTICS:
          ( A ) LENGTH: 20
          ( B ) TYPE: nucleic acid
          ( C ) STRANDEDNESS: double
          ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
          ( A ) ORGANISM: human ( i x ) FEATURE:
          ( D ) OTHER INFORMATION: amplification primer for exon 6 of
              lipoprotein lipase gene ( x i ) SEQUENCE DESCRIPTION: SEQ ID NO:27:

CAGGTACATT TTGCTGCTTC                                                               20

( 2 ) INFORMATION FOR SEQ ID NO: 28:

( i ) SEQUENCE CHARACTERISTICS:
          ( A ) LENGTH: 23
          ( B ) TYPE: nucleic acid
          ( C ) STRANDEDNESS: double
          ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
          ( A ) ORGANISM: Chlamydia ( i x ) FEATURE:
          ( D ) OTHER INFORMATION: amplification primer for Chlamydia omp1
              gene ( x i ) SEQUENCE DESCRIPTION: SEQ ID NO:28:

ACCACTTGGT GTGACGCTAT CAG                                                      23

( 2 ) INFORMATION FOR SEQ ID NO: 29:

( i ) SEQUENCE CHARACTERISTICS:
          ( A ) LENGTH: 22
          ( B ) TYPE: nucleic acid
          ( C ) STRANDEDNESS: double
          ( D ) TOPOLOGY: linear (i i) MOLECULE TYPE: other nucleic acid (i i i) HYPOTHETICAL: no (i v) ANTI-SENSE: no (v) FRAGMENT TYPE: internal (v i) ORIGINAL SOURCE:
  (A) ORGANISM: Chlamydia (i x) FEATURE:
  (D) OTHER INFORMATION: amplification primer for Chlamydia omp1

(x i) SEQUENCE DESCRIPTION: SEQ ID NO:29:

CGGAATTGTG CATTTACGTG AG    22

(2) INFORMATION FOR SEQ ID NO: 30:

(i) SEQUENCE CHARACTERISTICS:
  (A) LENGTH: 25
  (B) TYPE: nucleic acid
  (C) STRANDEDNESS: double
  (D) TOPOLOGY: linear (i i) MOLECULE TYPE: other nucleic acid (i i i) HYPOTHETICAL: no (i v) ANTI-SENSE: yes (v) FRAGMENT TYPE: internal (v i) ORIGINAL SOURCE:
  (A) ORGANISM: Chlamydia (i x) FEATURE:
  (D) OTHER INFORMATION: amplification primer for Chlamydia omp1
    gene (x i) SEQUENCE DESCRIPTION: SEQ ID NO:30:

CCGACCGCGT CTTGAAAACA GATGT    25

(2) INFORMATION FOR SEQ ID NO: 31:

(i) SEQUENCE CHARACTERISTICS:
  (A) LENGTH: 21
  (B) TYPE: nucleic acid
  (C) STRANDEDNESS: double
  (D) TOPOLOGY: linear (i i) MOLECULE TYPE: other nucleic acid (i i i) HYPOTHETICAL: no (i v) ANTI-SENSE: no (v) FRAGMENT TYPE: internal (v i) ORIGINAL SOURCE:
  (A) ORGANISM: Chlamydia (i x) FEATURE:
  (D) OTHER INFORMATION: amplification primer for Chlamydia omp1
    gene (x i) SEQUENCE DESCRIPTION: SEQ ID NO:31:

CACCCACATT CCCAGAGAGC T    21

(2) INFORMATION FOR SEQ ID NO: 32:

(i) SEQUENCE CHARACTERISTICS:
  (A) LENGTH: 21
  (B) TYPE: nucleic acid

```
                    ( C ) STRANDEDNESS: double
                    ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( v i ) ORIGINAL SOURCE:
                    ( A ) ORGANISM: Chlamydia ( i x ) FEATURE:
                    ( D ) OTHER INFORMATION: amplification primer for Chlamydia omp1
                          gene ( x i ) SEQUENCE DESCRIPTION: SEQ ID NO:32:

CGTGCAGCTT TGTGGGAATG T                                          2 1

( 2 ) INFORMATION FOR SEQ ID NO: 33:

( i ) SEQUENCE CHARACTERISTICS:
                    ( A ) LENGTH: 24
                    ( B ) TYPE: nucleic acid
                    ( C ) STRANDEDNESS: double
                    ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( v i ) ORIGINAL SOURCE:
                    ( A ) ORGANISM: Chlamydia ( i x ) FEATURE:
                    ( D ) OTHER INFORMATION: amplification primer for Chlamydia omp1
                          gene ( x i ) SEQUENCE DESCRIPTION: SEQ ID NO:33:

CTAGATTTCA TCTTGTTCAA TTGC                                       2 4
```

METHOD FOR EVALUATION OF POLYMORPHIC GENETIC SEQUENCES, AND THE USE THEREOF IN IDENTIFICATION OF HLA TYPES

SPECIFICATION

This application is a continuation-in-part of U.S. patent application Ser. No. 08/271,946 filed Jul. 8, 1994 U.S. Pat. No. 5,545,527, International Patent Application PCT/US95/08606 filed Jul. 7, 1995 and U.S. patent application Ser. No. 08/497,202, filed Jun. 30, 1995 which are incorporated herein by reference.

BACKGROUND OF THE INVENTION

Genetic testing to determine the presence of or a susceptibility to a disease condition offers incredible opportunities for improved medical care, and the potential for such testing increases almost daily as ever increasing numbers of disease-associated genes and/or mutations are identified. A major hurdle which must be overcome to realize this potential, however, is the high cost of testing. This is particularly true in the case of highly polymorphic genes where the need to test for a large number of variations may make the test procedure appear to be so expensive that routine testing can never be achieved.

The hierarchical assay methodology described in U.S. patent application Ser. No. 08/271,946 U.S. Pat. No. 5,545,527 and PCT/US95/08606 provides a mechanism for systematically reducing the cost per test by utilizing a series of different test methodologies which may have significant numbers of results incorrectly indicating the absence of a genetic sequence of interest, but which rarely if ever yield a result incorrectly indicating the presence of such a genetic sequence. The tests employed in the hierarchy may frequently be combinations of different types of molecular tests, for examples combinations of immunoassays, oligonucleotide probe hybridization tests, oligonucleotide fragment analyses, and direct nucleic acid sequencing.

This application relates to a particular type of test which can be useful alone or as part of a hierarchical testing protocol, particularly for highly polymorphic genes. A particular example of the use of this test is its application to determining the allelic type of human HLA genes.

The human HLA genes are part of the major histocompatability complex (MHC), a cluster of genes associated with tissue antigens and immune responses. Within the MHC genes are two groups of genes which are of substantial importance in the success of tissue and organ transplants between individuals. The HLA Class I genes encode transplantation antigens which are used by cytotoxic T cells to distinguish self from non-self. The HLA class II genes, or immune response genes, determine whether an individual can mount a strong response to a particular antigen. Both classes of HLA genes are highly polymorphic, and in fact this polymorphism plays a critical role in the immune response potential of a host. On the other hand, this polymorphism also places an immunological burden on the host transplanted with allogeneic tissues. As a result, careful testing and matching of HLA types between tissue donor and recipient is a major factor in the success of allogeneic tissue and marrow transplants.

Typing of HLA genes has proceeded along two basic lines: serological and nucleic acid-based. In the case of serological typing, antibodies have been developed which are specific for certain types of HLA proteins. Panels of these tests can be performed to evaluate the type of a donor or recipient tissue. In nucleic acid based-approaches, samples of the HLA genes may be hybridized with sequence-specific oligonucleotide probes to identify particular alleles or allele groups. In some cases, determination of HLA type by sequencing of the HLA gene has also been proposed. Santamaria P., et al "HLA Class I Sequence-Based Typing" Human Immunology 37, 39–50 (1993).

In all of these cases, the test panel performed on each individual sample is extensive, with the result that the cost of HLA typing is very high. It would therefore be desirable to have a method for typing HLA which provided comparable or better reliability at substantially reduced cost. It is an object of the present invention to provide such a method.

SUMMARY OF THE INVENTION

The method of the invention makes use of a modification of standard sequencing technology, preferably in combination with improved data analysis capabilities to provide a streamlined method for obtaining information about the allelic type of a sample of genetic material. Thus, in accordance with the invention, the allelic type of a polymorphic genetic locus in a sample is identified by first combining the sample with a sequencing reaction mixture containing a template-dependent nucleic acid polymerase, A, T, G and C nucleotide feedstocks, one type of chain terminating nucleotide and a sequencing primer under conditions suitable for template dependant primer extension to form a plurality of oligonucleotide fragments of differing lengths, and then evaluating the length of the oligonucleotide fragments. As in a standard sequencing procedure, the lengths of the fragments indicate the positions of the type of base corresponding to the chain terminating nucleotide in the extended primer. The method of the invention differs from standard sequencing procedures, however, because instead of performing and evaluating four concurrent reactions, one for each type of chain terminating nucleotide, in the method of the invention the sample is concurrently combined with at most three sequencing reaction mixtures containing different types of chain terminating nucleotides. Preferably, the sample will be combined with only one reaction mixture, containing only one type of chain terminating nucleotide and the information obtained from this test will be evaluated prior to performing any additional tests on the sample.

In many cases, evaluation of the positions of only a single base will allow for allelic typing of the sample. In this case, no further tests need to be performed. Thus, the use of the method of the invention can increase laboratory throughput (since up to four times as many samples can be processed on the same amount of equipment) and reduce the cost per test by up to a factor of four compared to sequencing of all four bases for every sample.

BRIEF DESCRIPTION OF THE DRAWINGS

FIG. 1 shows the application of the invention to typing of a simple polymorphic gene;

FIGS. 2a–2d illustrates an improved method for distinguishing heterozygotic alleles using the present invention;

FIG. 3 illustrates a situation in which heterozygote pairs remain ambiguous even after full sequencing;

FIG. 4 illustrates the use of a control lane to evaluate the number of intervening bases in a single base sequencing reaction;

FIGS. 8A–8C illustrate the application of the invention to typing of *Chlamydia trachomatis*.

DETAILED DESCRIPTION OF THE INVENTION

Figure 5:
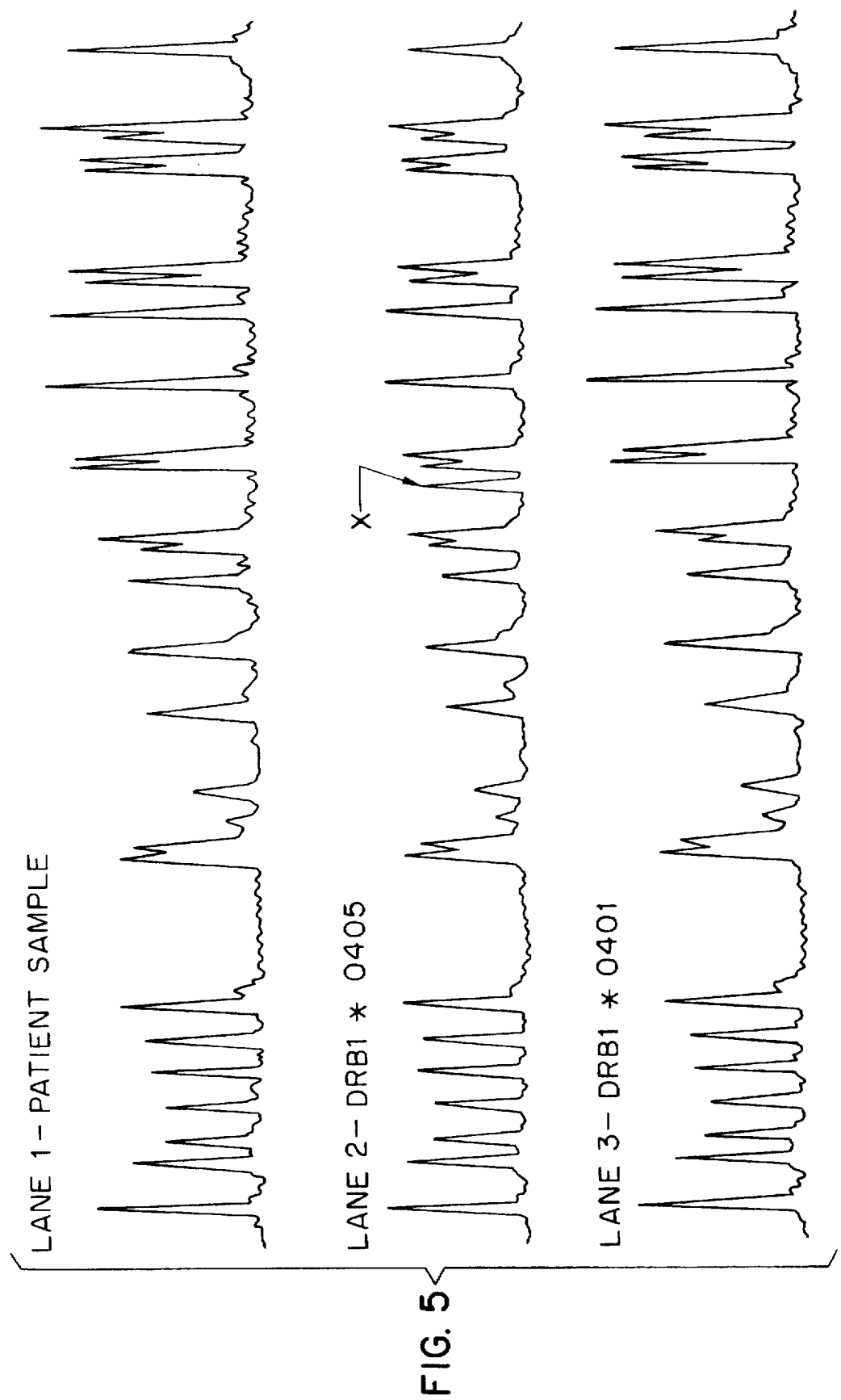
FIG. 5 shows results from an automated DNA sequencing apparatus.

While the terminology used in this application is standard within the art, the following definitions of certain terms are provided to assure clarity.

1. "Allele" refers to a specific version of a nucleotide sequence at a polymorphic genetic locus.
2. "Polymorphism" means the variability found within a population at a genetic locus.
3. "Polymorphic site" means a given nucleotide location in a genetic locus which is variable within a population.
4. "Gene" or "Genetic locus" means a specific nucleotide sequence within a given genome.
5. The "location" or "position" of a nucleotide in a genetic locus means the number assigned to the nucleotide in the gene, generally taken from the CDNA sequence or the genomic sequence of the gene.
6. The nucleotides Adenine, Cytosine, Guanine and Thymine are sometimes represented by their designations of A, C, G or T, respectively.

While it has long been apparent to persons skilled in the art that knowledge of the identity of the base at a particular location within a polymorphic genetic locus may be sufficient to determine the allelic type of that locus, this knowledge has not led to any modification of sequencing procedures. Rather, the knowledge has driven development of techniques such as allele-specific hybridization assays, and allele-specific ligation assays. Despite the failure of the art to recognize the possibility, however, it is not always necessary to determine the sequence of all four nucleotides of a polymorphic genetic locus in order to determine which allele is present in a specific patient sample. Certain alleles of a genetic locus may be distinguishable on the basis of identification of the location of less than four, and often only one nucleotide. This finding allows the development of the present method for improved allele identification at a polymorphic genetic locus.

A simple example is to consider a polymorphic site for which only two alleles are known, as in FIG. 1. In this case, identification of the location of the A nucleotides in the genetic locus, particularly at site numbered 101, will distinguish whether allele 1 or allele 2 is present. If a third allele was discovered which had a C at site 101, the presence of the allele could be distinguished either by the absence at site 101 of an A and a T in independent A and T reactions or by the presence of a C at site 101.

Traditionally, if sequencing were going to be used to evaluate the allelic type of the polymorphic site of FIG. 1, four dideoxy nucleotide "sequencing" reactions of the type described by Sanger et al. (Proc. Natl. Acad. Sci. USA 74: 5463–5467 (1977)) would be run on the sample concurrently, and the products of the four reactions would then be analyzed by polyacrylamide gel electrophoresis. (see Chp 7.6, Current Protocols in Molecular Biology, Eds. Ausubel, F. M. et al, (John Wiley & Sons; 1995)) In this well known technique, the each of the four sequencing reactions generates a plurality of primer extension products, all of which end with a specific type of dideoxy-nucleotide. Each lane on the electrophoresis thus reflects the positions of one type of base in the extension product, but does not reveal the order and type of nucleotides intervening between the bases of this specific type. The information provided by the four lanes is therefore combined in known sequencing procedures to arrive at a composite picture of the sequence as a whole.

In accordance with the present invention, however, single sequencing reactions are performed and evaluated independently to provide the number of intervening bases between each instance of a selected base and thus a precise indication of the positional location of the selected base. Applying the method of the invention to the simplistic example of FIG. 1, a single sequencing reaction would first be performed using either dideoxy-A or dideoxy-T as the chain terminating nucleotide. If the third allelic type did not exist or was unknown, this single test would be enough to provide a specific result. If the third allelic type was known to exist, a second sequencing test could be performed using either dideoxy-C or the dideoxy-A/T not used in the first test to resolve. Alternatively, some other test such as an allele-specific hybridization probe or an antibody test which distinguished well between allele 2 and allele 3 could be used in this case.

As is clear from this example, the method of the invention specifically identifies "known" alleles of a polymorphic locus, and is not necessarily useful for identification of new and hitherto unrecorded alleles. An unknown allele might be missed if it were incorrectly assumed that the single nucleotide sequence obtained from a patient sample corresponded to a unique allele, when in fact other nucleotides of the allele had been rearranged in a new fashion. The method is specific for distinguishing among known alleles of a polymorphic locus (though it may fortuitously come across new mutations if the right single nucleotide sequence is chosen). Databases listing known alleles must therefore be continually updated to provide greatest utility for the invention.

The advantages of "less than 4" nucleotide analysis of the invention for identifying alleles are the decrease in costs for reagents and labor and the increased throughput of patient samples that can be obtained in a diagnostic laboratory. These advantages can be more dramatically demonstrated by considering a system which more closely approximates a real world example. For this purpose, we have assumed a population in which only the known HLA Class II DR4 alleles exist (of these, 5 alleles DRB1*0401, DRB1*0402, DRB1*0405, DRB1*0408, and DRB1*0409 are found in 95% of the North American population), and in which these alleles are always homozygous.

To determine the order in which the single nucleotide sequences should be performed, the sequence differences among alleles are evaluated to determine which of the bases will yield the most information, and the circumstances in which knowledge about two or more bases yields a definitive typing. To do this, we look first at base A, for example, to determine which alleles can be identified unequivocally from a knowledge of the position of the A bases within the sample. One way to approach this is to set up a table which shows the base for each allele at each polymorphic site, as shown in Table 1, and to determine the pattern which would be observed if the A's in the table were detected. Each unique pattern can be definitively typed using this one sequencing reaction. For the DR4 alleles, every allele (including all of the most widely distributed alleles) except DRB1*0413 and DTB1*0416 produces a unique pattern. All of the other bases effectively identify fewer allelic types, and therefore the A reaction is done first. Further, it is very likely that any given group of samples could be entirely typed using this single sequencing reaction. In the event that samples were not definitively typed using this first sequencing reaction, any second sequencing reaction performed on the untyped samples would distinguish between DRB1*0413 and DTB1*0416.

to perform the reactions is reduced. Further, since each sample must be analyzed by electrophoresis, fewer electrophoresis runs need to be performed. For example, in an

| VGEN. P-019-US |
| --- |

| Allele | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|---|---|---|
| 401 | g | A | g | c | A | g | A | g | A | t | c | c | g | c | g | c | g | A | A | g | c | c | t | c | t | t | g |
| 402 | g | A | g | c | A | g | A | g | A | t | c | c | g | A | A | g | c | g | A | g | c | t | g | t | g | g | A |
| 403 | g | A | g | c | A | g | A | g | A | t | c | c | g | c | g | c | g | A | g | g | A | t | g | c | t | t | g |
| 404 | g | A | g | c | A | g | A | g | A | t | c | c | g | c | g | c | g | A | g | g | c | t | g | c | t | t | g |
| 405 | g | A | g | c | A | g | c | A | g | c | c | c | g | c | g | c | g | A | g | g | c | c | t | t | g | g | A |
| 406 | g | A | g | c | A | g | A | g | A | t | c | c | g | c | g | c | g | A | g | g | A | t | g | c | t | t | g |
| 407 | g | A | g | c | A | g | A | g | A | t | c | c | g | c | g | c | g | A | g | g | A | c | t | t | g | g | A |
| 408 | t | c | c | t | t | g | A | g | A | t | c | c | g | c | g | c | g | A | g | g | c | c | t | t | g | g | A |
| 409 | t | c | c | t | t | g | A | A | g | c | c | c | g | c | g | c | g | A | A | g | c | c | t | t | g | g | A |
| 410 | g | A | g | c | A | g | A | A | g | c | c | c | g | c | g | c | g | A | g | g | c | t | g | t | g | g | A |
| 411 | g | A | g | c | A | g | A | A | g | c | c | c | g | c | g | c | g | A | g | g | A | t | g | t | g | g | A |
| 412 | g | A | g | c | A | g | A | A | g | c | c | c | g | A | A | g | c | A | g | c | t | t | g | t | g | g | A |
| 413 | t | c | c | c | A | g | A | g | A | t | c | c | g | c | g | c | g | A | A | g | c | t | g | t | g | g | A |
| 414 | t | c | c | t | t | g | A | g | A | t | c | c | g | A | A | g | c | g | A | g | c | c | t | t | g | g | A |
| 415 | g | A | g | c | A | g | A | g | A | t | A | g | g | t | A | g | c | A | g | g | c | c | t | t | g | g | A |
| 416 | t | c | c | t | A | g | A | g | A | t | c | c | c | c | g | c | g | A | A | g | c | c | t | t | g | g | A |
| 417 | t | c | c | t | A | g | A | A | g | c | c | c | g | c | g | c | g | A | g | g | A | c | t | t | g | g | A |
| 418 | t | c | c | t | t | A | A | g | A | t | c | c | g | A | A | g | c | A | g | c | t | t | g | t | g | g | A |
| 419 | t | c | c | t | A | g | c | g | A | t | c | c | g | c | g | c | g | A | g | g | c | c | t | t | g | g | A |

The significance in terms of cost per test of using the method of the invention is easily appreciated. Determining the DR4 allelic type of 100 samples using traditional 4 nucleotide DNA sequencing requires performance of a total of 400 sequencing reactions. Assuming a cost (reagents plus labor) of $20.00 per test, this would result in a cost per patient of $80.00. In contrast, in the test using the method of the invention, only the first test for the positions of A is performed on all samples. Even assuming the statistically unlikely event that 5% of the population is of type DRB1*0413 or DTB1*0416, 95 positive typings will result. The remaining 5 samples are tested using a second (G, C or T) sequencing reaction, with the result that all 5 samples are definitively typed. Thus, the cost for performing these 100 typings using the method of the invention is $2,100 or $21 per patient.

In some cases, the second sequencing reaction performed may not yield unique patterns for all of the samples tested. In this case, prior to performing a third sequencing reaction, it is desirable to combine the results of the first two sequencing reactions and evaluate these composite results for unique base patterns. Thus, for example, a first and second sequencing reaction may have four alleles which can be characterized as follows

|  | A pattern | T pattern |
|---|---|---|
| Allele 1 | 1 3 5 | 2 6 11 |
| Allele 2 | 1 3 5 | 2 4 11 |
| Allele 3 | 3 4 5 | 2 6 11 |
| Allele 4 | 3 4 5 | 2 7 11 |

Allele 2 and Allele 4 give unique results from the T-sequence reaction alone, and can therefore be typed based upon this information. Alleles 1 and 3, however have the same T-sequencing pattern. Because these two allele have different A-sequencing reaction patterns, however, they are clearly distinguishable and can be typed based upon the combined patterns without further testing.

This substantial reduction in the number of sequencing reactions means that the cost of reagents and labor required automated DNA sequencer having 40 lanes, such as the Pharmacia A.L.F.T™ (Pharmacia, Uppsala, Sweden), up to 40 patient samples can be run on a gel rather than 10 patient samples using 4 lanes each. In systems such as the Applied Biosystems Inc. 377™, (Foster City, Calif.) which permit the use of 4 fluorescent dyes per lane, 4 patient samples may be run per lane instead of one patient sample per lane. Use of networked high-speed DNA sequencers with software that can combine data taken from different instruments, such as HELIOS™ software, (both from Visible Genetics Inc., Toronto, Canada) can also enhance this method.

This same methodology can be applied to virtually any known polymorphic genetic locus to obtain efficient characterization of the locus. For example, identification of alleles in the highly polymorphic Human Leukocyte Antigen (HLA) gene system (Parham, P. et al. Nature of Polymorphism in HLA-A, -B and -C Molecules. Proc. Natl. Acad. Sci., USA 85: 4005–4009 (1988)) will benefit greatly from the method. Moreover, the method is not limited to human polymorphisms. It may be used for other animals, plants, bacteria, viruses or fungi. It may be used to distinguish the allelic variants present among a mixed sample of organisms. In human or animal diagnostics, the method can be used to identify which subspecies of bacteria or viruses are present in a body sample. This diagnosis could be essential for determining whether drug resistant strains of pathogens are present in an individual.

After developing an assay methodology in the manner outlined above for a particular known polymorphic gene, the first step of the method of the invention is obtaining a suitable sample of material for testing using this methodology. The genetic material tested using the invention may be chromosomal DNA, messenger RNA, CDNA, or any other form of nucleic acid polymer which is subject to testing to evaluate polymorphism, and may be derived from various sources including whole blood, tissue samples including tumor cells, sperm, and hair follicles.

In some cases, it may be advantageous to amplify the sample, for example using polymerase chain reaction amplification, to create one which is enriched in the particular genetic sequences of interest. Amplification primers for this purpose are advantageously designed to be highly selective for the genetic locus in question. For example, for HLA Class I testing group specific and locus specific amplification primers have been disclosed in U.S. Pat. No. 5,424,184 and Cereb et al., "Locus-specific amplification of HLA class I genes from genomic DNA: locus-specific sequences in the first and third introns of HLA-A, -B and -C alleles," Tissue Antigens 45: 1–11 (1995) which are incorporated herein by reference.

Once a suitable sample is obtained, the sample is combined with the first sequencing reaction mixture. This reaction mixture contains a template-dependent nucleic acid polymerase, A, T, G and C nucleotide feedstocks, one type of chain terminating nucleotide and a sequencing primer.

The selection of the template dependent nucleic acid polymerase is not critical to the success of the invention. A preferred polymerases, however, is Thermo Sequenase™, a thermostable polymerase enzyme marketed by ABI. Other suitable enzymes include regular Sequenase™ and other enzymes usied in sequencing reactions.

Selection of appropriate sequencing primers is generally done by finding a part of the gene, either in an intron or an exon, that lies near (within about 300 nt) the polymorphic region of the gene which is to be evaluated, is 5' to the polymorphic region (either on the sense or the antisense strand), and that is highly conserved among all known alleles of the gene. A sequencing primer that will hybridize to such a region with high specificity can then be used to sequence through the polymorphic region. Other aspects of primer quality, such as lack of palindromic sequence, and preferred G/C content are identified in the U.S. patent application Ser. No. 08/271,946, U.S. Pat. No. 5,545,527.

In some cases it is impossible to select one primer that can satisfy all the above demands. Two or more primers may be necessary to test among some sub-groups of a genetic locus. In these cases it is necessary to attempt a sequencing reaction using one of the primers. If hybridization is successful, and a sequencing reaction proceeds, then the results can be used to determine allele identity. If no sequencing reactions occur, it may be necessary to use another one of the primers.

The sequencing reaction mixture is processed through multiple cycles during which primer is extended and then separated from the template DNA from the sample and new primer is reannealed with the template. At the end of these cycles, the product oligonucleotide fragments are separated by gel electrophoresis and detected. This process is well known in the art. Preferably, this separation is performed in an apparatus of the type described in U.S. patent application Ser. No. 08/353,932, U.S. Pat. No. 5,710,628, the continuation in part thereof filed on Dec. 12, 1995 as International Patent Application No. PCT/US95/15951 (Attorney Docket No. VGEN.P-009-WO) using thin microgels as described in International Patent Application No. PCT/US95/95/14531, all of which applications are incorporated herein by reference.

The practice of the instant invention is assisted by technically advanced methods for precisely identifying the location of nucleotides in a genetic locus using single nucleotide sequencing. The issue is that in the technique of single nucleotide sequencing using dideoxy-sequencing/electrophoresis analysis it is sometimes a challenge to determine how many nucleotides fall between two of the identified nucleotides:

| A _ _ _ A A | or | A _ _ _ _ A A |
|---|---|---|

In many cases, there is little difficulty, particularly when short sequencing reaction products are examined (200 nt or less), because the electrophoretic separation of reaction products follows a highly predictable pattern. A computer or a human can easily determine the number of nucleotides lying between two identified nucleotides by simply measuring the gap and determining the number of singleton peaks that would otherwise fall in the gap. The problem becomes relevant in longer electrophoresis runs where resolution and separation of sequencing reaction fragments is lost. In addition, loss of consistency in maintaining the temperature, electric field strength or other operating parameters can lead to inconsistencies in the spacing between peaks and ambiguities in interpretation. Such ambiguities can prevent accurate identification of alleles.

One simple way to resolve these problems is to run a "control" lane with all samples which identifies all possible nucleotide fragment lengths from the genetic locus being sequenced, for example by performing a reaction which includes all 4 dideoxy nucleotides. The control lane indicates precisely the number of nucleotides that lie in the gaps between the identified nucleotides, as in FIG. 3.

Any sequencing format can use such a control lane, be it "manual" sequencing, using radioactively labeled oligonucleotides and autoradiograph analysis (see Chp 7, Current Protocols in Molecular Biology, Eds. Ausubel, F. M. et al, (John Wiley & Sons; 1995))), or automated laser fluorescence systems.

An improved method for identifying alleles, which does not rely on measuring the number of nucleotides lying between two identified nucleotides is disclosed in U.S. patent application Ser. No. 08/497,202. Briefly, this method relies on the actual shape of the data signal ("wave form") received from an automated laser fluorescence DNA analysis system. The method compares the patient sample wave form to a database of wave forms representing the known alleles of the gene. The known wave form that best matches the sample wave form identifies the allele in the sample.

As discussed below, some wave forms may represent heterozygote mixtures. The database should include wave forms from all known heterozygote combinations to ensure that the matching process includes the full variety of possibilities. When a patient sample is found to be a possible heterozygote, the software can be designed to inform the user of the next analytical test that should be performed to help distinguish among possible allelic members of the heterozygote.

Heterozygous polymorphic genetic loci need special consideration. Where more than one variant of the same loci exists in the patient sample, complex results are obtained when single lane sequencing begins at a commonly shared sequencing primer site. This problem is also found in traditional 4 lane sequencing (see Santamaria P., et al "HLA Class I Sequence-Based Typing" Human Immunology 37, 39–50 (1993)). However, FIG. 2 illustrates an improved method for distinguishing heterozygotic alleles using the present invention.

The problem presented by a heterozygous allele is illustrated in FIG. 2a. The observed data from single nucleotide sequencing of the A lane can not point to the presence of a unique allele. Either the loci is heterozygous or a new allele has been found. (For well studied genetic loci, new alleles will be rare, so heterozygosity may be assumed.) The problem flows from a mixture of alleles in the patient sample which is analyzed. For example, the observed data may result from the additive combination of allele 1 and allele 2.

Where there are more than two possible alleles, it is necessary to compare each of the known allelic variants to the observed data to see if they could result in the observed data. Each heterozygote pair will have its own distinct pattern. FIG. 3b illustrates that alleles 3 and 4 can not underlie the observed data because certain A nucleotides in those alleles are not represented in the data. They are thus eliminated from consideration. The remaining alleles 5, 6, and 7 could be used in combination with others to generate the observed data.

In the case of human genomic DNA, only two alleles at any one loci can generally be present (one from each chromosome). It is necessary, therefore, to combine all known alleles to determine if they can be additively combined to result in the observed data. (In fact, the data appearance of known and hypothetical heterozygote pairs can be prepared and stored in an additional database to facilitate analysis.) In FIG. 3b combination of alleles 5 and 6 will result in the observed data, and combination of neither 5 & 7 nor 6 & 7 gives the desired result. Therefore, if only the alleles 3 to 7 were known, the only two that could possibly be combined to result in the observed data would be 5 and 6. Allelic identification could be made on this basis.

In some cases, where more than one pair of alleles can be combined to obtain the observed data, as in FIG. 3c, it is necessary to determine the relative locations of other nucleotides in order to distinguish which allelic pair is present. Identification of another specific type of nucleotide serves to distinguish which pair of alleles is present. FIG. 3d shows further, that sometimes observed data may appear to be a homozygote for one allele, but in fact it may consist of a heterozygote pair, either including the suggested allele, or not. The alleles that might lead to such confusion, by masking possible heterozygotes, can be identified in the known allele database. Identification of these alleles can not be confirmed unless further tests are made which can confirm whether a heterozygote underlies the observed data.

All of the analyses of comparing the known alleles to the observed data can be conveniently assisted by the use of high speed computer analysis.

In rare cases, such as in FIG. 4, sequencing of all 4 nucleotides will not permit identification of which allelic pair is present. The ambiguity may be reported as such, especially if the clinical need for distinguishing is low. Alternatively, high stringency hybridization probes may be used, as they can identify the presence of specific allelic variants. Protocols for hybridization probes are well known in the art (see Chp 6.4, Current Protocols in Molecular Biology, Eds. Ausubel, F. M. et al, (John Wiley & Sons; 1995)).

Occasionally, quantitative measurements of the amount of sequencing reaction products may be sufficient to distinguish whether only one allele has an A at a specific loci, or both. It is found experimentally, however, that quantitative analysis of sequencing peak heights can only rarely assist in the analysis.

Quantitative analysis proves more useful for resolving the problem of "allelic dropout". In cases of allelic dropout, sequencing reactions identify an apparent homozygote, but only because the sequencing primer has failed to initiate sequencing reactions on one of the two alleles. This may have resulted from heterogeneity at the sequencing primer site itself, which prevents the primer from hybridizing to the target site or initiating chain extension. (This problem should be rare as sequencing primers according to the invention are designed to hybridize generally to highly conserved areas of the genome).

Allelic dropout is resolved by amplifying both alleles from genomic DNA using quantitative polymerase chain reaction (see for example, Chp 15, Current Protocols in Molecular Biology, Eds. Ausubel, F. M. et al, (John Wiley & Sons; 1995)). The sequencing primer is used as one of a pair of PCR primers. A fragment of DNA spanning the alleles in question is amplified quantitatively. At the end of the reaction, quantities of PCR products will be only half the expected amount if only one allele is being amplified. Quantitative analysis can be made on the basis of peak heights of amplified bans observed by automated DNA sequencing instruments.

A plurality of pathogens can produce even more complex results from single nucleotide sequencing. The complexity flows from an unlimited number of variants of the pathogen that may be present in the patient sample. For example, viruses, and bacteria may have variable surface antigen coding domains which allow them to evade host immune system detection. To avoid this problem of variability, the genetic locus selected for examination is preferably highly conserved among all variants of the pathogen, such as ribosomal DNA or functionally critical protein coding regions of DNA. Where variable regions of the pathogen must be analyzed, an extended series of comparisons between the observed data and the known alleles can assist the diagnosis by determining which alleles are not substantial components of the observed data.

The method of the present invention lends itself to the construction of tailored kits which provide components for the sequencing reactions. As described in the examples, these components include oligonucleotide sequencing primers, enzymes for sequencing, nucleotide and dideoxynucleoside preparations, and buffers for reactions. Unlike conventional kits, however, the amount of each type of dideoxynucleoside required for any given assay is not the same. Thus, for an assay in which the A sequencing reaction is performed first and on all samples, the amount of dideoxy-A included in the kit may be 5 to 10 times greater than the amount of the other dideoxynucleosides.

The following examples are included to illustrate aspects of the instant invention and are not intended to limit the invention in any way.

EXAMPLE 1

Identification of HLA Class II gene alleles present in an individual patient sample can be performed using the method of the instant invention. For example, DRB1 is a polymorphic HLA Class II gene with at least 107 known alleles (See Bodmer et al. Nomenclature for Factors of the HLA System, 1994. Hum. Imm. 41, 1–20 (1994)).

The broad serological subtype of the patient sample DRB1 allele is first determined by attempting to amplify the allele using group specific primers.

Genomic DNA is prepared from the patient sample using a standard technique such as proteinase K proteolysis. Allele amplification is carried out in Class II PCR buffer:
10 mM Tris pH 8.4
50 mM KCl
1.5 mM MgCl2
0.1% gelatin
200 microM each of dATP, dCTP, dGTP and dTTP
12 pmol of each group specific primer
40 ng patient sample genomic DNA Groups are amplified separately. The group specific primers employed are:

|  |  | PRODUCT SIZE |
|---|---|---|
| DR 1 | | |
| 5'-PRIMER: TTGTGGCAGCTTAAGTTTGAAT | [Seq ID No. 1] | 195&196 |
| 3'-PRIMERS: CCGCCTCTGCTCCAGGAG | [Seq ID No. 2] | |
|             CCCGCTCGTCTTCCAGGAT | [Seq ID No. 3] | |
| DR2 (15 AND 16) | | |
| 5'-PRIMER: TCCTGTGGCAGCCTAAGAG | [Seq ID No. 4] | 197&213 |
| 3'-PRIMERS: CCGCGCCTGCTCCAGGAT | [Seq ID No. 5] | |
|             AGGTGTCCACCGCGCGGCG | [Seq ID No. 6] | |
| DR3, 8, 11, 12, 13, 14 | | |
| 5'-PRIMER: CACGTTTCTTGGAGTACTCTAC | [Seq ID No. 7] | 270 |
| 3'-PRIMER: CCGCTGCACTGTGAAGCTCT | [Seq ID No. 8] | |
| DR4 | | |
| 5'-PRIMER: GTTTCTTGGAGCAGGTTAAACA | [Seq ID No. 9] | 260 |
| 3'-PRIMERS: CTGCACTGTGAAGCTCTCAC | [Seq ID No. 10] | |
|             CTGCACTGTGAAGCTCTCCA | [Seq ID No. 11] | |
| DR7 | | |
| 5'-PRIMER: CCTGTGGCAGGGTAAGTATA | [Seq ID No. 12] | 232 |
| 3'-PRIMER: CCCGTAGTTGTGTCTGCACAC | [Seq ID No. 13] | |
| DR9 | | |
| 5'-PRIMER: GTTTCTTGAAGCAGGATAAGTTT | [Seq ID No. 14] | 236 |
| 3'-PRIMER: CCCGTAGTTGTGTCTGCACAC | [Seq ID No. 15] | |
| DR10 | | |
| 5'-PRIMER: CGGTTGCTGGAAAGACGCG | [Seq ID No. 16] | 204 |
| 3'-PRIMER: CTGCACTGTGAAGCTCTCAC | [Seq ID No. 17] | |

The 5'-PRIMERS of the above groups are terminally labelled with a fluorophore such as a fluorescein dye at the 5'- end.

The reaction mixture is mixed well. 2.5 units Taq Polymerase are added and mixed immediately prior to thermocycling. The reaction tubes are placed in a Robocycler Gradient 96 (Stratagene, Inc.) and subject to thermal cycling as follows:

| 1 cycle | 94 C. | 2 min |
|---|---|---|
| 10 cycles | 94 C. | 15 sec |
| | 67 C. | 1 min |
| 20 cycles | 94 C. | 10 sec |
| | 61 C. | 50 sec |
| | 72 C. | 39 sec |
| 1 cycle | 72 C. | 2 min |

4 C cool on ice until ready for electrophoretic analysis.

Seven reactions (one for each group specific primer set) are performed. After amplification 2 microl of each of the PCR products are pooled, and mixed with 11 microl of loading buffer consisting of 100% formamide with 5 mg/ml dextran blue. The products are run on a 6% polyacrylamide electrophoresis gel in an automated fluorescence detection apparatus such as the Pharmacia A.L.F.™ (Uppsala, Sweden). Size determinations are performed based on migration distances of known size fragments. The serological group is identified by the length of the successfully amplified fragment. Only one fragment will appear if both alleles belong to the same serological group, otherwise, for heterozygotes containing alleles from two different groups, two fragments appear.

Once the serological group is determined, specificity within the group is determined by single nucleotide sequencing according to the invention.

Each positive group from above is individually amplified for sequence analysis. The PCR amplification primers are a biotinylated 3'-PRIMER amp B:

(5' Biotin-CCGCTGCACTGTGAAGCTCT 3')     [Seq ID No. 8]

and the appropriate 5'-PRIMER described above. The conditions for amplification are identical to the method described above.

After amplification sequencing is performed using the following sequencing primer:

5' - GAGTGTCATTTCTTCAA     [Seq ID No. 18]

The PCR product (10 ul) is mixed with 10 ul of washed Dynabeads M-280 (as per manufacturers recommendations, Dynal, Oslo, Norway) and incubated for 1 hr at room temperature. The beads are washed with 50 ul of 1× BW buffer (10 mM Tris, pH 7.5, 1 mM EDTA, 2M NaCl) followed by 50 ul of 1× TE buffer (10 mM Tris, 1 mM EDTA). After washing, resuspend the beads in 10 ul of TE and take 3 ul for the sequencing reaction which consists of:
3 ul bound beads
3 ul sequencing primer (30 ng total)
2 ul 10× sequencing buffer (260 mM Tris-HCl, pH 9.5, 65 mM MgCl2)
2 ul of Thermo Sequenase™ (Amersham Life Sciences, Cleveland) (diluted 1:10 from stock)
3 ul H2O
Final Volume=13 ul. Keep this sequencing reaction mix on ice.

Remove 3 ul of the sequencing reaction mix and add to 3 ul of one of the following mixtures, depending on the termination reaction desired.

A termination reaction:
750 microM each of dATP, dCTP, dGTP, and dTTP; 2.5 microM ddATP C termination reaction:
750 microM each of dATP, dCTP, dGTP, and dTTP; 2.5 microM ddCTP G termination reaction:
750 microM each of dATP, dCTP, dGTP, and dTTP; 2.5 microM ddGTP T termination reaction:
750 microM each of dATP, dCTP, dGTP, and dTTP; 2.5 microM ddTTP
Total termination reaction volume: 6 ul
Cycle the termination reaction mixture in a Robocycler for 25 cycles (or fewer if found to be satisfactory):

| | |
|---|---|
| 95 C. | 30 sec |
| 50 C. | 10 sec |
| 70 C. | 30 sec |

After cycling add 12 ul of loading buffer consisting of 100% formamide with 5 mg/ml dextran blue, and load appropriate volume to an automated DNA sequencing apparatus, such as a Pharmacia A.L.F.

Allele identification requires analysis of results from the automated DNA sequencing apparatus as in FIG. 5. Fragment length analysis revealed that one allele of the patient sample was from the DR4 serological subtype (data not shown). Single nucleotide sequencing was then performed to distinguish among the possible DR4 alleles. Lane 1 illustrates the results of single nucleotide sequencing for the "C" nucleotide of a patient sample (i.e. using the C termination reaction, above). Lanes 2 and 3 represent C nucleotide sequence results for 2 of the 22 known DR4 alleles. Similar results for the 20 other alleles are stored in a database. The patient sample is then compared to the known alleles using one or more of the methods disclosed in US Patent Application Serial No. US 08/497,202.

In FIG. 5, Lane 1 first requires alignment with the database results. The alignment requires determination of one or more normalization coefficients (for stretching or shrinking the results of lane 1) to provide a high degree of overlap (i.e. maximize the intersection) with the previously aligned database results. The alignment co-efficient(s) may be calculated using the Genetic Algorithm method of the above noted application; or another method. The normalization coefficients are then applied to Lane 1. The aligned result of Lane 1 is then systematically correlated to each of the 22 known alleles.

Figure 6:
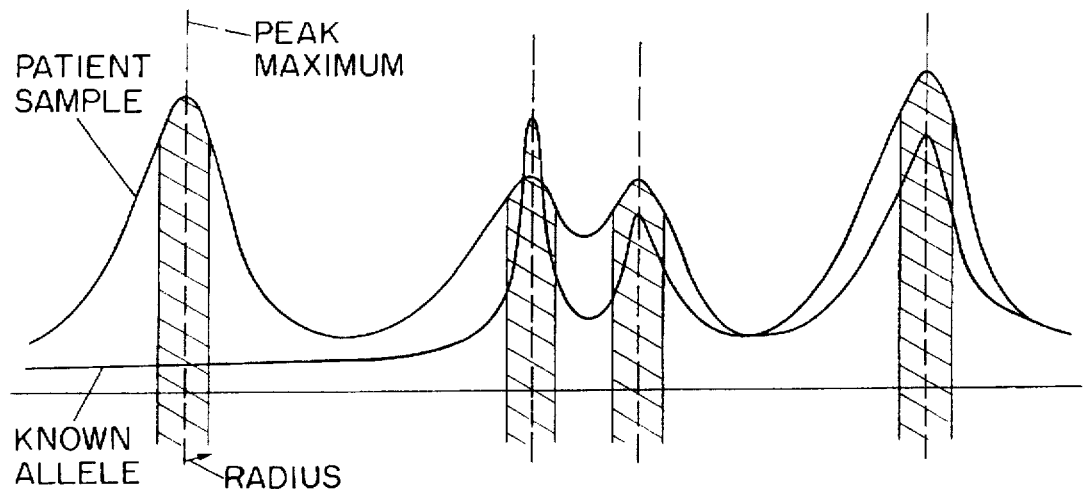
FIG. 6 illustrates peak-by-peak correlation of sequencing results.

The correlation takes place on a peak by peak basis as illustrated in FIG. 6. Each peak in the aligned patient data stream, representing a discrete sequencing reaction termination product, is identified. (Minor peaks representing sequencing artifacts are ignored.) The area under each peak is calculated within a limited radius of the peak maxima (i.e. 20 data points for A.L.F. Sequencer results). A similar calculation is made for the area under the curve of the known allele at the same point. The swath of overlapping areas is then compared. Any correlation below a threshold of reasonable variation, for example 80%, indicates that a peak is present in the patient data stream and not in the other. If one peak is missing, then the known allele is rejected as a possible identifier of the sample.

The reverse comparison is also made: peaks in the known data stream are identified and compared, one by one, to the patient sample results. Again, the presence of a peak in one data stream, that is not present in the other, eliminates the known data stream as an identifier of the sample.

In FIG. 5, lane 2, for allele DRB1*0405, has a peak (marked X) not found in the patient sample. Peak comparison between aligned lane 1 and lane 2 will fall below threshold at the peak marked X. Lane 3 is for part of known allele DRB1*0401. In this case, each peak is found to have a correlate in the other data stream. DRB1*0401 may therefore identify the patient sample. (The results illustrated are much shorter than the 200–300 nt usually used for comparison, so identity of the patient sample is not confirmed until the full diagnostic sequence is compared.)

EXAMPLE 2

Figure 7:
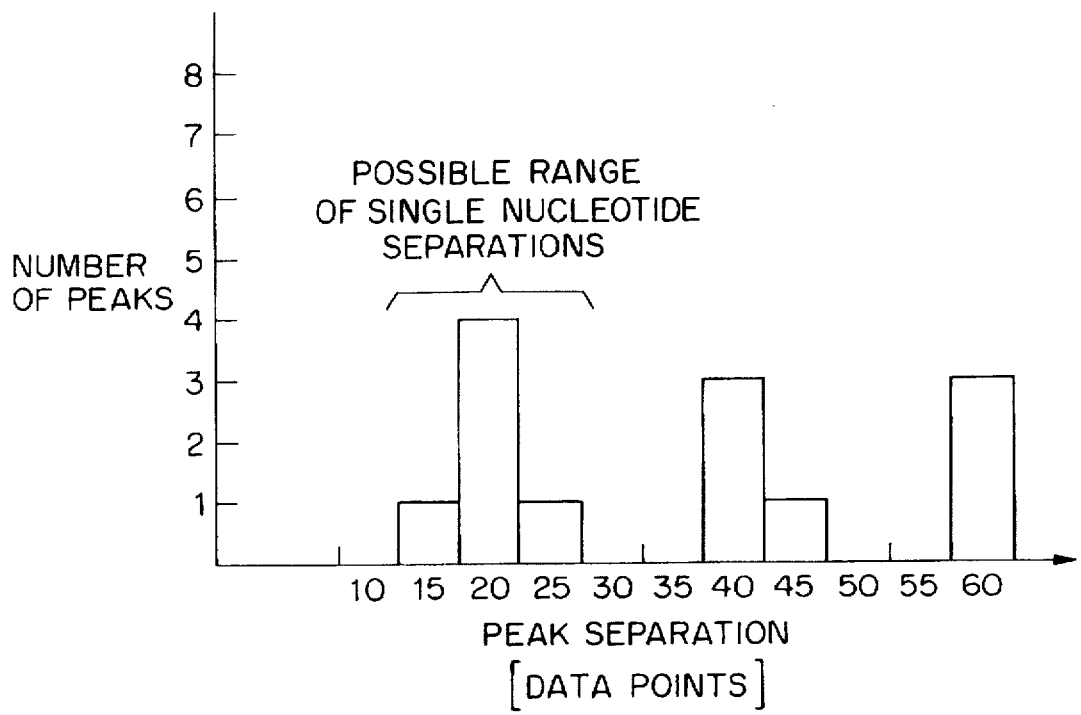
FIG. 7 shows a plot of the maxima of each data peak plotted against the separation from the nearest other peak.

Results are obtained from the patient sample according to Example 1, above. The sample results are converted into a "text" file as follows. The maxima of each peak is located and plotted against the separation from the nearest other peak (minor peaks representing noise are ignored), FIG. 7. The peaks that are closest together are assumed to represent single nucleotide separation and an narrow range for single nucleotide separation is determined. A series of timing tracks are proposed which attempts to locate all the peaks in terms of multiples of a possible single nucleotide separation. The timing track that correlates best (by least mean squares analysis) with the maxima of the sample data is selected as the correct timing track. The peak maxima are then plotted on the timing track. The spaces between the peaks are assumed to represent other nucleotides. A text file may now be generated which identifies the location of all nucleotides of one type and the single nucleotide steps in between.

The text file for the patient sample is compared against all known alleles. The known allele that best matches the patient sample identifies the sample.

EXAMPLE 3

For HLA Class II DRBI Serological group DR4, 22 alleles are known. A hierarchy of single nucleotide sequencing reactions can be used to minimize the number of reactions required for identification of which allele is present. Reactions are performed according to the methods of example 1, above.

If it is established from the group specific reaction that only one DRB1 allele is a DR4 subtype, then identification of that allele is made by the following steps:
1. Determine A nucleotide sequence. As listed in Appendix 1, this identifies 16 of 22 known alleles; then
2. Determine G nucleotide sequence. Identifies 10 of 22 known alleles; then
3. Combine A and G sequencing results by computer analysis. Identifies all 22 known alleles.

If the patient sample is identified at any one step, then the following step(s) need not be performed for that sample.

EXAMPLE 4

If the group specific reaction in example 1 indicates that two DR4 alleles are present in the patient sample, then from the 22 known alleles, there are 253 possible allelic pair combinations (22 homozygotes+231 heterozygotes) (See Appendix 1). Again, a hierarchy of single nucleotide sequencing reactions can be used to minimize the number of reactions required for identification of which allelic pair is present. Reactions are performed according to the methods of example 1, above.
1. Sequence G: Distinguishes among 10 homozygote pairs and 64 heterozygote pairs.
2. Sequence A: Distinguishes among 16 homozygote pairs and 23 heterozygote pairs.
3. Combine A and G sequencing results by computer analysis. Identifies all known homozygotes and 169 known heterozygote alleles.
4. Sequence C: Distinguishes among 5 homozygotes pairs and 18 heterozygote pairs.
5. Combine A, C and G sequencing results by computer analysis. Identifies all known homozygotes and 219 heterozygote pairs.

6. Sequence T: Distinguishes one homozygote pair and 5 heterozygote pairs.
7. Combine A, C, C and T sequencing results by computer analysis. Identifies all known homozygotes and 225 heterozygote pairs.
8. If at the end of sequencing the 4 nucleotides, allelic pairs can still not be distinguished, Sequence Specific Oligonucleotide Probes may be used to distinguish which of the pairs are present, according to the invention.

If the patient sample is identified at any one step, then the following step(s) need not be performed for that sample.

This example assumes that all alleles will be equally represented among the patient samples analyzed. If certain alleles predominate in the population, then it may be advantageous to perform reactions definitive for those alleles first, in order to reduce the total number of reactions performed.

EXAMPLE 5

Virtually all the alleles of the HLA Class I C gene can be determined on the basis of exon 2 and 3 genomic DNA sequence alone (Cereb, N et al. "Locus-specific amplification of HLA class I genes from genomic DNA: locus-specific sequences in the first and third introns of HLA-A, -B and -C alleles." Tissue Antigens 45: 1–11 (1995)). The primers used amplify the polymorphic exons 2 and 3 of all C-alleles without any co-amplification of psuedogenes or B or A alleles. These primers utilize C-specific sequences in introns 1, 2 and 3 of the C-locus.

Identification of alleles in a patient sample is performed according to the method of example 1, with the following changes. Patient sample DNA is prepared according to standard methods (Current Protocols in Molecular Biology, Eds. Ausubel, F. M. et al, (John Wiley & Sons; 1995))

The following primers are used to amplify the HLA Class I C gene exon 2:

| Forward Primer; Intron 1 Primer Name: C2I1 | |
|---|---|
| 5' - AGCGAGTGCCCGCCCGGCGA - 3' | SEQ ID No.: 19 |
| Reverse Primer; Intron 2 Primer Name: C2RI2 | |
| 5' - Biotin - ACCTGGCCCGTCCGTGGGGGATGAG - 3' | SEQ ID NO 20 |
| Amplicon size 407 bp. | |

The amplification was carried out in PCR buffer composed of 15.6 mM ammonium sulfate, 67 mM Tris-HCl (pH 8.8), 50 microM EDTA, 1.5 mM MgCl2, 0.01% gelatin, 0.2 mM of each dNTP (dATP, dCTP, dGTP and dTTP) and 0.2 mM of each amplification primer. Prior to amplification 40 ng of patient sample DNA is added followed by 2.5 units of Taq Polymerase (Roche Molecular). The amplification cycle consisted of:

| 1 min | 96 C. |
|---|---|
| 5 cycles | 96 C. 20 sec |
| | 70 C. 45 sec |
| | 72 C. 25 sec |
| 20 cycles | 96 C. 20 sec |
| | 65 C. 50 sec |
| | 72 C. 30 sec |
| 5 cycles | 96 C. 20 sec |
| | 55 C. 60 sec |
| | 72 C. 120 sec |

In a separate reaction, exon 3 of HLA Class I C is amplified using the following primers:

| Forward primer; intron 2-exon 3 border Primer name: C3I2E3 | |
|---|---|
| 5' Biotin - GACCGCGGGGCCGGGGCCAGGG - 3' | SEQ ID NO.: 21 |
| Reverse primer; intron 3 Primer name: C3RI3 | |
| 5' - GGAGATGGGGAAGGCTCCCCACT - 3' | SEQ ID No.: 22 |
| Amplicon size 333 bp. | |

The same reaction conditions as listed for exon 2 are used to amplify the DNA.

Sequencing reactions are next performed according to the method of example 1 using one of the following 5' fluorescent labeled sequencing primers:

| Exon 2: Forward sequencing | |
|---|---|
| 5' - CCGGGGCGCAGGTCACGA - 3' (Intron 1) | SEQ ID NO.: 23 |
| Exon 2: Reverse sequencing | |
| 5' - GGAGGGTCGGGCGGGTCT - 3' (Intron 2) | SEQ ID NO.: 24 |
| Exon 3: Reverse sequencing | |
| 5' - CGGGACGTCGCAGAGGAA - 3' (Intron 3) | SEQ ID No.: 25 |

The termination reaction selected depends on whether a forward or reverse primer is chosen. Appendix 2 lists which alleles can be distinguished if a forward primer is used (i.e. sequencing template is the anti-sense strand). If a reverse primer is used for sequencing, the termination reaction selected is the complementary one (A for T, C for G, and vice versa).

Homozygotic alleles of HLA Class I C are effectively distinguished by the following sequencing order (see Appendix 2 for details):

1. Determine sense strand A nucleotide sequence. Identifies 24 of 35 known homozygotes; then
2. Determine sense strand C nucleotide sequence. Identifies 16 of 35 known homozygotes; then
3. Combine A and C sequencing results by computer analysis. Identifies 31 of 35 known homozygotes;
4. Determine sense strand G nucleotide sequence. Identifies 14 of 35 known homozygotes; then
5. Combine A, C and G sequencing results by computer analysis. Identifies 33 of 35 known homozygotes.

The remaining 2 alleles, Cw*12022.hla and Cw*12021.hla can not be distinguished by nucleotide sequencing of only exons 2 and 3. Further reactions according to the invention may be performed to distinguish among these alleles.

If the patient sample is identified at any one step, then the following step(s) need not be performed for that sample.

Heterozygotes are analyzed on the same basis; the order of single nucleotide sequencing reactions is determined by picking which reactions will distinguish among the greatest number of samples (data not shown), and performing those reactions first.

This example assumes that all alleles will be equally represented among the patient samples analyzed. If certain alleles predominate in the population, then it may be advantageous to perform reactions definitive for those alleles first, in order to reduce the total number of reactions performed.

EXAMPLE 6

One lipoprotein lipase (LPL) variant (Asn291Ser) is associated with reduced HDL cholesterol levels in premature atherosclerosis. This variant has a single missense mutation of A to C at nucleotide 1127 of the sense strand in Exon 6. This variant can be distinguished according to the instant invention as follows.

Exon 6 of the LPL gene from a patient sample is amplified with a 5' PCR primer located in intron 5 near the 5' boundary of exon 6

---
(5' -GCCGAGATACAATCTTGGTG- 3')   [Seq ID No. 26]
---

The 3' PCR primer is located in exon 6 a short distance from the Asn291Ser mutation and labeled with biotin.

---
(5' -biotin- CAGGTACATTTTGCTGCTTC - 3').   [Seq ID No. 27]
---

PCR amplification reactions were performed according to the methods detailed in Reymer, P. W. A., et al. (1995). ("A lipoprotein lipase mutation (Asn291Ser) is associated with reduced HDL cholesterol levels in premature atherosclerosis." Nature Genetics 10: 28–34 (1995).)

Sequencing analysis was then performed according to the Thermo Sequenase™ (Amersham) method of example 1, using a fluorescent labeled version of the 5' PCR primer noted above.

Since the deleterious allele has a C at nucleotide 1127 of the sense strand, the C termination sequencing reaction was performed. The results of the reaction were recorded on an automated DNA sequencing apparatus and analyzed at the 1127 site. The patient sample either carries the C at that site, or it does not. If a C is present, the patient is identified as having the "unhealthy" allele. If no C is present, then the "healthy" form of the allele is identified. Patient reports may be prepared on this basis.

EXAMPLE 7

Health care workers currently seek to distinguish among Chlamydia trachomatis strains to determine the molecular epidemiologic association of a range of diseases with infecting genotype (See Dean, D. et al "Major Outer Membrane Protein Variants of Chlamydia trachomatis Are Associated with Severe Upper Genital Tract Infections and Histopathology in San Francisco." J. Infect. Dis. 172: 1013–22 (1995)). According to the instant invention, the presence and genotype of pure and mixed cultures of C. trachomatis may be determined by examining the C. trachomatis ompl gene (Outer Membrane Protein 1).

The ompl gene has at least 4 variable sequence ("VS") domains that may be used to distinguish among the 15 known genotypes (Yuan, Y et al. "Nucleotide and Deduced Amino Acid Sequences for the Four Variable Domains of the Major Outer Membrane Proteins of the 15 Chlamydia trachomatis Serovars" Infect. Immun. 57 1040–1049 (1989)). Logically, to determine presence of a genotype in detectable amounts in a possibly mixed culture, the technique must search for a nucleotide which is unique among the genotypes at a specific location. For example, genotype H has a unique A at site 284. No other genotype shares this A, therefore it is diagnostic of genotype H. Other genotypes have other unique nucleotides. On this basis, a preferred order of single nucleotide sequencing may be determined, as follows.

Patient samples were obtained and DNA was extracted using standard SDS/Proteinase K methods. The sample was alternatively prepared according to Dean, D et al. "Comparison of the major outer membrane protein sequence variant regions of B/Ba isolates: a molecular epidemiologic approach to Chlamydia trachomatis infections." J. Infect. Dis 166: 383–992 (1992). In brief, the sample was washed once with 1× PBS, centrifuged at 14,000 g, resuspended in dithiothreitol and TRIS-EDTA buffer, and boiled before PCR. One microliter of the sample was used in a 100 microliter reaction volume that contained 50 mM KCl, 10 mM TRIS-Cl (pH 8.1), 1.5 mM MgCl2, 100 micromolar (each) DATP, dCTP, dGTP, and dTTP, 2.5 U of ampli-Taq DNA polymerase (Perkin-Elmer Cetus, Foster City, Calif.), and 150 ng of each primer. The upstream primer was F11:

---
5' - ACCACTTGGTGTGACGCTATCAG - 3'   [Seq ID No. 28]
(base pair [bp] position 154–176),
--- and the downstream primer was B11:

---
5' - CGGAATTGTGCATTTACGTGAG - 3'   [Seq ID No. 29]
(bp position 1187–1166).
---

The thermocycler temperature profile was 95 degrees C. for 45 sec, 55 degrees C. for 1 min, and 72 degrees C. for 2 min, with a final extension of 10 min at 72 degrees C. after the last cycle. One microliter of the PCR product was then used in each of two separate nested 100 microliter reactions with primer pair:

---
MF21

5' - CCGACCGCGTCTTGAAAACAGATGT - 3' [Seq ID No. 30], and
MB22

5' - CACCCACATTCCCAGAGAGCT - 3' [Seq ID. No. 31]
--- which flank VS1 (Variable Sequence 1) and VS2, and primer pair

---
MVF3

5' - CGTGCAGCTTTGTGGGAATGT - 3' [Seq ID No. 32], and
MB4

5' - CTACATTTCATCTTGTTCAATTGC - 3' [Seq ID No. 33]
--- which flank VS3 and VS4 (see Dean D. and Stephens R. S. "Identification of individual genotypes of Chlamydia trachomatis in experimentally mixed infections and mixed infections among trachoma patients." J. Clin. Microbiol. 32: 1506–10 (1994).) These primer sets uniformly amplify prototype C. trachomatis serovars A-K and L1-3, including Ba, Da, Ia, and L2a. A sample of each product (10 microliters) was run on a 1.5% agarose gel to confirm the size of the amplification product. All PCR products were purified (GeneClean II; Bio 101, La Jolla, Calif.) according to the manufacturer's instructions.

All samples that were positive for presence of *C. trachomatis* by PCR were subjected to ompl genotyping by single nucleotide sequencing. Amplification for sequencing reactions was performed as above using at least one of the above noted amplification primer pairs, with a 5' biotinylated version of either one of the primers.

The biotinylated strand was separated with Dynal beads and selected termination reactions were performed as in Example 1 using a 5' fluorescent labeled version of MF21 or MVF3.

The selection of termination reactions depends on the degree of resolution among genotypes desired. Only 1–3% of clinical *C. trachomatis* samples contain mixed genotypes. Nonetheless, other pathogens are more commonly mixed, such as HIV, HPV and Hepatitis C. For all these organisms, it is important to have a method of distinguishing heterogenous samples.

The first 25 nt of the T termination reaction for *C. trachomatis* VS1 can be used to distinguish among 3 groups of genotypes, as illustrated in FIG. 8A. The observed results for Sample 1 in FIG. 8A demonstrates that detectable levels of at least one of Group 1 and at least one of the Group 3 genotypes are present. Group 2 is not detected.

Figure 8B:
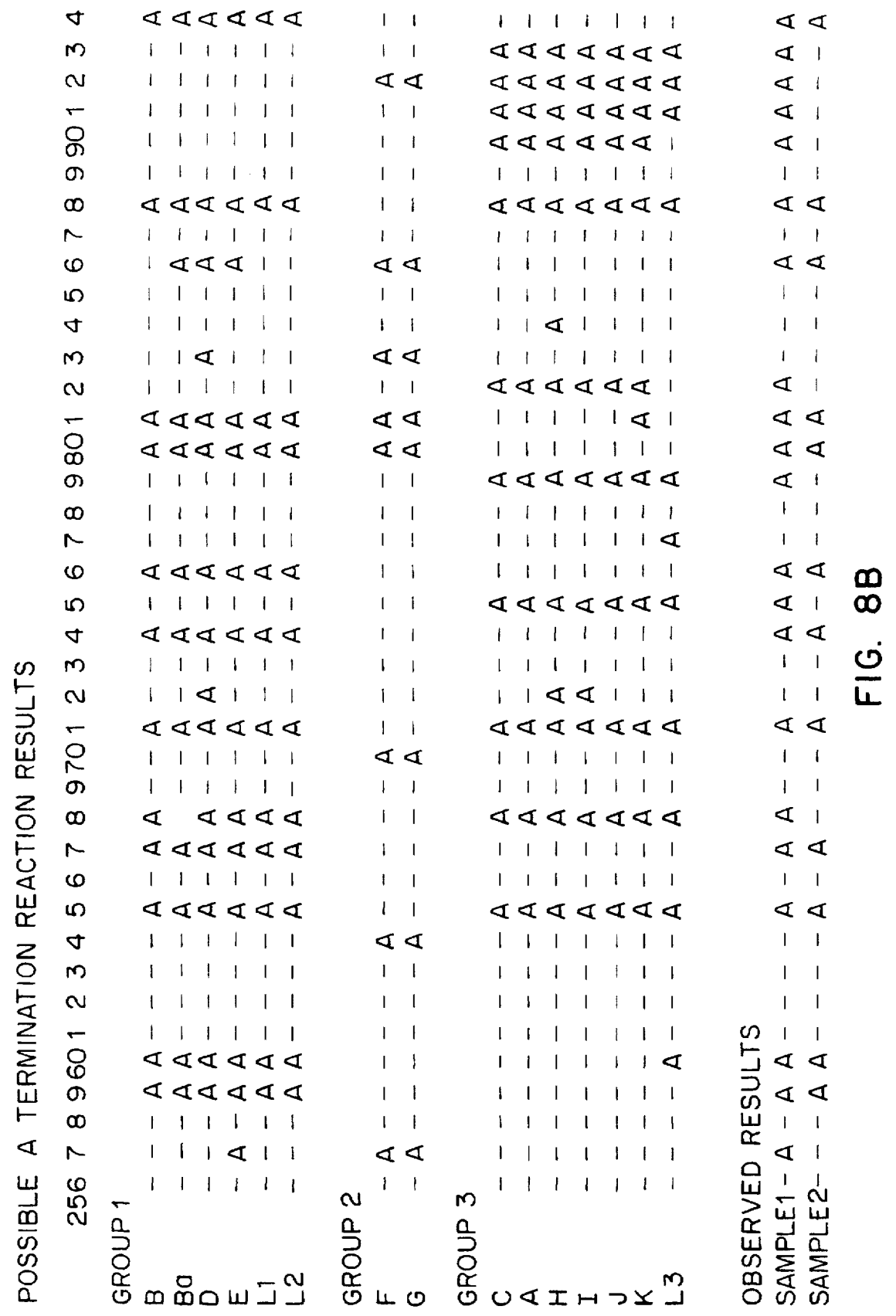

If a higher degree of resolution is required, then further reactions are necessary. To distinguish among possible Group 1s, the VS1 A reaction is performed. FIG. 8B illustrates possible A results. The observed results of Sample 1 shows an A at site 257. This A could be provided by only E, F or G genotypes. Since the T track has already established the absence of both F and G, then E must be among the genotypes present. Further, the absence of an A at 283 indicates that neither D nor F nor G are present. The presence of E and the absence of D, F and G may be reported.

Other Group 1 genotypes may be present in addition to E; they do not appear because their presence is effectively masked by E. Other single nucleotide termination reactions can be performed to distinguish among these other possible contributors, if necessary. The investigator simply determines which single nucleotide reaction will effectively distinguish among the genotypes which may be present and need to be distinguished.

Alternatively, Sample 2, which showed the presence of Group 1 only in the T reaction is shown to be comprised of only Ba genotype because of an absence of A at 268. This shows that both the presence and absence of nucleotides can be used to determine the presence of some genotypes in some circumstances.

The first 25 nt of C and G termination reactions for VS1 only are included in FIG. 8C to show how an investigator can determine which reaction to select and perform. If higher degrees of resolution are required, the termination reactions for VS2, VS3 and VS4 may be performed.

Not only the genotype, but also variants of D, E, F, H, I and K genotypes (as disclosed in Dean, D. et al "Major Outer Membrane Protein Variants of *Chlamydia trachomatis* Are Associated with Severe Upper Genital Tract Infections and Histopathology in San Francisco." J. Infect. Dis. 172: 1013–22 (1995)) may be distinguished by using the above single nucleotide sequencing method.

EXAMPLE 8

The allelic frequencies of HLA Class I C are distributed among Canadians as follows:

| | |
|---|---|
| Cw1 | 5.5 |
| Cw2 | 4.4 |
| Cw4 | 10.0 |
| Cw5 | 6.4 |
| Cw6 | 9.4 |
| Cw7 | 28.9 |
| Cw9 | 7.2 |
| Cw10 | 5.7 |
| Cw11 | 0.5 |
| Unknown/other | 22.0 |

On the basis of this data, it is preferable to perform termination reactions that preferentially distinguish homozygotes and heterozygotes containing a Cw7 allele (i.e. Cw*0701 to Cw*0704) first. This should be followed by Cw4, Cw6 and Cw9, etc. Cw7 is preferentially distinguished on the basis of C/G analysis (122 out of 134 possible combinations). (Plus a further 320 out of the remaining 496). Cw4 is also preferentially distinguished on the basis of C/G analysis (57 out of 69) (with a further 385 out of the remaining 561). Thus the preferred order of termination reactions is as follows:

1. Determine sense strand C nucleotide sequence for patient sample exon 2 and exon 3;
2. Determine sense strand G nucleotide sequence for patient sample exon 2 and exon 3; then
3. Combine G and C sequencing results by computer analysis to identify 442 out of 630 possible combinations, including 179/195 possible allelic pairs containing at least one Cw7 or Cw4 allele (38.9% of Canadian population).
4. Determine sense strand A nucleotide sequence for exons 2 and 3;
5. Combine A, C and G sequencing results by computer analysis. Identifies remaining, undetermined heterozygotes.

The only combinations that can not be distinguished after this point include 2 remaining alleles, Cw*12022 and Cw*12021, which can not be distinguished by nucleotide sequencing of only exons 2 and 3. Further reactions according to the invention may be performed to distinguish among these alleles. Note that since these alleles differ only at a silent mutation, they are identical at the amino acid level, and do not need to be distinguished in practice. Sample reports can simply confirm the presence of the one allele plus either of Cw*12022 or *12021.

If the patient sample is identified at any one step, then the following step(s) need not be performed for that sample.

VGEN.P-019-US

Appendix 1
HLA Class II DRB1; serological group DR4 allele analysis

Sequences obtained from the Strasbourg Data Base
Internet Address = ftp://FTP.EMBL-Heidelberg.DE/pub/databases

Single or multiple nucleotide sequencing may be used to distinguish among the DR4 alleles according to the invention as follows:

Non-Unique Sequences using A:
DRB1*0403 = (DRB1*0407)
DRB1*0405 = (DRB1*0410)
DRB1*0407 = (DRB1*0403)
DRB1*0410 = (DRB1*0405)
DRB1*0413 = (DRB1*0416)
DRB1*0416 = (DRB1*0413)

Unique Sequences using A:
1: DRB1*0401
2: DRB1*0402
3: DRB1*0404
4: DRB1*0406
5: DRB1*0408
6: DRB1*0409
7: DRB1*0411
8: DRB1*0412
9: DRB1*0414
10: DRB1*0415
11: DRB1*0417
12: DRB1*0418
13: DRB1*0419
14: DRB1*0420
15: DRB1*0421
16: DRB1*0422

Non-Unique Sequences using C:
DRB1*0401 = (DRB1*0403, DRB1*0404, DRB1*0406, DRB1*0407, DRB1*0413, DRB1*0419, DRB1*0421)
DRB1*0402 = (DRB1*0415)
DRB1*0403 = (DRB1*0401, DRB1*0404, DRB1*0406, DRB1*0407, DRB1*0413, DRB1*0419, DRB1*0421)
DRB1*0404 = (DRB1*0401, DRB1*0403, DRB1*0406, DRB1*0407, DRB1*0413, DRB1*0419, DRB1*0421)
DRB1*0405 = (DRB1*0410, DRB1*0411)
DRB1*0406 = (DRB1*0401, DRB1*0403, DRB1*0404, DRB1*0407, DRB1*0413, DRB1*0419, DRB1*0421)
DRB1*0407 = (DRB1*0401, DRB1*0403, DRB1*0404, DRB1*0406, DRB1*0413, DRB1*0419, DRB1*0421)
DRB1*0408 = (DRB1*0420)
DRB1*0409 = (DRB1*0417)
DRB1*0410 = (DRB1*0405, DRB1*0411)
DRB1*0411 = (DRB1*0405, DRB1*0410)
DRB1*0413 = (DRB1*0401, DRB1*0403, DRB1*0404, DRB1*0406, DRB1*0407, DRB1*0419, DRB1*0421)
DRB1*0415 = (DRB1*0402)
DRB1*0417 = (DRB1*0409)

Appendix 1 (cont'd)

DRB1*0419 = (DRB1*0401, DRB1*0403, DRB1*0404, DRB1*0406, DRB1*0407, DRB1*0413, DRB1*0421)
DRB1*0420 = (DRB1*0408)
DRB1*0421 = (DRB1*0401, DRB1*0403, DRB1*0404, DRB1*0406, DRB1*0407, DRB1*0413, DRB1*0419)

Unique Sequences using C:
1: DRB1*0412
2: DRB1*0414
3: DRB1*0416
4: DRB1*0418
5: DRB1*0422

Non-Unique Sequences using G:
DRB1*0401 = (DRB1*0407, DRB1*0421)
DRB1*0403 = (DRB1*0404, DRB1*0406)
DRB1*0404 = (DRB1*0403, DRB1*0406)
DRB1*0406 = (DRB1*0403, DRB1*0404)
DRB1*0407 = (DRB1*0401, DRB1*0421)
DRB1*0408 = (DRB1*0416, DRB1*0419, DRB1*0420) DRB1*0409 = (DRB1*0417)
DRB1*0416 = (DRB1*0408, DRB1*0419, DRB1*0420) DRB1*0417 = (DRB1*0409)
DRB1*0419 = (DRB1*0408, DRB1*0416, DRB1*0420) DRB1*0420 = (DRB1*0408, DRB1*0416, DRB1*0419) DRB1*0421 = (DRB1*0401, DRB1*0407)

Unique Sequences using G:
1: DRB1*0402
2: DRB1*0405
3: DRB1*0410
4: DRB1*0411
5: DRB1*0412
6: DRB1*0413
7: DRB1*0414
8: DRB1*0415
9: DRB1*0418
10: DRB1*0422

Non-Unique Sequences using T:
DRB1*0401 = (DRB1*0405, DRB1*0407, DRB1*0408, DRB1*0409, DRB1*0414, DRB1*0416, DRB1*0417, DRB1*0419, DRB1*0420, DRB1*0421) DRB1*0402 = (DRB1*0403, DRB1*0404, DRB1*0406, DRB1*0410, DRB1*0411, DRB1*0413, DRB1*0422)
DRB1*0403 = (DRB1*0402, DRB1*0404, DRB1*0406, DRB1*0410, DRB1*0411, DRB1*0413, DRB1*0422)
DRB1*0404 = (DRB1*0402, DRB1*0403, DRB1*0406, DRB1*0410, DRB1*0411, DRB1*0413, DRB1*0422)
DRB1*0405 = (DRB1*0401, DRB1*0407, DRB1*0408, DRB1*0409, DRB1*0414, DRB1*0416, DRB1*0417, DRB1*0419, DRB1*0420, DRB1*0421) DRB1*0406 = (DRB1*0402, DRB1*0403, DRB1*0404, DRB1*0410, DRB1*0411, DRB1*0413, DRB1*0422)
DRB1*0407 = (DRB1*0401, DRB1*0405, DRB1*0408, DRB1*0409, DRB1*0414, DRB1*0416, DRB1*0417, DRB1*0419, DRB1*0420, DRB1*0421) DRB1*0408 = (DRB1*0401, DRB1*0405, DRB1*0407, DRB1*0409, DRB1*0414, DRB1*0416, DRB1*0417, DRB1*0419, DRB1*0420, DRB1*0421) DRB1*0409 = (DRB1*0401, DRB1*0405, DRB1*0407, DRB1*0408, DRB1*0414, DRB1*0416, DRB1*0417, DRB1*0419, DRB1*0420, DRB1*0421) DRB1*0410 = (DRB1*0402, DRB1*0403, DRB1*0404, DRB1*0406, DRB1*0411, DRB1*0413, DRB1*0422)
DRB1*0411 = (DRB1*0402, DRB1*0403, DRB1*0404, DRB1*0406, DRB1*0410, DRB1*0413, DRB1*0422)
DRB1*0412 = (DRB1*0418)
DRB1*0413 = (DRB1*0402, DRB1*0403, DRB1*0404, DRB1*0406, DRB1*0410, DRB1*0411, DRB1*0422)
DRB1*0414 = (DRB1*0401, DRB1*0405, DRB1*0407, DRB1*0408, DRB1*0409, DRB1*0416, DRB1*0417, DRB1*0419, DRB1*0420, DRB1*0421) DRB1*0416 = (DRB1*0401, DRB1*0405, DRB1*0407, DRB1*0408, DRB1*0409, DRB1*0414, DRB1*0417, DRB1*0419, DRB1*0420, DRB1*0421) DRB1*0417 = (DRB1*0401, DRB1*0405, DRB1*0407, DRB1*0408, DRB1*0409, DRB1*0414, DRB1*0416, DRB1*0419, DRB1*0420, DRB1*0421) DRB1*0418 = (DRB1*0412)
DRB1*0419 = (DRB1*0401, DRB1*0405, DRB1*0407, DRB1*0408, DRB1*0409, DRB1*0414, DRB1*0416, DRB1*0417, DRB1*0420, DRB1*0421) DRB1*0420 = (DRB1*0401, DRB1*0405, DRB1*0407, DRB1*0408, DRB1*0409, DRB1*0414, DRB1*0416, DRB1*0417, DRB1*0419, DRB1*0421) DRB1*0421 = (DRB1*0401, DRB1*0405, DRB1*0407, DRB1*0408, DRB1*0409, DRB1*0414, DRB1*0416, DRB1*0417, DRB1*0419, DRB1*0420) DRB1*0422 = (DRB1*0402, DRB1*0403, DRB1*0404, DRB1*0406, DRB1*0410, DRB1*0411, DRB1*0413)

Appendix 1 (cont'd)

Unique Sequences using T:
1: DRB1*0415

Non-Unique Sequences using AC:
DRB1*0403 = (DRB1*0407)
DRB1*0405 = (DRB1*0410)
DRB1*0407 = (DRB1*0403)
DRB1*0410 = (DRB1*0405)

Unique Sequences using AC:
1: DRB1*0401
2: DRB1*0402
3: DRB1*0404
4: DRB1*0406
5: DRB1*0408
6: DRB1*0409
7: DRB1*0411
8: DRB1*0412
9: DRB1*0413
10: DRB1*0414
11: DRB1*0415
12: DRB1*0416
13: DRB1*0417
14: DRB1*0418
15: DRB1*0419
16: DRB1*0420
17: DRB1*0421
18: DRB1*0422

Non-Unique Sequences using AG:

Unique Sequences using AG:
1: DRB1*0401
2: DRB1*0402
3: DRB1*0403
4: DRB1*0404
5: DRB1*0405
6: DRB1*0406
7: DRB1*0407
8: DRB1*0408
9: DRB1*0409
10: DRB1*0410
11: DRB1*0411
12: DRB1*0412
13: DRB1*0413
14: DRB1*0414
15: DRB1*0415
16: DRB1*0416
17: DRB1*0417
18: DRB1*0418
19: DRB1*0419
20: DRB1*0420
21: DRB1*0421
22: DRB1*0422

Non-Unique Sequences using AT:

Unique Sequences using AT:
1: DRB1*0401
2: DRB1*0402

Appendix 1 (cont'd)

3: DRB1*0403
4: DRB1*0404
5: DRB1*0405
6: DRB1*0406
7: DRB1*0407
8: DRB1*0408
9: DRB1*0409
10: DRB1*0410
11: DRB1*0411
12: DRB1*0412
13: DRB1*0413
14: DRB1*0414
15: DRB1*0415
16: DRB1*0416
17: DRB1*0417
18: DRB1*0418
19: DRB1*0419
20: DRB1*0420
21: DRB1*0421
22: DRB1*0422

Non-Unique Sequences using CG:
DRB1*0401 = (DRB1*0407, DRB1*0421)
DRB1*0403 = (DRB1*0404, DRB1*0406)
DRB1*0404 = (DRB1*0403, DRB1*0406)
DRB1*0406 = (DRB1*0403, DRB1*0404)
DRB1*0407 = (DRB1*0401, DRB1*0421)
DRB1*0408 = (DRB1*0420)
DRB1*0409 = (DRB1*0417)
DRB1*0417 = (DRB1*0409)
DRB1*0420 = (DRB1*0408)
DRB1*0421 = (DRB1*0401, DRB1*0407)

Unique Sequences using CG:
1: DRB1*0402
2: DRB1*0405
3: DRB1*0410
4: DRB1*0411
5: DRB1*0412
6: DRB1*0413
7: DRB1*0414
8: DRB1*0415
9: DRB1*0416
10: DRB1*0418
11: DRB1*0419
12: DRB1*0422

Non-Unique Sequences using CT:
DRB1*0401 = (DRB1*0407, DRB1*0419, DRB1*0421) DRB1*0403 = (DRB1*0404, DRB1*0406, DRB1*0413) DRB1*0404 = (DRB1*0403, DRB1*0406, DRB1*0413) DRB1*0406 = (DRB1*0403, DRB1*0404, DRB1*0413) DRB1*0407 = (DRB1*0401, DRB1*0419, DRB1*0421) DRB1*0408 = (DRB1*0420)
DRB1*0409 = (DRB1*0417)
DRB1*0410 = (DRB1*0411)
DRB1*0411 = (DRB1*0410)
DRB1*0413 = (DRB1*0403, DRB1*0404, DRB1*0406) DRB1*0417 = (DRB1*0409)
DRB1*0419 = (DRB1*0401, DRB1*0407, DRB1*0421) DRB1*0420 = (DRB1*0408)
DRB1*0421 = (DRB1*0401, DRB1*0407, DRB1*0419)

Unique Sequences using CT:
1: DRB1*0402
2: DRB1*0405

- 82 -

Appendix 1 (cont'd)

3: DRB1*0412
4: DRB1*0414
5: DRB1*0415
6: DRB1*0416
7: DRB1*0418
8: DRB1*0422

Non-Unique Sequences using GT:
DRB1*0401 = (DRB1*0407, DRB1*0421)
DRB1*0403 = (DRB1*0404, DRB1*0406)
DRB1*0404 = (DRB1*0403, DRB1*0406)
DRB1*0406 = (DRB1*0403, DRB1*0404)
DRB1*0407 = (DRB1*0401, DRB1*0421)
DRB1*0408 = (DRB1*0416, DRB1*0419, DRB1*0420) DRB1*0409 = (DRB1*0417)
DRB1*0416 = (DRB1*0408, DRB1*0419, DRB1*0420) DRB1*0417 = (DRB1*0409)
DRB1*0419 = (DRB1*0408, DRB1*0416, DRB1*0420) DRB1*0420 = (DRB1*0408, DRB1*0416, DRB1*0419) DRB1*0421 = (DRB1*0401, DRB1*0407)

Unique Sequences using GT:
1: DRB1*0402
2: DRB1*0405
3: DRB1*0410
4: DRB1*0411
5: DRB1*0412
6: DRB1*0413
7: DRB1*0414
8: DRB1*0415
9: DRB1*0418
10: DRB1*0422

Non-Unique Sequences using ACG:

Unique Sequences using ACG:
1: DRB1*0401
2: DRB1*0402
3: DRB1*0403
4: DRB1*0404
5: DRB1*0405
6: DRB1*0406
7: DRB1*0407
8: DRB1*0408
9: DRB1*0409
10: DRB1*0410
11: DRB1*0411
12: DRB1*0412
13: DRB1*0413
14: DRB1*0414
15: DRB1*0415
16: DRB1*0416
17: DRB1*0417
18: DRB1*0418
19: DRB1*0419
20: DRB1*0420
21: DRB1*0421
22: DRB1*0422

Non-Unique Sequences using ACT:

Unique Sequences using ACT:
1: DRB1*0401
2: DRB1*0402

Appendix 1 (cont'd)

3: DRB1*0403
4: DRB1*0404
5: DRB1*0405
6: DRB1*0406
7: DRB1*0407
8: DRB1*0408
9: DRB1*0409
10: DRB1*0410
11: DRB1*0411
12: DRB1*0412
13: DRB1*0413
14: DRB1*0414
15: DRB1*0415
16: DRB1*0416
17: DRB1*0417
18: DRB1*0418
19: DRB1*0419
20: DRB1*0420
21: DRB1*0421
22: DRB1*0422

Non-Unique Sequences using AGT:

Unique Sequences using AGT:
1: DRB1*0401
2: DRB1*0402
3: DRB1*0403
4: DRB1*0404
5: DRB1*0405
6: DRB1*0406
7: DRB1*0407
8: DRB1*0408
9: DRB1*0409
10: DRB1*0410
11: DRB1*0411
12: DRB1*0412
13: DRB1*0413
14: DRB1*0414
15: DRB1*0415
16: DRB1*0416
17: DRB1*0417
18: DRB1*0418
19: DRB1*0419
20: DRB1*0420
21: DRB1*0421
22: DRB1*0422

Non-Unique Sequences using CGT:
DRB1*0401 = (DRB1*0407, DRB1*0421)
DRB1*0403 = (DRB1*0404, DRB1*0406)
DRB1*0404 = (DRB1*0403, DRB1*0406)
DRB1*0406 = (DRB1*0403, DRB1*0404)
DRB1*0407 = (DRB1*0401, DRB1*0421)
DRB1*0408 = (DRB1*0420)
DRB1*0409 = (DRB1*0417)
DRB1*0417 = (DRB1*0409)
DRB1*0420 = (DRB1*0408)
DRB1*0421 = (DRB1*0401, DRB1*0407)

Unique Sequences using CGT:
1: DRB1*0402

- 84 -

Appendix 1 (cont'd)

2: DRB1*0405
3: DRB1*0410
4: DRB1*0411
5: DRB1*0412
6: DRB1*0413
7: DRB1*0414
8: DRB1*0415
9: DRB1*0416
10: DRB1*0418
11: DRB1*0419
12: DRB1*0422

Non-Unique Sequences using ACGT:

Unique Sequences using ACGT:
1: DRB1*0401
2: DRB1*0402
3: DRB1*0403
4: DRB1*0404
5: DRB1*0405
6: DRB1*0406
7: DRB1*0407
8: DRB1*0408
9: DRB1*0409
10: DRB1*0410
11: DRB1*0411
12: DRB1*0412
13: DRB1*0413
14: DRB1*0414
15: DRB1*0415
16: DRB1*0416
17: DRB1*0417
18: DRB1*0418
19: DRB1*0419
20: DRB1*0420
21: DRB1*0421
22: DRB1*0422

/*
* HETEROZYGOTE CASES:
*/

The allelic pair is listed first, followed by the number of other allelic pairs which have the identical appearance according to the sequencing reaction performed. 0 represents an allelic pair that is uniquely identified. 12 indicates that 12 other pairs can not be distinguished by performing the listed reaction.

Unique Sequences using A:

DRB1*0401.hla + DRB1*0402.hla = 1
DRB1*0401.hla + DRB1*0403.hla = 12
DRB1*0401.hla + DRB1*0404.hla = 12
DRB1*0401.hla + DRB1*0405.hla = 16
DRB1*0401.hla + DRB1*0406.hla = 8
DRB1*0401.hla + DRB1*0407.hla = 12
DRB1*0401.hla + DRB1*0408.hla = 15
DRB1*0401.hla + DRB1*0409.hla = 3
DRB1*0401.hla + DRB1*0410.hla = 16
DRB1*0401.hla + DRB1*0411.hla = 3
DRB1*0401.hla + DRB1*0412.hla = 16
DRB1*0401.hla + DRB1*0413.hla = 4
DRB1*0401.hla + DRB1*0414.hla = 3

Appendix 1 (cont'd)

```
DRB1*0401.hla + DRB1*0415.hla = 12
DRB1*0401.hla + DRB1*0416.hla = 4
DRB1*0401.hla + DRB1*0417.hla = 11
DRB1*0401.hla + DRB1*0418.hla = 15
DRB1*0401.hla + DRB1*0419.hla = 19
DRB1*0401.hla + DRB1*0420.hla = 19
DRB1*0401.hla + DRB1*0421.hla = 1
DRB1*0401.hla + DRB1*0422.hla = 0
DRB1*0402.hla + DRB1*0403.hla = 2
DRB1*0402.hla + DRB1*0404.hla = 2
DRB1*0402.hla + DRB1*0405.hla = 1
DRB1*0402.hla + DRB1*0406.hla = 0
DRB1*0402.hla + DRB1*0407.hla = 2
DRB1*0402.hla + DRB1*0408.hla = 4
DRB1*0402.hla + DRB1*0409.hla = 1
DRB1*0402.hla + DRB1*0410.hla = 1
DRB1*0402.hla + DRB1*0411.hla = 0
DRB1*0402.hla + DRB1*0412.hla = 0
DRB1*0402.hla + DRB1*0413.hla = 1
DRB1*0402.hla + DRB1*0414.hla = 0
DRB1*0402.hla + DRB1*0415.hla = 0
DRB1*0402.hla + DRB1*0416.hla = 1
DRB1*0402.hla + DRB1*0417.hla = 0
DRB1*0402.hla + DRB1*0418.hla = 1
DRB1*0402.hla + DRB1*0419.hla = 1
DRB1*0402.hla + DRB1*0420.hla = 1
DRB1*0402.hla + DRB1*0421.hla = 0
DRB1*0402.hla + DRB1*0422.hla = 1
DRB1*0403.hla + DRB1*0404.hla = 12
DRB1*0403.hla + DRB1*0405.hla = 16
DRB1*0403.hla + DRB1*0406.hla = 1
DRB1*0403.hla + DRB1*0407.hla = 0
DRB1*0403.hla + DRB1*0408.hla = 15
DRB1*0403.hla + DRB1*0409.hla = 12
DRB1*0403.hla + DRB1*0410.hla = 16
DRB1*0403.hla + DRB1*0411.hla = 1
DRB1*0403.hla + DRB1*0412.hla = 16
DRB1*0403.hla + DRB1*0413.hla = 7
DRB1*0403.hla + DRB1*0414.hla = 4
DRB1*0403.hla + DRB1*0415.hla = 12
DRB1*0403.hla + DRB1*0416.hla = 7
DRB1*0403.hla + DRB1*0417.hla = 1
DRB1*0403.hla + DRB1*0418.hla = 15
DRB1*0403.hla + DRB1*0419.hla = 19
DRB1*0403.hla + DRB1*0420.hla = 2
DRB1*0403.hla + DRB1*0421.hla = 8
DRB1*0403.hla + DRB1*0422.hla = 12
DRB1*0404.hla + DRB1*0405.hla = 16
DRB1*0404.hla + DRB1*0406.hla = 8
DRB1*0404.hla + DRB1*0407.hla = 12
DRB1*0404.hla + DRB1*0408.hla = 15
DRB1*0404.hla + DRB1*0409.hla = 12
DRB1*0404.hla + DRB1*0410.hla = 16
DRB1*0404.hla + DRB1*0411.hla = 3
DRB1*0404.hla + DRB1*0412.hla = 16
DRB1*0404.hla + DRB1*0413.hla = 7
DRB1*0404.hla + DRB1*0414.hla = 4
DRB1*0404.hla + DRB1*0415.hla = 12
DRB1*0404.hla + DRB1*0416.hla = 7
DRB1*0404.hla + DRB1*0417.hla = 11
DRB1*0404.hla + DRB1*0418.hla = 15
```

Appendix 1 (cont'd)

DRB1*0404.hla + DRB1*0419.hla = 19
DRB1*0404.hla + DRB1*0420.hla = 19
DRB1*0404.hla + DRB1*0421.hla = 8
DRB1*0404.hla + DRB1*0422.hla = 12
DRB1*0405.hla + DRB1*0406.hla = 5
DRB1*0405.hla + DRB1*0407.hla = 16
DRB1*0405.hla + DRB1*0408.hla = 12
DRB1*0405.hla + DRB1*0409.hla = 3
DRB1*0405.hla + DRB1*0410.hla = 2
DRB1*0405.hla + DRB1*0411.hla = 2
DRB1*0405.hla + DRB1*0412.hla = 2
DRB1*0405.hla + DRB1*0413.hla = 11
DRB1*0405.hla + DRB1*0414.hla = 2
DRB1*0405.hla + DRB1*0415.hla = 16
DRB1*0405.hla + DRB1*0416.hla = 11
DRB1*0405.hla + DRB1*0417.hla = 2
DRB1*0405.hla + DRB1*0418.hla = 12
DRB1*0405.hla + DRB1*0419.hla = 7
DRB1*0405.hla + DRB1*0420.hla = 7
DRB1*0405.hla + DRB1*0421.hla = 5
DRB1*0405.hla + DRB1*0422.hla = 16
DRB1*0406.hla + DRB1*0407.hla = 1
DRB1*0406.hla + DRB1*0408.hla = 7
DRB1*0406.hla + DRB1*0409.hla = 2
DRB1*0406.hla + DRB1*0410.hla = 5
DRB1*0406.hla + DRB1*0411.hla = 0
DRB1*0406.hla + DRB1*0412.hla = 5
DRB1*0406.hla + DRB1*0413.hla = 19
DRB1*0406.hla + DRB1*0414.hla = 2
DRB1*0406.hla + DRB1*0415.hla = 8
DRB1*0406.hla + DRB1*0416.hla = 19
DRB1*0406.hla + DRB1*0417.hla = 1
DRB1*0406.hla + DRB1*0418.hla = 7
DRB1*0406.hla + DRB1*0419.hla = 19
DRB1*0406.hla + DRB1*0420.hla = 2
DRB1*0406.hla + DRB1*0421.hla = 8
DRB1*0406.hla + DRB1*0422.hla = 8
DRB1*0407.hla + DRB1*0408.hla = 15
DRB1*0407.hla + DRB1*0409.hla = 12
DRB1*0407.hla + DRB1*0410.hla = 16
DRB1*0407.hla + DRB1*0411.hla = 1
DRB1*0407.hla + DRB1*0412.hla = 16
DRB1*0407.hla + DRB1*0413.hla = 7
DRB1*0407.hla + DRB1*0414.hla = 4
DRB1*0407.hla + DRB1*0415.hla = 12
DRB1*0407.hla + DRB1*0416.hla = 7
DRB1*0407.hla + DRB1*0417.hla = 1
DRB1*0407.hla + DRB1*0418.hla = 15
DRB1*0407.hla + DRB1*0419.hla = 19
DRB1*0407.hla + DRB1*0420.hla = 2
DRB1*0407.hla + DRB1*0421.hla = 8
DRB1*0407.hla + DRB1*0422.hla = 12
DRB1*0408.hla + DRB1*0409.hla = 12
DRB1*0408.hla + DRB1*0410.hla = 12
DRB1*0408.hla + DRB1*0411.hla = 1
DRB1*0408.hla + DRB1*0412.hla = 12
DRB1*0408.hla + DRB1*0413.hla = 15
DRB1*0408.hla + DRB1*0414.hla = 4
DRB1*0408.hla + DRB1*0415.hla = 15
DRB1*0408.hla + DRB1*0416.hla = 15
DRB1*0408.hla + DRB1*0417.hla = 12

- 87 -

Appendix 1 (cont'd)

DRB1*0408.hla + DRB1*0418.hla = 15
DRB1*0408.hla + DRB1*0419.hla = 7
DRB1*0408.hla + DRB1*0420.hla = 7
DRB1*0408.hla + DRB1*0421.hla = 7
DRB1*0408.hla + DRB1*0422.hla = 15
DRB1*0409.hla + DRB1*0410.hla = 3
DRB1*0409.hla + DRB1*0411.hla = 0
DRB1*0409.hla + DRB1*0412.hla = 3
DRB1*0409.hla + DRB1*0413.hla = 3
DRB1*0409.hla + DRB1*0414.hla = 1
DRB1*0409.hla + DRB1*0415.hla = 12
DRB1*0409.hla + DRB1*0416.hla = 3
DRB1*0409.hla + DRB1*0417.hla = 3
DRB1*0409.hla + DRB1*0418.hla = 12
DRB1*0409.hla + DRB1*0419.hla = 2
DRB1*0409.hla + DRB1*0420.hla = 2
DRB1*0409.hla + DRB1*0421.hla = 0
DRB1*0409.hla + DRB1*0422.hla = 3
DRB1*0410.hla + DRB1*0411.hla = 2
DRB1*0410.hla + DRB1*0412.hla = 2
DRB1*0410.hla + DRB1*0413.hla = 11
DRB1*0410.hla + DRB1*0414.hla = 2
DRB1*0410.hla + DRB1*0415.hla = 16
DRB1*0410.hla + DRB1*0416.hla = 11
DRB1*0410.hla + DRB1*0417.hla = 2
DRB1*0410.hla + DRB1*0418.hla = 12
DRB1*0410.hla + DRB1*0419.hla = 7
DRB1*0410.hla + DRB1*0420.hla = 7
DRB1*0410.hla + DRB1*0421.hla = 5
DRB1*0410.hla + DRB1*0422.hla = 16
DRB1*0411.hla + DRB1*0412.hla = 2
DRB1*0411.hla + DRB1*0413.hla = 1
DRB1*0411.hla + DRB1*0414.hla = 0
DRB1*0411.hla + DRB1*0415.hla = 3
DRB1*0411.hla + DRB1*0416.hla = 1
DRB1*0411.hla + DRB1*0417.hla = 0
DRB1*0411.hla + DRB1*0418.hla = 1
DRB1*0411.hla + DRB1*0419.hla = 0
DRB1*0411.hla + DRB1*0420.hla = 0
DRB1*0411.hla + DRB1*0421.hla = 0
DRB1*0411.hla + DRB1*0422.hla = 3
DRB1*0412.hla + DRB1*0413.hla = 11
DRB1*0412.hla + DRB1*0414.hla = 0
DRB1*0412.hla + DRB1*0415.hla = 0
DRB1*0412.hla + DRB1*0416.hla = 11
DRB1*0412.hla + DRB1*0417.hla = 2
DRB1*0412.hla + DRB1*0418.hla = 0
DRB1*0412.hla + DRB1*0419.hla = 7
DRB1*0412.hla + DRB1*0420.hla = 7
DRB1*0412.hla + DRB1*0421.hla = 5
DRB1*0412.hla + DRB1*0422.hla = 16
DRB1*0413.hla + DRB1*0414.hla = 3
DRB1*0413.hla + DRB1*0415.hla = 7
DRB1*0413.hla + DRB1*0416.hla = 4
DRB1*0413.hla + DRB1*0417.hla = 11
DRB1*0413.hla + DRB1*0418.hla = 15
DRB1*0413.hla + DRB1*0419.hla = 19
DRB1*0413.hla + DRB1*0420.hla = 19
DRB1*0413.hla + DRB1*0421.hla = 1
DRB1*0413.hla + DRB1*0422.hla = 4
DRB1*0414.hla + DRB1*0415.hla = 0

- 88 -

Appendix 1 (cont'd)

DRB1*0414.hla + DRB1*0416.hla = 3
DRB1*0414.hla + DRB1*0417.hla = 2
DRB1*0414.hla + DRB1*0418.hla = 1
DRB1*0414.hla + DRB1*0419.hla = 2
DRB1*0414.hla + DRB1*0420.hla = 2
DRB1*0414.hla + DRB1*0421.hla = 0
DRB1*0414.hla + DRB1*0422.hla = 3
DRB1*0415.hla + DRB1*0416.hla = 7
DRB1*0415.hla + DRB1*0417.hla = 11
DRB1*0415.hla + DRB1*0418.hla = 0
DRB1*0415.hla + DRB1*0419.hla = 19
DRB1*0415.hla + DRB1*0420.hla = 19
DRB1*0415.hla + DRB1*0421.hla = 8
DRB1*0415.hla + DRB1*0422.hla = 12
DRB1*0416.hla + DRB1*0417.hla = 11
DRB1*0416.hla + DRB1*0418.hla = 15
DRB1*0416.hla + DRB1*0419.hla = 19
DRB1*0416.hla + DRB1*0420.hla = 19
DRB1*0416.hla + DRB1*0421.hla = 1
DRB1*0416.hla + DRB1*0422.hla = 4
DRB1*0417.hla + DRB1*0418.hla = 12
DRB1*0417.hla + DRB1*0419.hla = 7
DRB1*0417.hla + DRB1*0420.hla = 1
DRB1*0417.hla + DRB1*0421.hla = 7
DRB1*0417.hla + DRB1*0422.hla = 11
DRB1*0418.hla + DRB1*0419.hla = 7
DRB1*0418.hla + DRB1*0420.hla = 7
DRB1*0418.hla + DRB1*0421.hla = 7
DRB1*0418.hla + DRB1*0422.hla = 15
DRB1*0419.hla + DRB1*0420.hla = 19
DRB1*0419.hla + DRB1*0421.hla = 19
DRB1*0419.hla + DRB1*0422.hla = 19
DRB1*0420.hla + DRB1*0421.hla = 19
DRB1*0420.hla + DRB1*0422.hla = 19
DRB1*0421.hla + DRB1*0422.hla = 1

Unique Sequences using C:

DRB1*0401.hla + DRB1*0402.hla = 6
DRB1*0401.hla + DRB1*0403.hla = 29
DRB1*0401.hla + DRB1*0404.hla = 17
DRB1*0401.hla + DRB1*0405.hla = 17
DRB1*0401.hla + DRB1*0406.hla = 29
DRB1*0401.hla + DRB1*0407.hla = 29
DRB1*0401.hla + DRB1*0408.hla = 12
DRB1*0401.hla + DRB1*0409.hla = 12
DRB1*0401.hla + DRB1*0410.hla = 17
DRB1*0401.hla + DRB1*0411.hla = 29
DRB1*0401.hla + DRB1*0412.hla = 11
DRB1*0401.hla + DRB1*0413.hla = 17
DRB1*0401.hla + DRB1*0414.hla = 7
DRB1*0401.hla + DRB1*0415.hla = 6
DRB1*0401.hla + DRB1*0416.hla = 12
DRB1*0401.hla + DRB1*0417.hla = 23
DRB1*0401.hla + DRB1*0418.hla = 17
DRB1*0401.hla + DRB1*0419.hla = 17
DRB1*0401.hla + DRB1*0420.hla = 23
DRB1*0401.hla + DRB1*0421.hla = 17
DRB1*0401.hla + DRB1*0422.hla = 10
DRB1*0402.hla + DRB1*0403.hla = 11
DRB1*0402.hla + DRB1*0404.hla = 6

Appendix 1 (cont'd)

DRB1*0402.hla + DRB1*0405.hla = 6
DRB1*0402.hla + DRB1*0406.hla = 11
DRB1*0402.hla + DRB1*0407.hla = 11
DRB1*0402.hla + DRB1*0408.hla = 7
DRB1*0402.hla + DRB1*0409.hla = 7
DRB1*0402.hla + DRB1*0410.hla = 6
DRB1*0402.hla + DRB1*0411.hla = 11
DRB1*0402.hla + DRB1*0412.hla = 0
DRB1*0402.hla + DRB1*0413.hla = 6
DRB1*0402.hla + DRB1*0414.hla = 0
DRB1*0402.hla + DRB1*0415.hla = 0
DRB1*0402.hla + DRB1*0416.hla = 7
DRB1*0402.hla + DRB1*0417.hla = 17
DRB1*0402.hla + DRB1*0418.hla = 1
DRB1*0402.hla + DRB1*0419.hla = 6
DRB1*0402.hla + DRB1*0420.hla = 17
DRB1*0402.hla + DRB1*0421.hla = 6
DRB1*0402.hla + DRB1*0422.hla = 0
DRB1*0403.hla + DRB1*0404.hla = 29
DRB1*0403.hla + DRB1*0405.hla = 29
DRB1*0403.hla + DRB1*0406.hla = 29
DRB1*0403.hla + DRB1*0407.hla = 29
DRB1*0403.hla + DRB1*0408.hla = 23
DRB1*0403.hla + DRB1*0409.hla = 23
DRB1*0403.hla + DRB1*0410.hla = 29
DRB1*0403.hla + DRB1*0411.hla = 29
DRB1*0403.hla + DRB1*0412.hla = 11
DRB1*0403.hla + DRB1*0413.hla = 29
DRB1*0403.hla + DRB1*0414.hla = 17
DRB1*0403.hla + DRB1*0415.hla = 3
DRB1*0403.hla + DRB1*0416.hla = 23
DRB1*0403.hla + DRB1*0417.hla = 23
DRB1*0403.hla + DRB1*0418.hla = 17
DRB1*0403.hla + DRB1*0419.hla = 29
DRB1*0403.hla + DRB1*0420.hla = 23
DRB1*0403.hla + DRB1*0421.hla = 29
DRB1*0403.hla + DRB1*0422.hla = 10
DRB1*0404.hla + DRB1*0405.hla = 17
DRB1*0404.hla + DRB1*0406.hla = 29
DRB1*0404.hla + DRB1*0407.hla = 29
DRB1*0404.hla + DRB1*0408.hla = 12
DRB1*0404.hla + DRB1*0409.hla = 12
DRB1*0404.hla + DRB1*0410.hla = 17
DRB1*0404.hla + DRB1*0411.hla = 29
DRB1*0404.hla + DRB1*0412.hla = 11
DRB1*0404.hla + DRB1*0413.hla = 17
DRB1*0404.hla + DRB1*0414.hla = 7
DRB1*0404.hla + DRB1*0415.hla = 6
DRB1*0404.hla + DRB1*0416.hla = 12
DRB1*0404.hla + DRB1*0417.hla = 23
DRB1*0404.hla + DRB1*0418.hla = 17
DRB1*0404.hla + DRB1*0419.hla = 17
DRB1*0404.hla + DRB1*0420.hla = 23
DRB1*0404.hla + DRB1*0421.hla = 17
DRB1*0404.hla + DRB1*0422.hla = 10
DRB1*0405.hla + DRB1*0406.hla = 29
DRB1*0405.hla + DRB1*0407.hla = 29
DRB1*0405.hla + DRB1*0408.hla = 12
DRB1*0405.hla + DRB1*0409.hla = 1
DRB1*0405.hla + DRB1*0410.hla = 0
DRB1*0405.hla + DRB1*0411.hla = 1

Appendix 1 (cont'd)

DRB1*0405.hla + DRB1*0412.hla = 2
DRB1*0405.hla + DRB1*0413.hla = 17
DRB1*0405.hla + DRB1*0414.hla = 7
DRB1*0405.hla + DRB1*0415.hla = 6
DRB1*0405.hla + DRB1*0416.hla = 12
DRB1*0405.hla + DRB1*0417.hla = 3
DRB1*0405.hla + DRB1*0418.hla = 17
DRB1*0405.hla + DRB1*0419.hla = 17
DRB1*0405.hla + DRB1*0420.hla = 23
DRB1*0405.hla + DRB1*0421.hla = 17
DRB1*0405.hla + DRB1*0422.hla = 10
DRB1*0406.hla + DRB1*0407.hla = 29
DRB1*0406.hla + DRB1*0408.hla = 23
DRB1*0406.hla + DRB1*0409.hla = 23
DRB1*0406.hla + DRB1*0410.hla = 29
DRB1*0406.hla + DRB1*0411.hla = 29
DRB1*0406.hla + DRB1*0412.hla = 11
DRB1*0406.hla + DRB1*0413.hla = 29
DRB1*0406.hla + DRB1*0414.hla = 17
DRB1*0406.hla + DRB1*0415.hla = 3
DRB1*0406.hla + DRB1*0416.hla = 23
DRB1*0406.hla + DRB1*0417.hla = 23
DRB1*0406.hla + DRB1*0418.hla = 17
DRB1*0406.hla + DRB1*0419.hla = 1
DRB1*0406.hla + DRB1*0420.hla = 1
DRB1*0406.hla + DRB1*0421.hla = 1
DRB1*0406.hla + DRB1*0422.hla = 10
DRB1*0407.hla + DRB1*0408.hla = 23
DRB1*0407.hla + DRB1*0409.hla = 23
DRB1*0407.hla + DRB1*0410.hla = 29
DRB1*0407.hla + DRB1*0411.hla = 29
DRB1*0407.hla + DRB1*0412.hla = 11
DRB1*0407.hla + DRB1*0413.hla = 29
DRB1*0407.hla + DRB1*0414.hla = 17
DRB1*0407.hla + DRB1*0415.hla = 3
DRB1*0407.hla + DRB1*0416.hla = 23
DRB1*0407.hla + DRB1*0417.hla = 23
DRB1*0407.hla + DRB1*0418.hla = 17
DRB1*0407.hla + DRB1*0419.hla = 29
DRB1*0407.hla + DRB1*0420.hla = 23
DRB1*0407.hla + DRB1*0421.hla = 29
DRB1*0407.hla + DRB1*0422.hla = 10
DRB1*0408.hla + DRB1*0409.hla = 8
DRB1*0408.hla + DRB1*0410.hla = 12
DRB1*0408.hla + DRB1*0411.hla = 23
DRB1*0408.hla + DRB1*0412.hla = 17
DRB1*0408.hla + DRB1*0413.hla = 8
DRB1*0408.hla + DRB1*0414.hla = 4
DRB1*0408.hla + DRB1*0415.hla = 2
DRB1*0408.hla + DRB1*0416.hla = 8
DRB1*0408.hla + DRB1*0417.hla = 8
DRB1*0408.hla + DRB1*0418.hla = 8
DRB1*0408.hla + DRB1*0419.hla = 8
DRB1*0408.hla + DRB1*0420.hla = 8
DRB1*0408.hla + DRB1*0421.hla = 12
DRB1*0408.hla + DRB1*0422.hla = 4
DRB1*0409.hla + DRB1*0410.hla = 1
DRB1*0409.hla + DRB1*0411.hla = 3
DRB1*0409.hla + DRB1*0412.hla = 1
DRB1*0409.hla + DRB1*0413.hla = 8
DRB1*0409.hla + DRB1*0414.hla = 4

Appendix 1 (cont'd)

DRB1*0409.hla + DRB1*0415.hla = 2
DRB1*0409.hla + DRB1*0416.hla = 8
DRB1*0409.hla + DRB1*0417.hla = 0
DRB1*0409.hla + DRB1*0418.hla = 8
DRB1*0409.hla + DRB1*0419.hla = 8
DRB1*0409.hla + DRB1*0420.hla = 8
DRB1*0409.hla + DRB1*0421.hla = 12
DRB1*0409.hla + DRB1*0422.hla = 4
DRB1*0410.hla + DRB1*0411.hla = 1
DRB1*0410.hla + DRB1*0412.hla = 2
DRB1*0410.hla + DRB1*0413.hla = 17
DRB1*0410.hla + DRB1*0414.hla = 7
DRB1*0410.hla + DRB1*0415.hla = 6
DRB1*0410.hla + DRB1*0416.hla = 12
DRB1*0410.hla + DRB1*0417.hla = 3
DRB1*0410.hla + DRB1*0418.hla = 17
DRB1*0410.hla + DRB1*0419.hla = 17
DRB1*0410.hla + DRB1*0420.hla = 23
DRB1*0410.hla + DRB1*0421.hla = 17
DRB1*0410.hla + DRB1*0422.hla = 10
DRB1*0411.hla + DRB1*0412.hla = 2
DRB1*0411.hla + DRB1*0413.hla = 29
DRB1*0411.hla + DRB1*0414.hla = 17
DRB1*0411.hla + DRB1*0415.hla = 3
DRB1*0411.hla + DRB1*0416.hla = 23
DRB1*0411.hla + DRB1*0417.hla = 3
DRB1*0411.hla + DRB1*0418.hla = 17
DRB1*0411.hla + DRB1*0419.hla = 29
DRB1*0411.hla + DRB1*0420.hla = 23
DRB1*0411.hla + DRB1*0421.hla = 29
DRB1*0411.hla + DRB1*0422.hla = 10
DRB1*0412.hla + DRB1*0413.hla = 11
DRB1*0412.hla + DRB1*0414.hla = 1
DRB1*0412.hla + DRB1*0415.hla = 0
DRB1*0412.hla + DRB1*0416.hla = 17
DRB1*0412.hla + DRB1*0417.hla = 1
DRB1*0412.hla + DRB1*0418.hla = 0
DRB1*0412.hla + DRB1*0419.hla = 11
DRB1*0412.hla + DRB1*0420.hla = 17
DRB1*0412.hla + DRB1*0421.hla = 11
DRB1*0412.hla + DRB1*0422.hla = 0
DRB1*0413.hla + DRB1*0414.hla = 4
DRB1*0413.hla + DRB1*0415.hla = 6
DRB1*0413.hla + DRB1*0416.hla = 8
DRB1*0413.hla + DRB1*0417.hla = 8
DRB1*0413.hla + DRB1*0418.hla = 8
DRB1*0413.hla + DRB1*0419.hla = 0
DRB1*0413.hla + DRB1*0420.hla = 8
DRB1*0413.hla + DRB1*0421.hla = 17
DRB1*0413.hla + DRB1*0422.hla = 10
DRB1*0414.hla + DRB1*0415.hla = 0
DRB1*0414.hla + DRB1*0416.hla = 4
DRB1*0414.hla + DRB1*0417.hla = 8
DRB1*0414.hla + DRB1*0418.hla = 0
DRB1*0414.hla + DRB1*0419.hla = 4
DRB1*0414.hla + DRB1*0420.hla = 8
DRB1*0414.hla + DRB1*0421.hla = 7
DRB1*0414.hla + DRB1*0422.hla = 0
DRB1*0415.hla + DRB1*0416.hla = 2
DRB1*0415.hla + DRB1*0417.hla = 1
DRB1*0415.hla + DRB1*0418.hla = 0

- 92 -

Appendix 1 (cont'd)

DRB1*0415.hla + DRB1*0419.hla = 6
DRB1*0415.hla + DRB1*0420.hla = 1
DRB1*0415.hla + DRB1*0421.hla = 6
DRB1*0415.hla + DRB1*0422.hla = 0
DRB1*0416.hla + DRB1*0417.hla = 8
DRB1*0416.hla + DRB1*0418.hla = 8
DRB1*0416.hla + DRB1*0419.hla = 8
DRB1*0416.hla + DRB1*0420.hla = 8
DRB1*0416.hla + DRB1*0421.hla = 12
DRB1*0416.hla + DRB1*0422.hla = 4
DRB1*0417.hla + DRB1*0418.hla = 8
DRB1*0417.hla + DRB1*0419.hla = 8
DRB1*0417.hla + DRB1*0420.hla = 8
DRB1*0417.hla + DRB1*0421.hla = 23
DRB1*0417.hla + DRB1*0422.hla = 4
DRB1*0418.hla + DRB1*0419.hla = 8
DRB1*0418.hla + DRB1*0420.hla = 8
DRB1*0418.hla + DRB1*0421.hla = 17
DRB1*0418.hla + DRB1*0422.hla = 0
DRB1*0419.hla + DRB1*0420.hla = 0
DRB1*0419.hla + DRB1*0421.hla = 0
DRB1*0419.hla + DRB1*0422.hla = 10
DRB1*0420.hla + DRB1*0421.hla = 1
DRB1*0420.hla + DRB1*0422.hla = 4
DRB1*0421.hla + DRB1*0422.hla = 10

Unique Sequences using G:

DRB1*0401.hla + DRB1*0402.hla = 4
DRB1*0401.hla + DRB1*0403.hla = 5
DRB1*0401.hla + DRB1*0404.hla = 5
DRB1*0401.hla + DRB1*0405.hla = 1
DRB1*0401.hla + DRB1*0406.hla = 5
DRB1*0401.hla + DRB1*0407.hla = 2
DRB1*0401.hla + DRB1*0408.hla = 5
DRB1*0401.hla + DRB1*0409.hla = 4
DRB1*0401.hla + DRB1*0410.hla = 1
DRB1*0401.hla + DRB1*0411.hla = 1
DRB1*0401.hla + DRB1*0412.hla = 1
DRB1*0401.hla + DRB1*0413.hla = 2
DRB1*0401.hla + DRB1*0414.hla = 2
DRB1*0401.hla + DRB1*0415.hla = 4
DRB1*0401.hla + DRB1*0416.hla = 2
DRB1*0401.hla + DRB1*0417.hla = 4
DRB1*0401.hla + DRB1*0418.hla = 1
DRB1*0401.hla + DRB1*0419.hla = 5
DRB1*0401.hla + DRB1*0420.hla = 5
DRB1*0401.hla + DRB1*0421.hla = 2
DRB1*0401.hla + DRB1*0422.hla = 2
DRB1*0402.hla + DRB1*0403.hla = 2
DRB1*0402.hla + DRB1*0404.hla = 2
DRB1*0402.hla + DRB1*0405.hla = 0
DRB1*0402.hla + DRB1*0406.hla = 2
DRB1*0402.hla + DRB1*0407.hla = 4
DRB1*0402.hla + DRB1*0408.hla = 5
DRB1*0402.hla + DRB1*0409.hla = 3
DRB1*0402.hla + DRB1*0410.hla = 0
DRB1*0402.hla + DRB1*0411.hla = 0
DRB1*0402.hla + DRB1*0412.hla = 0
DRB1*0402.hla + DRB1*0413.hla = 1
DRB1*0402.hla + DRB1*0414.hla = 0

Appendix 1 (cont'd)

```
DRB1*0402.hla + DRB1*0415.hla = 0
DRB1*0402.hla + DRB1*0416.hla = 1
DRB1*0402.hla + DRB1*0417.hla = 3
DRB1*0402.hla + DRB1*0418.hla = 0
DRB1*0402.hla + DRB1*0419.hla = 5
DRB1*0402.hla + DRB1*0420.hla = 5
DRB1*0402.hla + DRB1*0421.hla = 4
DRB1*0402.hla + DRB1*0422.hla = 1
DRB1*0403.hla + DRB1*0404.hla = 2
DRB1*0403.hla + DRB1*0405.hla = 3
DRB1*0403.hla + DRB1*0406.hla = 2
DRB1*0403.hla + DRB1*0407.hla = 2
DRB1*0403.hla + DRB1*0408.hla = 8
DRB1*0403.hla + DRB1*0409.hla = 3
DRB1*0403.hla + DRB1*0410.hla = 2
DRB1*0403.hla + DRB1*0411.hla = 2
DRB1*0403.hla + DRB1*0412.hla = 2
DRB1*0403.hla + DRB1*0413.hla = 2
DRB1*0403.hla + DRB1*0414.hla = 5
DRB1*0403.hla + DRB1*0415.hla = 2
DRB1*0403.hla + DRB1*0416.hla = 2
DRB1*0403.hla + DRB1*0417.hla = 5
DRB1*0403.hla + DRB1*0418.hla = 2
DRB1*0403.hla + DRB1*0419.hla = 8
DRB1*0403.hla + DRB1*0420.hla = 8
DRB1*0403.hla + DRB1*0421.hla = 5
DRB1*0403.hla + DRB1*0422.hla = 2
DRB1*0404.hla + DRB1*0405.hla = 3
DRB1*0404.hla + DRB1*0406.hla = 2
DRB1*0404.hla + DRB1*0407.hla = 2
DRB1*0404.hla + DRB1*0408.hla = 8
DRB1*0404.hla + DRB1*0409.hla = 3
DRB1*0404.hla + DRB1*0410.hla = 2
DRB1*0404.hla + DRB1*0411.hla = 2
DRB1*0404.hla + DRB1*0412.hla = 2
DRB1*0404.hla + DRB1*0413.hla = 2
DRB1*0404.hla + DRB1*0414.hla = 5
DRB1*0404.hla + DRB1*0415.hla = 2
DRB1*0404.hla + DRB1*0416.hla = 2
DRB1*0404.hla + DRB1*0417.hla = 5
DRB1*0404.hla + DRB1*0418.hla = 2
DRB1*0404.hla + DRB1*0419.hla = 8
DRB1*0404.hla + DRB1*0420.hla = 8
DRB1*0404.hla + DRB1*0421.hla = 5
DRB1*0404.hla + DRB1*0422.hla = 2
DRB1*0405.hla + DRB1*0406.hla = 3
DRB1*0405.hla + DRB1*0407.hla = 0
DRB1*0405.hla + DRB1*0408.hla = 3
DRB1*0405.hla + DRB1*0409.hla = 0
DRB1*0405.hla + DRB1*0410.hla = 0
DRB1*0405.hla + DRB1*0411.hla = 0
DRB1*0405.hla + DRB1*0412.hla = 0
DRB1*0405.hla + DRB1*0413.hla = 3
DRB1*0405.hla + DRB1*0414.hla = 0
DRB1*0405.hla + DRB1*0415.hla = 0
DRB1*0405.hla + DRB1*0416.hla = 0
DRB1*0405.hla + DRB1*0417.hla = 0
DRB1*0405.hla + DRB1*0418.hla = 0
DRB1*0405.hla + DRB1*0419.hla = 3
DRB1*0405.hla + DRB1*0420.hla = 3
DRB1*0405.hla + DRB1*0421.hla = 1
```

- 94 -

Appendix 1 (cont'd)

DRB1*0405.hla + DRB1*0422.hla = 0
DRB1*0406.hla + DRB1*0407.hla = 2
DRB1*0406.hla + DRB1*0408.hla = 8
DRB1*0406.hla + DRB1*0409.hla = 3
DRB1*0406.hla + DRB1*0410.hla = 2
DRB1*0406.hla + DRB1*0411.hla = 2
DRB1*0406.hla + DRB1*0412.hla = 2
DRB1*0406.hla + DRB1*0413.hla = 2
DRB1*0406.hla + DRB1*0414.hla = 5
DRB1*0406.hla + DRB1*0415.hla = 2
DRB1*0406.hla + DRB1*0416.hla = 2
DRB1*0406.hla + DRB1*0417.hla = 5
DRB1*0406.hla + DRB1*0418.hla = 2
DRB1*0406.hla + DRB1*0419.hla = 8
DRB1*0406.hla + DRB1*0420.hla = 8
DRB1*0406.hla + DRB1*0421.hla = 5
DRB1*0406.hla + DRB1*0422.hla = 2
DRB1*0407.hla + DRB1*0408.hla = 2
DRB1*0407.hla + DRB1*0409.hla = 4
DRB1*0407.hla + DRB1*0410.hla = 3
DRB1*0407.hla + DRB1*0411.hla = 0
DRB1*0407.hla + DRB1*0412.hla = 0
DRB1*0407.hla + DRB1*0413.hla = 2
DRB1*0407.hla + DRB1*0414.hla = 2
DRB1*0407.hla + DRB1*0415.hla = 0
DRB1*0407.hla + DRB1*0416.hla = 2
DRB1*0407.hla + DRB1*0417.hla = 3
DRB1*0407.hla + DRB1*0418.hla = 0
DRB1*0407.hla + DRB1*0419.hla = 2
DRB1*0407.hla + DRB1*0420.hla = 2
DRB1*0407.hla + DRB1*0421.hla = 2
DRB1*0407.hla + DRB1*0422.hla = 2
DRB1*0408.hla + DRB1*0409.hla = 2
DRB1*0408.hla + DRB1*0410.hla = 5
DRB1*0408.hla + DRB1*0411.hla = 2
DRB1*0408.hla + DRB1*0412.hla = 2
DRB1*0408.hla + DRB1*0413.hla = 2
DRB1*0408.hla + DRB1*0414.hla = 2
DRB1*0408.hla + DRB1*0415.hla = 2
DRB1*0408.hla + DRB1*0416.hla = 2
DRB1*0408.hla + DRB1*0417.hla = 2
DRB1*0408.hla + DRB1*0418.hla = 2
DRB1*0408.hla + DRB1*0419.hla = 2
DRB1*0408.hla + DRB1*0420.hla = 2
DRB1*0408.hla + DRB1*0421.hla = 5
DRB1*0408.hla + DRB1*0422.hla = 2
DRB1*0409.hla + DRB1*0410.hla = 0
DRB1*0409.hla + DRB1*0411.hla = 0
DRB1*0409.hla + DRB1*0412.hla = 0
DRB1*0409.hla + DRB1*0413.hla = 1
DRB1*0409.hla + DRB1*0414.hla = 1
DRB1*0409.hla + DRB1*0415.hla = 3
DRB1*0409.hla + DRB1*0416.hla = 1
DRB1*0409.hla + DRB1*0417.hla = 0
DRB1*0409.hla + DRB1*0418.hla = 0
DRB1*0409.hla + DRB1*0419.hla = 2
DRB1*0409.hla + DRB1*0420.hla = 2
DRB1*0409.hla + DRB1*0421.hla = 4
DRB1*0409.hla + DRB1*0422.hla = 1
DRB1*0410.hla + DRB1*0411.hla = 0
DRB1*0410.hla + DRB1*0412.hla = 0

- 95 -

Appendix 1 (cont'd)

DRB1*0410.hla + DRB1*0413.hla = 0
DRB1*0410.hla + DRB1*0414.hla = 3
DRB1*0410.hla + DRB1*0415.hla = 0
DRB1*0410.hla + DRB1*0416.hla = 0
DRB1*0410.hla + DRB1*0417.hla = 0
DRB1*0410.hla + DRB1*0418.hla = 0
DRB1*0410.hla + DRB1*0419.hla = 5
DRB1*0410.hla + DRB1*0420.hla = 5
DRB1*0410.hla + DRB1*0421.hla = 1
DRB1*0410.hla + DRB1*0422.hla = 0
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 0
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 2
DRB1*0411.hla + DRB1*0420.hla = 2
DRB1*0411.hla + DRB1*0421.hla = 1
DRB1*0411.hla + DRB1*0422.hla = 0
DRB1*0412.hla + DRB1*0413.hla = 0
DRB1*0412.hla + DRB1*0414.hla = 0
DRB1*0412.hla + DRB1*0415.hla = 0
DRB1*0412.hla + DRB1*0416.hla = 0
DRB1*0412.hla + DRB1*0417.hla = 0
DRB1*0412.hla + DRB1*0418.hla = 0
DRB1*0412.hla + DRB1*0419.hla = 2
DRB1*0412.hla + DRB1*0420.hla = 2
DRB1*0412.hla + DRB1*0421.hla = 1
DRB1*0412.hla + DRB1*0422.hla = 0
DRB1*0413.hla + DRB1*0414.hla = 0
DRB1*0413.hla + DRB1*0415.hla = 1
DRB1*0413.hla + DRB1*0416.hla = 0
DRB1*0413.hla + DRB1*0417.hla = 1
DRB1*0413.hla + DRB1*0418.hla = 0
DRB1*0413.hla + DRB1*0419.hla = 2
DRB1*0413.hla + DRB1*0420.hla = 2
DRB1*0413.hla + DRB1*0421.hla = 2
DRB1*0413.hla + DRB1*0422.hla = 0
DRB1*0414.hla + DRB1*0415.hla = 0
DRB1*0414.hla + DRB1*0416.hla = 0
DRB1*0414.hla + DRB1*0417.hla = 1
DRB1*0414.hla + DRB1*0418.hla = 0
DRB1*0414.hla + DRB1*0419.hla = 2
DRB1*0414.hla + DRB1*0420.hla = 2
DRB1*0414.hla + DRB1*0421.hla = 2
DRB1*0414.hla + DRB1*0422.hla = 0
DRB1*0415.hla + DRB1*0416.hla = 1
DRB1*0415.hla + DRB1*0417.hla = 0
DRB1*0415.hla + DRB1*0418.hla = 0
DRB1*0415.hla + DRB1*0419.hla = 2
DRB1*0415.hla + DRB1*0420.hla = 2
DRB1*0415.hla + DRB1*0421.hla = 4
DRB1*0415.hla + DRB1*0422.hla = 1
DRB1*0416.hla + DRB1*0417.hla = 1
DRB1*0416.hla + DRB1*0418.hla = 0
DRB1*0416.hla + DRB1*0419.hla = 2
DRB1*0416.hla + DRB1*0420.hla = 2
DRB1*0416.hla + DRB1*0421.hla = 2
DRB1*0416.hla + DRB1*0422.hla = 0

Appendix 1 (cont'd)

DRB1*0417.hla + DRB1*0418.hla = 0
DRB1*0417.hla + DRB1*0419.hla = 2
DRB1*0417.hla + DRB1*0420.hla = 2
DRB1*0417.hla + DRB1*0421.hla = 4
DRB1*0417.hla + DRB1*0422.hla = 1
DRB1*0418.hla + DRB1*0419.hla = 2
DRB1*0418.hla + DRB1*0420.hla = 2
DRB1*0418.hla + DRB1*0421.hla = 1
DRB1*0418.hla + DRB1*0422.hla = 0
DRB1*0419.hla + DRB1*0420.hla = 2
DRB1*0419.hla + DRB1*0421.hla = 5
DRB1*0419.hla + DRB1*0422.hla = 2
DRB1*0420.hla + DRB1*0421.hla = 5
DRB1*0420.hla + DRB1*0422.hla = 2
DRB1*0421.hla + DRB1*0422.hla = 2

Unique Sequences using T:

DRB1*0401.hla + DRB1*0402.hla = 53
DRB1*0401.hla + DRB1*0403.hla = 53
DRB1*0401.hla + DRB1*0404.hla = 53
DRB1*0401.hla + DRB1*0405.hla = 15
DRB1*0401.hla + DRB1*0406.hla = 53
DRB1*0401.hla + DRB1*0407.hla = 17
DRB1*0401.hla + DRB1*0408.hla = 17
DRB1*0401.hla + DRB1*0409.hla = 15
DRB1*0401.hla + DRB1*0410.hla = 52
DRB1*0401.hla + DRB1*0411.hla = 52
DRB1*0401.hla + DRB1*0412.hla = 52
DRB1*0401.hla + DRB1*0413.hla = 53
DRB1*0401.hla + DRB1*0414.hla = 17
DRB1*0401.hla + DRB1*0415.hla = 53
DRB1*0401.hla + DRB1*0416.hla = 17
DRB1*0401.hla + DRB1*0417.hla = 15
DRB1*0401.hla + DRB1*0418.hla = 53
DRB1*0401.hla + DRB1*0419.hla = 17
DRB1*0401.hla + DRB1*0420.hla = 17
DRB1*0401.hla + DRB1*0421.hla = 17
DRB1*0401.hla + DRB1*0422.hla = 53
DRB1*0402.hla + DRB1*0403.hla = 26
DRB1*0402.hla + DRB1*0404.hla = 26
DRB1*0402.hla + DRB1*0405.hla = 52
DRB1*0402.hla + DRB1*0406.hla = 26
DRB1*0402.hla + DRB1*0407.hla = 53
DRB1*0402.hla + DRB1*0408.hla = 53
DRB1*0402.hla + DRB1*0409.hla = 52
DRB1*0402.hla + DRB1*0410.hla = 25
DRB1*0402.hla + DRB1*0411.hla = 25
DRB1*0402.hla + DRB1*0412.hla = 25
DRB1*0402.hla + DRB1*0413.hla = 26
DRB1*0402.hla + DRB1*0414.hla = 53
DRB1*0402.hla + DRB1*0415.hla = 26
DRB1*0402.hla + DRB1*0416.hla = 53
DRB1*0402.hla + DRB1*0417.hla = 52
DRB1*0402.hla + DRB1*0418.hla = 26
DRB1*0402.hla + DRB1*0419.hla = 53
DRB1*0402.hla + DRB1*0420.hla = 53
DRB1*0402.hla + DRB1*0421.hla = 53
DRB1*0402.hla + DRB1*0422.hla = 26
DRB1*0403.hla + DRB1*0404.hla = 26
DRB1*0403.hla + DRB1*0405.hla = 52

Appendix 1 (cont'd)

DRB1*0403.hla + DRB1*0406.hla = 26
DRB1*0403.hla + DRB1*0407.hla = 53
DRB1*0403.hla + DRB1*0408.hla = 53
DRB1*0403.hla + DRB1*0409.hla = 52
DRB1*0403.hla + DRB1*0410.hla = 25
DRB1*0403.hla + DRB1*0411.hla = 25
DRB1*0403.hla + DRB1*0412.hla = 25
DRB1*0403.hla + DRB1*0413.hla = 26
DRB1*0403.hla + DRB1*0414.hla = 53
DRB1*0403.hla + DRB1*0415.hla = 26
DRB1*0403.hla + DRB1*0416.hla = 53
DRB1*0403.hla + DRB1*0417.hla = 52
DRB1*0403.hla + DRB1*0418.hla = 26
DRB1*0403.hla + DRB1*0419.hla = 53
DRB1*0403.hla + DRB1*0420.hla = 53
DRB1*0403.hla + DRB1*0421.hla = 53
DRB1*0403.hla + DRB1*0422.hla = 26
DRB1*0404.hla + DRB1*0405.hla = 52
DRB1*0404.hla + DRB1*0406.hla = 26
DRB1*0404.hla + DRB1*0407.hla = 53
DRB1*0404.hla + DRB1*0408.hla = 53
DRB1*0404.hla + DRB1*0409.hla = 52
DRB1*0404.hla + DRB1*0410.hla = 25
DRB1*0404.hla + DRB1*0411.hla = 25
DRB1*0404.hla + DRB1*0412.hla = 25
DRB1*0404.hla + DRB1*0413.hla = 26
DRB1*0404.hla + DRB1*0414.hla = 53
DRB1*0404.hla + DRB1*0415.hla = 26
DRB1*0404.hla + DRB1*0416.hla = 53
DRB1*0404.hla + DRB1*0417.hla = 52
DRB1*0404.hla + DRB1*0418.hla = 26
DRB1*0404.hla + DRB1*0419.hla = 53
DRB1*0404.hla + DRB1*0420.hla = 53
DRB1*0404.hla + DRB1*0421.hla = 53
DRB1*0404.hla + DRB1*0422.hla = 26
DRB1*0405.hla + DRB1*0406.hla = 52
DRB1*0405.hla + DRB1*0407.hla = 15
DRB1*0405.hla + DRB1*0408.hla = 15
DRB1*0405.hla + DRB1*0409.hla = 15
DRB1*0405.hla + DRB1*0410.hla = 52
DRB1*0405.hla + DRB1*0411.hla = 52
DRB1*0405.hla + DRB1*0412.hla = 52
DRB1*0405.hla + DRB1*0413.hla = 52
DRB1*0405.hla + DRB1*0414.hla = 15
DRB1*0405.hla + DRB1*0415.hla = 52
DRB1*0405.hla + DRB1*0416.hla = 15
DRB1*0405.hla + DRB1*0417.hla = 15
DRB1*0405.hla + DRB1*0418.hla = 52
DRB1*0405.hla + DRB1*0419.hla = 15
DRB1*0405.hla + DRB1*0420.hla = 15
DRB1*0405.hla + DRB1*0421.hla = 15
DRB1*0405.hla + DRB1*0422.hla = 52
DRB1*0406.hla + DRB1*0407.hla = 53
DRB1*0406.hla + DRB1*0408.hla = 53
DRB1*0406.hla + DRB1*0409.hla = 52
DRB1*0406.hla + DRB1*0410.hla = 25
DRB1*0406.hla + DRB1*0411.hla = 25
DRB1*0406.hla + DRB1*0412.hla = 25
DRB1*0406.hla + DRB1*0413.hla = 26
DRB1*0406.hla + DRB1*0414.hla = 53
DRB1*0406.hla + DRB1*0415.hla = 26

- 98 -

Appendix 1 (cont'd)

DRB1*0406.hla + DRB1*0416.hla = 53
DRB1*0406.hla + DRB1*0417.hla = 52
DRB1*0406.hla + DRB1*0418.hla = 26
DRB1*0406.hla + DRB1*0419.hla = 53
DRB1*0406.hla + DRB1*0420.hla = 53
DRB1*0406.hla + DRB1*0421.hla = 53
DRB1*0406.hla + DRB1*0422.hla = 26
DRB1*0407.hla + DRB1*0408.hla = 17
DRB1*0407.hla + DRB1*0409.hla = 15
DRB1*0407.hla + DRB1*0410.hla = 52
DRB1*0407.hla + DRB1*0411.hla = 52
DRB1*0407.hla + DRB1*0412.hla = 52
DRB1*0407.hla + DRB1*0413.hla = 53
DRB1*0407.hla + DRB1*0414.hla = 17
DRB1*0407.hla + DRB1*0415.hla = 53
DRB1*0407.hla + DRB1*0416.hla = 17
DRB1*0407.hla + DRB1*0417.hla = 15
DRB1*0407.hla + DRB1*0418.hla = 53
DRB1*0407.hla + DRB1*0419.hla = 17
DRB1*0407.hla + DRB1*0420.hla = 17
DRB1*0407.hla + DRB1*0421.hla = 17
DRB1*0407.hla + DRB1*0422.hla = 53
DRB1*0408.hla + DRB1*0409.hla = 1
DRB1*0408.hla + DRB1*0410.hla = 52
DRB1*0408.hla + DRB1*0411.hla = 52
DRB1*0408.hla + DRB1*0412.hla = 52
DRB1*0408.hla + DRB1*0413.hla = 5
DRB1*0408.hla + DRB1*0414.hla = 0
DRB1*0408.hla + DRB1*0415.hla = 53
DRB1*0408.hla + DRB1*0416.hla = 4
DRB1*0408.hla + DRB1*0417.hla = 6
DRB1*0408.hla + DRB1*0418.hla = 1
DRB1*0408.hla + DRB1*0419.hla = 3
DRB1*0408.hla + DRB1*0420.hla = 4
DRB1*0408.hla + DRB1*0421.hla = 17
DRB1*0408.hla + DRB1*0422.hla = 53
DRB1*0409.hla + DRB1*0410.hla = 52
DRB1*0409.hla + DRB1*0411.hla = 52
DRB1*0409.hla + DRB1*0412.hla = 52
DRB1*0409.hla + DRB1*0413.hla = 1
DRB1*0409.hla + DRB1*0414.hla = 1
DRB1*0409.hla + DRB1*0415.hla = 52
DRB1*0409.hla + DRB1*0416.hla = 6
DRB1*0409.hla + DRB1*0417.hla = 6
DRB1*0409.hla + DRB1*0418.hla = 0
DRB1*0409.hla + DRB1*0419.hla = 1
DRB1*0409.hla + DRB1*0420.hla = 6
DRB1*0409.hla + DRB1*0421.hla = 15
DRB1*0409.hla + DRB1*0422.hla = 52
DRB1*0410.hla + DRB1*0411.hla = 25
DRB1*0410.hla + DRB1*0412.hla = 25
DRB1*0410.hla + DRB1*0413.hla = 25
DRB1*0410.hla + DRB1*0414.hla = 52
DRB1*0410.hla + DRB1*0415.hla = 25
DRB1*0410.hla + DRB1*0416.hla = 52
DRB1*0410.hla + DRB1*0417.hla = 52
DRB1*0410.hla + DRB1*0418.hla = 25
DRB1*0410.hla + DRB1*0419.hla = 52
DRB1*0410.hla + DRB1*0420.hla = 52
DRB1*0410.hla + DRB1*0421.hla = 52
DRB1*0410.hla + DRB1*0422.hla = 25

- 99 -

Appendix 1 (cont'd)

DRB1*0411.hla + DRB1*0412.hla = 25
DRB1*0411.hla + DRB1*0413.hla = 25
DRB1*0411.hla + DRB1*0414.hla = 52
DRB1*0411.hla + DRB1*0415.hla = 25
DRB1*0411.hla + DRB1*0416.hla = 52
DRB1*0411.hla + DRB1*0417.hla = 52
DRB1*0411.hla + DRB1*0418.hla = 25
DRB1*0411.hla + DRB1*0419.hla = 52
DRB1*0411.hla + DRB1*0420.hla = 52
DRB1*0411.hla + DRB1*0421.hla = 52
DRB1*0411.hla + DRB1*0422.hla = 25
DRB1*0412.hla + DRB1*0413.hla = 25
DRB1*0412.hla + DRB1*0414.hla = 52
DRB1*0412.hla + DRB1*0415.hla = 25
DRB1*0412.hla + DRB1*0416.hla = 52
DRB1*0412.hla + DRB1*0417.hla = 52
DRB1*0412.hla + DRB1*0418.hla = 0
DRB1*0412.hla + DRB1*0419.hla = 52
DRB1*0412.hla + DRB1*0420.hla = 52
DRB1*0412.hla + DRB1*0421.hla = 52
DRB1*0412.hla + DRB1*0422.hla = 25
DRB1*0413.hla + DRB1*0414.hla = 5
DRB1*0413.hla + DRB1*0415.hla = 26
DRB1*0413.hla + DRB1*0416.hla = 5
DRB1*0413.hla + DRB1*0417.hla = 1
DRB1*0413.hla + DRB1*0418.hla = 0
DRB1*0413.hla + DRB1*0419.hla = 5
DRB1*0413.hla + DRB1*0420.hla = 5
DRB1*0413.hla + DRB1*0421.hla = 53
DRB1*0413.hla + DRB1*0422.hla = 26
DRB1*0414.hla + DRB1*0415.hla = 53
DRB1*0414.hla + DRB1*0416.hla = 4
DRB1*0414.hla + DRB1*0417.hla = 6
DRB1*0414.hla + DRB1*0418.hla = 1
DRB1*0414.hla + DRB1*0419.hla = 3
DRB1*0414.hla + DRB1*0420.hla = 4
DRB1*0414.hla + DRB1*0421.hla = 17
DRB1*0414.hla + DRB1*0422.hla = 53
DRB1*0415.hla + DRB1*0416.hla = 53
DRB1*0415.hla + DRB1*0417.hla = 52
DRB1*0415.hla + DRB1*0418.hla = 26
DRB1*0415.hla + DRB1*0419.hla = 53
DRB1*0415.hla + DRB1*0420.hla = 53
DRB1*0415.hla + DRB1*0421.hla = 53
DRB1*0415.hla + DRB1*0422.hla = 26
DRB1*0416.hla + DRB1*0417.hla = 6
DRB1*0416.hla + DRB1*0418.hla = 1
DRB1*0416.hla + DRB1*0419.hla = 3
DRB1*0416.hla + DRB1*0420.hla = 4
DRB1*0416.hla + DRB1*0421.hla = 17
DRB1*0416.hla + DRB1*0422.hla = 53
DRB1*0417.hla + DRB1*0418.hla = 0
DRB1*0417.hla + DRB1*0419.hla = 1
DRB1*0417.hla + DRB1*0420.hla = 6
DRB1*0417.hla + DRB1*0421.hla = 15
DRB1*0417.hla + DRB1*0422.hla = 52
DRB1*0418.hla + DRB1*0419.hla = 5
DRB1*0418.hla + DRB1*0420.hla = 1
DRB1*0418.hla + DRB1*0421.hla = 53
DRB1*0418.hla + DRB1*0422.hla = 26
DRB1*0419.hla + DRB1*0420.hla = 3

- 100 -

Appendix 1 (cont'd)

DRB1*0419.hla + DRB1*0421.hla = 17
DRB1*0419.hla + DRB1*0422.hla = 53
DRB1*0420.hla + DRB1*0421.hla = 17
DRB1*0420.hla + DRB1*0422.hla = 53
DRB1*0421.hla + DRB1*0422.hla = 53

Unique Sequences using AC:

DRB1*0401.hla + DRB1*0402.hla = 0
DRB1*0401.hla + DRB1*0403.hla = 3
DRB1*0401.hla + DRB1*0404.hla = 0
DRB1*0401.hla + DRB1*0405.hla = 3
DRB1*0401.hla + DRB1*0406.hla = 3
DRB1*0401.hla + DRB1*0407.hla = 3
DRB1*0401.hla + DRB1*0408.hla = 1
DRB1*0401.hla + DRB1*0409.hla = 0
DRB1*0401.hla + DRB1*0410.hla = 3
DRB1*0401.hla + DRB1*0411.hla = 1
DRB1*0401.hla + DRB1*0412.hla = 3
DRB1*0401.hla + DRB1*0413.hla = 0
DRB1*0401.hla + DRB1*0414.hla = 0
DRB1*0401.hla + DRB1*0415.hla = 1
DRB1*0401.hla + DRB1*0416.hla = 0
DRB1*0401.hla + DRB1*0417.hla = 1
DRB1*0401.hla + DRB1*0418.hla = 3
DRB1*0401.hla + DRB1*0419.hla = 1
DRB1*0401.hla + DRB1*0420.hla = 2
DRB1*0401.hla + DRB1*0421.hla = 0
DRB1*0401.hla + DRB1*0422.hla = 0
DRB1*0402.hla + DRB1*0403.hla = 1
DRB1*0402.hla + DRB1*0404.hla = 0
DRB1*0402.hla + DRB1*0405.hla = 1
DRB1*0402.hla + DRB1*0406.hla = 0
DRB1*0402.hla + DRB1*0407.hla = 1
DRB1*0402.hla + DRB1*0408.hla = 1
DRB1*0402.hla + DRB1*0409.hla = 0
DRB1*0402.hla + DRB1*0410.hla = 1
DRB1*0402.hla + DRB1*0411.hla = 0
DRB1*0402.hla + DRB1*0412.hla = 0
DRB1*0402.hla + DRB1*0413.hla = 0
DRB1*0402.hla + DRB1*0414.hla = 0
DRB1*0402.hla + DRB1*0415.hla = 0
DRB1*0402.hla + DRB1*0416.hla = 0
DRB1*0402.hla + DRB1*0417.hla = 0
DRB1*0402.hla + DRB1*0418.hla = 0
DRB1*0402.hla + DRB1*0419.hla = 0
DRB1*0402.hla + DRB1*0420.hla = 0
DRB1*0402.hla + DRB1*0421.hla = 0
DRB1*0402.hla + DRB1*0422.hla = 0
DRB1*0403.hla + DRB1*0404.hla = 3
DRB1*0403.hla + DRB1*0405.hla = 3
DRB1*0403.hla + DRB1*0406.hla = 1
DRB1*0403.hla + DRB1*0407.hla = 0
DRB1*0403.hla + DRB1*0408.hla = 1
DRB1*0403.hla + DRB1*0409.hla = 1
DRB1*0403.hla + DRB1*0410.hla = 3
DRB1*0403.hla + DRB1*0411.hla = 1
DRB1*0403.hla + DRB1*0412.hla = 3
DRB1*0403.hla + DRB1*0413.hla = 1
DRB1*0403.hla + DRB1*0414.hla = 1
DRB1*0403.hla + DRB1*0415.hla = 1

Appendix 1 (cont'd)

DRB1*0403.hla + DRB1*0416.hla = 1
DRB1*0403.hla + DRB1*0417.hla = 1
DRB1*0403.hla + DRB1*0418.hla = 3
DRB1*0403.hla + DRB1*0419.hla = 2
DRB1*0403.hla + DRB1*0420.hla = 1
DRB1*0403.hla + DRB1*0421.hla = 3
DRB1*0403.hla + DRB1*0422.hla = 2
DRB1*0404.hla + DRB1*0405.hla = 3
DRB1*0404.hla + DRB1*0406.hla = 3
DRB1*0404.hla + DRB1*0407.hla = 3
DRB1*0404.hla + DRB1*0408.hla = 1
DRB1*0404.hla + DRB1*0409.hla = 2
DRB1*0404.hla + DRB1*0410.hla = 3
DRB1*0404.hla + DRB1*0411.hla = 1
DRB1*0404.hla + DRB1*0412.hla = 3
DRB1*0404.hla + DRB1*0413.hla = 0
DRB1*0404.hla + DRB1*0414.hla = 1
DRB1*0404.hla + DRB1*0415.hla = 1
DRB1*0404.hla + DRB1*0416.hla = 0
DRB1*0404.hla + DRB1*0417.hla = 1
DRB1*0404.hla + DRB1*0418.hla = 3
DRB1*0404.hla + DRB1*0419.hla = 1
DRB1*0404.hla + DRB1*0420.hla = 2
DRB1*0404.hla + DRB1*0421.hla = 0
DRB1*0404.hla + DRB1*0422.hla = 2
DRB1*0405.hla + DRB1*0406.hla = 1
DRB1*0405.hla + DRB1*0407.hla = 3
DRB1*0405.hla + DRB1*0408.hla = 2
DRB1*0405.hla + DRB1*0409.hla = 1
DRB1*0405.hla + DRB1*0410.hla = 0
DRB1*0405.hla + DRB1*0411.hla = 1
DRB1*0405.hla + DRB1*0412.hla = 1
DRB1*0405.hla + DRB1*0413.hla = 1
DRB1*0405.hla + DRB1*0414.hla = 1
DRB1*0405.hla + DRB1*0415.hla = 1
DRB1*0405.hla + DRB1*0416.hla = 1
DRB1*0405.hla + DRB1*0417.hla = 1
DRB1*0405.hla + DRB1*0418.hla = 2
DRB1*0405.hla + DRB1*0419.hla = 1
DRB1*0405.hla + DRB1*0420.hla = 2
DRB1*0405.hla + DRB1*0421.hla = 1
DRB1*0405.hla + DRB1*0422.hla = 1
DRB1*0406.hla + DRB1*0407.hla = 1
DRB1*0406.hla + DRB1*0408.hla = 0
DRB1*0406.hla + DRB1*0409.hla = 0
DRB1*0406.hla + DRB1*0410.hla = 1
DRB1*0406.hla + DRB1*0411.hla = 0
DRB1*0406.hla + DRB1*0412.hla = 1
DRB1*0406.hla + DRB1*0413.hla = 2
DRB1*0406.hla + DRB1*0414.hla = 0
DRB1*0406.hla + DRB1*0415.hla = 0
DRB1*0406.hla + DRB1*0416.hla = 2
DRB1*0406.hla + DRB1*0417.hla = 0
DRB1*0406.hla + DRB1*0418.hla = 1
DRB1*0406.hla + DRB1*0419.hla = 0
DRB1*0406.hla + DRB1*0420.hla = 0
DRB1*0406.hla + DRB1*0421.hla = 0
DRB1*0406.hla + DRB1*0422.hla = 0
DRB1*0407.hla + DRB1*0408.hla = 1
DRB1*0407.hla + DRB1*0409.hla = 1
DRB1*0407.hla + DRB1*0410.hla = 3

- 102 -

Appendix 1 (cont'd)

DRB1*0407.hla + DRB1*0411.hla = 1
DRB1*0407.hla + DRB1*0412.hla = 3
DRB1*0407.hla + DRB1*0413.hla = 1
DRB1*0407.hla + DRB1*0414.hla = 1
DRB1*0407.hla + DRB1*0415.hla = 1
DRB1*0407.hla + DRB1*0416.hla = 1
DRB1*0407.hla + DRB1*0417.hla = 1
DRB1*0407.hla + DRB1*0418.hla = 3
DRB1*0407.hla + DRB1*0419.hla = 2
DRB1*0407.hla + DRB1*0420.hla = 1
DRB1*0407.hla + DRB1*0421.hla = 3
DRB1*0407.hla + DRB1*0422.hla = 2
DRB1*0408.hla + DRB1*0409.hla = 0
DRB1*0408.hla + DRB1*0410.hla = 2
DRB1*0408.hla + DRB1*0411.hla = 0
DRB1*0408.hla + DRB1*0412.hla = 2
DRB1*0408.hla + DRB1*0413.hla = 1
DRB1*0408.hla + DRB1*0414.hla = 0
DRB1*0408.hla + DRB1*0415.hla = 0
DRB1*0408.hla + DRB1*0416.hla = 1
DRB1*0408.hla + DRB1*0417.hla = 0
DRB1*0408.hla + DRB1*0418.hla = 2
DRB1*0408.hla + DRB1*0419.hla = 0
DRB1*0408.hla + DRB1*0420.hla = 0
DRB1*0408.hla + DRB1*0421.hla = 0
DRB1*0408.hla + DRB1*0422.hla = 0
DRB1*0409.hla + DRB1*0410.hla = 1
DRB1*0409.hla + DRB1*0411.hla = 0
DRB1*0409.hla + DRB1*0412.hla = 0
DRB1*0409.hla + DRB1*0413.hla = 1
DRB1*0409.hla + DRB1*0414.hla = 0
DRB1*0409.hla + DRB1*0415.hla = 0
DRB1*0409.hla + DRB1*0416.hla = 1
DRB1*0409.hla + DRB1*0417.hla = 0
DRB1*0409.hla + DRB1*0418.hla = 1
DRB1*0409.hla + DRB1*0419.hla = 0
DRB1*0409.hla + DRB1*0420.hla = 0
DRB1*0409.hla + DRB1*0421.hla = 0
DRB1*0409.hla + DRB1*0422.hla = 0
DRB1*0410.hla + DRB1*0411.hla = 1
DRB1*0410.hla + DRB1*0412.hla = 1
DRB1*0410.hla + DRB1*0413.hla = 1
DRB1*0410.hla + DRB1*0414.hla = 1
DRB1*0410.hla + DRB1*0415.hla = 1
DRB1*0410.hla + DRB1*0416.hla = 1
DRB1*0410.hla + DRB1*0417.hla = 1
DRB1*0410.hla + DRB1*0418.hla = 2
DRB1*0410.hla + DRB1*0419.hla = 1
DRB1*0410.hla + DRB1*0420.hla = 2
DRB1*0410.hla + DRB1*0421.hla = 1
DRB1*0410.hla + DRB1*0422.hla = 1
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 0
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 0
DRB1*0411.hla + DRB1*0420.hla = 0
DRB1*0411.hla + DRB1*0421.hla = 0

Appendix 1 (cont'd)

DRB1*0411.hla + DRB1*0422.hla = 0
DRB1*0412.hla + DRB1*0413.hla = 0
DRB1*0412.hla + DRB1*0414.hla = 0
DRB1*0412.hla + DRB1*0415.hla = 0
DRB1*0412.hla + DRB1*0416.hla = 0
DRB1*0412.hla + DRB1*0417.hla = 0
DRB1*0412.hla + DRB1*0418.hla = 0
DRB1*0412.hla + DRB1*0419.hla = 0
DRB1*0412.hla + DRB1*0420.hla = 0
DRB1*0412.hla + DRB1*0421.hla = 1
DRB1*0412.hla + DRB1*0422.hla = 0
DRB1*0413.hla + DRB1*0414.hla = 1
DRB1*0413.hla + DRB1*0415.hla = 0
DRB1*0413.hla + DRB1*0416.hla = 0
DRB1*0413.hla + DRB1*0417.hla = 1
DRB1*0413.hla + DRB1*0418.hla = 2
DRB1*0413.hla + DRB1*0419.hla = 0
DRB1*0413.hla + DRB1*0420.hla = 1
DRB1*0413.hla + DRB1*0421.hla = 0
DRB1*0413.hla + DRB1*0422.hla = 0
DRB1*0414.hla + DRB1*0415.hla = 0
DRB1*0414.hla + DRB1*0416.hla = 1
DRB1*0414.hla + DRB1*0417.hla = 0
DRB1*0414.hla + DRB1*0418.hla = 0
DRB1*0414.hla + DRB1*0419.hla = 0
DRB1*0414.hla + DRB1*0420.hla = 0
DRB1*0414.hla + DRB1*0421.hla = 0
DRB1*0414.hla + DRB1*0422.hla = 0
DRB1*0415.hla + DRB1*0416.hla = 0
DRB1*0415.hla + DRB1*0417.hla = 0
DRB1*0415.hla + DRB1*0418.hla = 0
DRB1*0415.hla + DRB1*0419.hla = 0
DRB1*0415.hla + DRB1*0420.hla = 0
DRB1*0415.hla + DRB1*0421.hla = 0
DRB1*0415.hla + DRB1*0422.hla = 0
DRB1*0416.hla + DRB1*0417.hla = 1
DRB1*0416.hla + DRB1*0418.hla = 2
DRB1*0416.hla + DRB1*0419.hla = 0
DRB1*0416.hla + DRB1*0420.hla = 1
DRB1*0416.hla + DRB1*0421.hla = 0
DRB1*0416.hla + DRB1*0422.hla = 0
DRB1*0417.hla + DRB1*0418.hla = 1
DRB1*0417.hla + DRB1*0419.hla = 0
DRB1*0417.hla + DRB1*0420.hla = 0
DRB1*0417.hla + DRB1*0421.hla = 2
DRB1*0417.hla + DRB1*0422.hla = 0
DRB1*0418.hla + DRB1*0419.hla = 1
DRB1*0418.hla + DRB1*0420.hla = 1
DRB1*0418.hla + DRB1*0421.hla = 1
DRB1*0418.hla + DRB1*0422.hla = 0
DRB1*0419.hla + DRB1*0420.hla = 0
DRB1*0419.hla + DRB1*0421.hla = 0
DRB1*0419.hla + DRB1*0422.hla = 0
DRB1*0420.hla + DRB1*0421.hla = 0
DRB1*0420.hla + DRB1*0422.hla = 0
DRB1*0421.hla + DRB1*0422.hla = 0

Unique Sequences using AG:

DRB1*0401.hla + DRB1*0402.hla = 0
DRB1*0401.hla + DRB1*0403.hla = 1

Appendix 1 (cont'd)

DRB1*0401.hla + DRB1*0404.hla = 1
DRB1*0401.hla + DRB1*0405.hla = 0
DRB1*0401.hla + DRB1*0406.hla = 3
DRB1*0401.hla + DRB1*0407.hla = 0
DRB1*0401.hla + DRB1*0408.hla = 0
DRB1*0401.hla + DRB1*0409.hla = 0
DRB1*0401.hla + DRB1*0410.hla = 0
DRB1*0401.hla + DRB1*0411.hla = 0
DRB1*0401.hla + DRB1*0412.hla = 0
DRB1*0401.hla + DRB1*0413.hla = 0
DRB1*0401.hla + DRB1*0414.hla = 0
DRB1*0401.hla + DRB1*0415.hla = 0
DRB1*0401.hla + DRB1*0416.hla = 0
DRB1*0401.hla + DRB1*0417.hla = 0
DRB1*0401.hla + DRB1*0418.hla = 0
DRB1*0401.hla + DRB1*0419.hla = 3
DRB1*0401.hla + DRB1*0420.hla = 3
DRB1*0401.hla + DRB1*0421.hla = 0
DRB1*0401.hla + DRB1*0422.hla = 0
DRB1*0402.hla + DRB1*0403.hla = 1
DRB1*0402.hla + DRB1*0404.hla = 1
DRB1*0402.hla + DRB1*0405.hla = 0
DRB1*0402.hla + DRB1*0406.hla = 0
DRB1*0402.hla + DRB1*0407.hla = 0
DRB1*0402.hla + DRB1*0408.hla = 2
DRB1*0402.hla + DRB1*0409.hla = 0
DRB1*0402.hla + DRB1*0410.hla = 0
DRB1*0402.hla + DRB1*0411.hla = 0
DRB1*0402.hla + DRB1*0412.hla = 0
DRB1*0402.hla + DRB1*0413.hla = 0
DRB1*0402.hla + DRB1*0414.hla = 0
DRB1*0402.hla + DRB1*0415.hla = 0
DRB1*0402.hla + DRB1*0416.hla = 0
DRB1*0402.hla + DRB1*0417.hla = 0
DRB1*0402.hla + DRB1*0418.hla = 0
DRB1*0402.hla + DRB1*0419.hla = 1
DRB1*0402.hla + DRB1*0420.hla = 1
DRB1*0402.hla + DRB1*0421.hla = 0
DRB1*0402.hla + DRB1*0422.hla = 0
DRB1*0403.hla + DRB1*0404.hla = 0
DRB1*0403.hla + DRB1*0405.hla = 2
DRB1*0403.hla + DRB1*0406.hla = 0
DRB1*0403.hla + DRB1*0407.hla = 0
DRB1*0403.hla + DRB1*0408.hla = 1
DRB1*0403.hla + DRB1*0409.hla = 1
DRB1*0403.hla + DRB1*0410.hla = 1
DRB1*0403.hla + DRB1*0411.hla = 0
DRB1*0403.hla + DRB1*0412.hla = 1
DRB1*0403.hla + DRB1*0413.hla = 1
DRB1*0403.hla + DRB1*0414.hla = 2
DRB1*0403.hla + DRB1*0415.hla = 1
DRB1*0403.hla + DRB1*0416.hla = 1
DRB1*0403.hla + DRB1*0417.hla = 0
DRB1*0403.hla + DRB1*0418.hla = 1
DRB1*0403.hla + DRB1*0419.hla = 3
DRB1*0403.hla + DRB1*0420.hla = 1
DRB1*0403.hla + DRB1*0421.hla = 3
DRB1*0403.hla + DRB1*0422.hla = 0
DRB1*0404.hla + DRB1*0405.hla = 2
DRB1*0404.hla + DRB1*0406.hla = 0
DRB1*0404.hla + DRB1*0407.hla = 0

Appendix 1 (cont'd)

DRB1*0404.hla + DRB1*0408.hla = 1
DRB1*0404.hla + DRB1*0409.hla = 1
DRB1*0404.hla + DRB1*0410.hla = 1
DRB1*0404.hla + DRB1*0411.hla = 0
DRB1*0404.hla + DRB1*0412.hla = 1
DRB1*0404.hla + DRB1*0413.hla = 1
DRB1*0404.hla + DRB1*0414.hla = 2
DRB1*0404.hla + DRB1*0415.hla = 1
DRB1*0404.hla + DRB1*0416.hla = 1
DRB1*0404.hla + DRB1*0417.hla = 0
DRB1*0404.hla + DRB1*0418.hla = 1
DRB1*0404.hla + DRB1*0419.hla = 3
DRB1*0404.hla + DRB1*0420.hla = 3
DRB1*0404.hla + DRB1*0421.hla = 3
DRB1*0404.hla + DRB1*0422.hla = 0
DRB1*0405.hla + DRB1*0406.hla = 0
DRB1*0405.hla + DRB1*0407.hla = 0
DRB1*0405.hla + DRB1*0408.hla = 0
DRB1*0405.hla + DRB1*0409.hla = 0
DRB1*0405.hla + DRB1*0410.hla = 0
DRB1*0405.hla + DRB1*0411.hla = 0
DRB1*0405.hla + DRB1*0412.hla = 0
DRB1*0405.hla + DRB1*0413.hla = 0
DRB1*0405.hla + DRB1*0414.hla = 0
DRB1*0405.hla + DRB1*0415.hla = 0
DRB1*0405.hla + DRB1*0416.hla = 0
DRB1*0405.hla + DRB1*0417.hla = 0
DRB1*0405.hla + DRB1*0418.hla = 0
DRB1*0405.hla + DRB1*0419.hla = 1
DRB1*0405.hla + DRB1*0420.hla = 1
DRB1*0405.hla + DRB1*0421.hla = 0
DRB1*0405.hla + DRB1*0422.hla = 0
DRB1*0406.hla + DRB1*0407.hla = 0
DRB1*0406.hla + DRB1*0408.hla = 0
DRB1*0406.hla + DRB1*0409.hla = 0
DRB1*0406.hla + DRB1*0410.hla = 0
DRB1*0406.hla + DRB1*0411.hla = 0
DRB1*0406.hla + DRB1*0412.hla = 0
DRB1*0406.hla + DRB1*0413.hla = 0
DRB1*0406.hla + DRB1*0414.hla = 0
DRB1*0406.hla + DRB1*0415.hla = 0
DRB1*0406.hla + DRB1*0416.hla = 0
DRB1*0406.hla + DRB1*0417.hla = 0
DRB1*0406.hla + DRB1*0418.hla = 0
DRB1*0406.hla + DRB1*0419.hla = 3
DRB1*0406.hla + DRB1*0420.hla = 1
DRB1*0406.hla + DRB1*0421.hla = 3
DRB1*0406.hla + DRB1*0422.hla = 0
DRB1*0407.hla + DRB1*0408.hla = 0
DRB1*0407.hla + DRB1*0409.hla = 0
DRB1*0407.hla + DRB1*0410.hla = 2
DRB1*0407.hla + DRB1*0411.hla = 0
DRB1*0407.hla + DRB1*0412.hla = 0
DRB1*0407.hla + DRB1*0413.hla = 0
DRB1*0407.hla + DRB1*0414.hla = 0
DRB1*0407.hla + DRB1*0415.hla = 0
DRB1*0407.hla + DRB1*0416.hla = 0
DRB1*0407.hla + DRB1*0417.hla = 0
DRB1*0407.hla + DRB1*0418.hla = 0
DRB1*0407.hla + DRB1*0419.hla = 0
DRB1*0407.hla + DRB1*0420.hla = 0

Appendix 1 (cont'd)

DRB1*0407.hla + DRB1*0421.hla = 0
DRB1*0407.hla + DRB1*0422.hla = 0
DRB1*0408.hla + DRB1*0409.hla = 0
DRB1*0408.hla + DRB1*0410.hla = 0
DRB1*0408.hla + DRB1*0411.hla = 0
DRB1*0408.hla + DRB1*0412.hla = 0
DRB1*0408.hla + DRB1*0413.hla = 0
DRB1*0408.hla + DRB1*0414.hla = 0
DRB1*0408.hla + DRB1*0415.hla = 0
DRB1*0408.hla + DRB1*0416.hla = 0
DRB1*0408.hla + DRB1*0417.hla = 0
DRB1*0408.hla + DRB1*0418.hla = 0
DRB1*0408.hla + DRB1*0419.hla = 1
DRB1*0408.hla + DRB1*0420.hla = 1
DRB1*0408.hla + DRB1*0421.hla = 0
DRB1*0408.hla + DRB1*0422.hla = 0
DRB1*0409.hla + DRB1*0410.hla = 0
DRB1*0409.hla + DRB1*0411.hla = 0
DRB1*0409.hla + DRB1*0412.hla = 0
DRB1*0409.hla + DRB1*0413.hla = 0
DRB1*0409.hla + DRB1*0414.hla = 0
DRB1*0409.hla + DRB1*0415.hla = 0
DRB1*0409.hla + DRB1*0416.hla = 0
DRB1*0409.hla + DRB1*0417.hla = 0
DRB1*0409.hla + DRB1*0418.hla = 0
DRB1*0409.hla + DRB1*0419.hla = 1
DRB1*0409.hla + DRB1*0420.hla = 1
DRB1*0409.hla + DRB1*0421.hla = 0
DRB1*0409.hla + DRB1*0422.hla = 0
DRB1*0410.hla + DRB1*0411.hla = 0
DRB1*0410.hla + DRB1*0412.hla = 0
DRB1*0410.hla + DRB1*0413.hla = 0
DRB1*0410.hla + DRB1*0414.hla = 0
DRB1*0410.hla + DRB1*0415.hla = 0
DRB1*0410.hla + DRB1*0416.hla = 0
DRB1*0410.hla + DRB1*0417.hla = 0
DRB1*0410.hla + DRB1*0418.hla = 0
DRB1*0410.hla + DRB1*0419.hla = 1
DRB1*0410.hla + DRB1*0420.hla = 1
DRB1*0410.hla + DRB1*0421.hla = 0
DRB1*0410.hla + DRB1*0422.hla = 0
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 0
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 0
DRB1*0411.hla + DRB1*0420.hla = 0
DRB1*0411.hla + DRB1*0421.hla = 0
DRB1*0411.hla + DRB1*0422.hla = 0
DRB1*0412.hla + DRB1*0413.hla = 0
DRB1*0412.hla + DRB1*0414.hla = 0
DRB1*0412.hla + DRB1*0415.hla = 0
DRB1*0412.hla + DRB1*0416.hla = 0
DRB1*0412.hla + DRB1*0417.hla = 0
DRB1*0412.hla + DRB1*0418.hla = 0
DRB1*0412.hla + DRB1*0419.hla = 1
DRB1*0412.hla + DRB1*0420.hla = 1
DRB1*0412.hla + DRB1*0421.hla = 0

Appendix 1 (cont'd)

DRB1*0412.hla + DRB1*0422.hla = 0
DRB1*0413.hla + DRB1*0414.hla = 0
DRB1*0413.hla + DRB1*0415.hla = 0
DRB1*0413.hla + DRB1*0416.hla = 0
DRB1*0413.hla + DRB1*0417.hla = 0
DRB1*0413.hla + DRB1*0418.hla = 0
DRB1*0413.hla + DRB1*0419.hla = 1
DRB1*0413.hla + DRB1*0420.hla = 1
DRB1*0413.hla + DRB1*0421.hla = 0
DRB1*0413.hla + DRB1*0422.hla = 0
DRB1*0414.hla + DRB1*0415.hla = 0
DRB1*0414.hla + DRB1*0416.hla = 0
DRB1*0414.hla + DRB1*0417.hla = 0
DRB1*0414.hla + DRB1*0418.hla = 0
DRB1*0414.hla + DRB1*0419.hla = 1
DRB1*0414.hla + DRB1*0420.hla = 1
DRB1*0414.hla + DRB1*0421.hla = 0
DRB1*0414.hla + DRB1*0422.hla = 0
DRB1*0415.hla + DRB1*0416.hla = 0
DRB1*0415.hla + DRB1*0417.hla = 0
DRB1*0415.hla + DRB1*0418.hla = 0
DRB1*0415.hla + DRB1*0419.hla = 1
DRB1*0415.hla + DRB1*0420.hla = 1
DRB1*0415.hla + DRB1*0421.hla = 0
DRB1*0415.hla + DRB1*0422.hla = 0
DRB1*0416.hla + DRB1*0417.hla = 0
DRB1*0416.hla + DRB1*0418.hla = 0
DRB1*0416.hla + DRB1*0419.hla = 1
DRB1*0416.hla + DRB1*0420.hla = 1
DRB1*0416.hla + DRB1*0421.hla = 0
DRB1*0416.hla + DRB1*0422.hla = 0
DRB1*0417.hla + DRB1*0418.hla = 0
DRB1*0417.hla + DRB1*0419.hla = 0
DRB1*0417.hla + DRB1*0420.hla = 0
DRB1*0417.hla + DRB1*0421.hla = 0
DRB1*0417.hla + DRB1*0422.hla = 0
DRB1*0418.hla + DRB1*0419.hla = 1
DRB1*0418.hla + DRB1*0420.hla = 1
DRB1*0418.hla + DRB1*0421.hla = 0
DRB1*0418.hla + DRB1*0422.hla = 0
DRB1*0419.hla + DRB1*0420.hla = 0
DRB1*0419.hla + DRB1*0421.hla = 3
DRB1*0419.hla + DRB1*0422.hla = 0
DRB1*0420.hla + DRB1*0421.hla = 3
DRB1*0420.hla + DRB1*0422.hla = 0
DRB1*0421.hla + DRB1*0422.hla = 0

Unique Sequences using AT:

DRB1*0401.hla + DRB1*0402.hla = 0
DRB1*0401.hla + DRB1*0403.hla = 5
DRB1*0401.hla + DRB1*0404.hla = 5
DRB1*0401.hla + DRB1*0405.hla = 1
DRB1*0401.hla + DRB1*0406.hla = 4
DRB1*0401.hla + DRB1*0407.hla = 0
DRB1*0401.hla + DRB1*0408.hla = 1
DRB1*0401.hla + DRB1*0409.hla = 0
DRB1*0401.hla + DRB1*0410.hla = 6
DRB1*0401.hla + DRB1*0411.hla = 0
DRB1*0401.hla + DRB1*0412.hla = 6
DRB1*0401.hla + DRB1*0413.hla = 1

- 108 -

Appendix 1 (cont'd)

DRB1*0401.hla + DRB1*0414.hla = 0
DRB1*0401.hla + DRB1*0415.hla = 5
DRB1*0401.hla + DRB1*0416.hla = 0
DRB1*0401.hla + DRB1*0417.hla = 1
DRB1*0401.hla + DRB1*0418.hla = 4
DRB1*0401.hla + DRB1*0419.hla = 4
DRB1*0401.hla + DRB1*0420.hla = 4
DRB1*0401.hla + DRB1*0421.hla = 0
DRB1*0401.hla + DRB1*0422.hla = 0
DRB1*0402.hla + DRB1*0403.hla = 1
DRB1*0402.hla + DRB1*0404.hla = 1
DRB1*0402.hla + DRB1*0405.hla = 0
DRB1*0402.hla + DRB1*0406.hla = 0
DRB1*0402.hla + DRB1*0407.hla = 0
DRB1*0402.hla + DRB1*0408.hla = 2
DRB1*0402.hla + DRB1*0409.hla = 0
DRB1*0402.hla + DRB1*0410.hla = 0
DRB1*0402.hla + DRB1*0411.hla = 0
DRB1*0402.hla + DRB1*0412.hla = 0
DRB1*0402.hla + DRB1*0413.hla = 0
DRB1*0402.hla + DRB1*0414.hla = 0
DRB1*0402.hla + DRB1*0415.hla = 0
DRB1*0402.hla + DRB1*0416.hla = 0
DRB1*0402.hla + DRB1*0417.hla = 0
DRB1*0402.hla + DRB1*0418.hla = 0
DRB1*0402.hla + DRB1*0419.hla = 1
DRB1*0402.hla + DRB1*0420.hla = 1
DRB1*0402.hla + DRB1*0421.hla = 0
DRB1*0402.hla + DRB1*0422.hla = 0
DRB1*0403.hla + DRB1*0404.hla = 5
DRB1*0403.hla + DRB1*0405.hla = 6
DRB1*0403.hla + DRB1*0406.hla = 0
DRB1*0403.hla + DRB1*0407.hla = 0
DRB1*0403.hla + DRB1*0408.hla = 4
DRB1*0403.hla + DRB1*0409.hla = 5
DRB1*0403.hla + DRB1*0410.hla = 5
DRB1*0403.hla + DRB1*0411.hla = 0
DRB1*0403.hla + DRB1*0412.hla = 0
DRB1*0403.hla + DRB1*0413.hla = 2
DRB1*0403.hla + DRB1*0414.hla = 2
DRB1*0403.hla + DRB1*0415.hla = 5
DRB1*0403.hla + DRB1*0416.hla = 3
DRB1*0403.hla + DRB1*0417.hla = 0
DRB1*0403.hla + DRB1*0418.hla = 0
DRB1*0403.hla + DRB1*0419.hla = 8
DRB1*0403.hla + DRB1*0420.hla = 1
DRB1*0403.hla + DRB1*0421.hla = 4
DRB1*0403.hla + DRB1*0422.hla = 5
DRB1*0404.hla + DRB1*0405.hla = 6
DRB1*0404.hla + DRB1*0406.hla = 2
DRB1*0404.hla + DRB1*0407.hla = 5
DRB1*0404.hla + DRB1*0408.hla = 4
DRB1*0404.hla + DRB1*0409.hla = 5
DRB1*0404.hla + DRB1*0410.hla = 5
DRB1*0404.hla + DRB1*0411.hla = 2
DRB1*0404.hla + DRB1*0412.hla = 5
DRB1*0404.hla + DRB1*0413.hla = 2
DRB1*0404.hla + DRB1*0414.hla = 2
DRB1*0404.hla + DRB1*0415.hla = 5
DRB1*0404.hla + DRB1*0416.hla = 3
DRB1*0404.hla + DRB1*0417.hla = 5

Appendix 1 (cont'd)

```
DRB1*0404.hla + DRB1*0418.hla = 1
DRB1*0404.hla + DRB1*0419.hla = 8
DRB1*0404.hla + DRB1*0420.hla = 8
DRB1*0404.hla + DRB1*0421.hla = 4
DRB1*0404.hla + DRB1*0422.hla = 5
DRB1*0405.hla + DRB1*0406.hla = 2
DRB1*0405.hla + DRB1*0407.hla = 1
DRB1*0405.hla + DRB1*0408.hla = 1
DRB1*0405.hla + DRB1*0409.hla = 0
DRB1*0405.hla + DRB1*0410.hla = 1
DRB1*0405.hla + DRB1*0411.hla = 0
DRB1*0405.hla + DRB1*0412.hla = 1
DRB1*0405.hla + DRB1*0413.hla = 5
DRB1*0405.hla + DRB1*0414.hla = 0
DRB1*0405.hla + DRB1*0415.hla = 6
DRB1*0405.hla + DRB1*0416.hla = 1
DRB1*0405.hla + DRB1*0417.hla = 0
DRB1*0405.hla + DRB1*0418.hla = 5
DRB1*0405.hla + DRB1*0419.hla = 2
DRB1*0405.hla + DRB1*0420.hla = 2
DRB1*0405.hla + DRB1*0421.hla = 0
DRB1*0405.hla + DRB1*0422.hla = 6
DRB1*0406.hla + DRB1*0407.hla = 0
DRB1*0406.hla + DRB1*0408.hla = 1
DRB1*0406.hla + DRB1*0409.hla = 0
DRB1*0406.hla + DRB1*0410.hla = 0
DRB1*0406.hla + DRB1*0411.hla = 0
DRB1*0406.hla + DRB1*0412.hla = 0
DRB1*0406.hla + DRB1*0413.hla = 0
DRB1*0406.hla + DRB1*0414.hla = 0
DRB1*0406.hla + DRB1*0415.hla = 2
DRB1*0406.hla + DRB1*0416.hla = 8
DRB1*0406.hla + DRB1*0417.hla = 0
DRB1*0406.hla + DRB1*0418.hla = 0
DRB1*0406.hla + DRB1*0419.hla = 8
DRB1*0406.hla + DRB1*0420.hla = 1
DRB1*0406.hla + DRB1*0421.hla = 4
DRB1*0406.hla + DRB1*0422.hla = 2
DRB1*0407.hla + DRB1*0408.hla = 1
DRB1*0407.hla + DRB1*0409.hla = 1
DRB1*0407.hla + DRB1*0410.hla = 6
DRB1*0407.hla + DRB1*0411.hla = 0
DRB1*0407.hla + DRB1*0412.hla = 0
DRB1*0407.hla + DRB1*0413.hla = 3
DRB1*0407.hla + DRB1*0414.hla = 0
DRB1*0407.hla + DRB1*0415.hla = 5
DRB1*0407.hla + DRB1*0416.hla = 0
DRB1*0407.hla + DRB1*0417.hla = 0
DRB1*0407.hla + DRB1*0418.hla = 0
DRB1*0407.hla + DRB1*0419.hla = 4
DRB1*0407.hla + DRB1*0420.hla = 0
DRB1*0407.hla + DRB1*0421.hla = 0
DRB1*0407.hla + DRB1*0422.hla = 5
DRB1*0408.hla + DRB1*0409.hla = 0
DRB1*0408.hla + DRB1*0410.hla = 5
DRB1*0408.hla + DRB1*0411.hla = 0
DRB1*0408.hla + DRB1*0412.hla = 5
DRB1*0408.hla + DRB1*0413.hla = 0
DRB1*0408.hla + DRB1*0414.hla = 0
DRB1*0408.hla + DRB1*0415.hla = 4
DRB1*0408.hla + DRB1*0416.hla = 0
```

Appendix 1 (cont'd)

DRB1*0408.hla + DRB1*0417.hla = 0
DRB1*0408.hla + DRB1*0418.hla = 0
DRB1*0408.hla + DRB1*0419.hla = 0
DRB1*0408.hla + DRB1*0420.hla = 0
DRB1*0408.hla + DRB1*0421.hla = 0
DRB1*0408.hla + DRB1*0422.hla = 4
DRB1*0409.hla + DRB1*0410.hla = 1
DRB1*0409.hla + DRB1*0411.hla = 0
DRB1*0409.hla + DRB1*0412.hla = 1
DRB1*0409.hla + DRB1*0413.hla = 0
DRB1*0409.hla + DRB1*0414.hla = 0
DRB1*0409.hla + DRB1*0415.hla = 5
DRB1*0409.hla + DRB1*0416.hla = 0
DRB1*0409.hla + DRB1*0417.hla = 0
DRB1*0409.hla + DRB1*0418.hla = 0
DRB1*0409.hla + DRB1*0419.hla = 0
DRB1*0409.hla + DRB1*0420.hla = 0
DRB1*0409.hla + DRB1*0421.hla = 0
DRB1*0409.hla + DRB1*0422.hla = 0
DRB1*0410.hla + DRB1*0411.hla = 0
DRB1*0410.hla + DRB1*0412.hla = 0
DRB1*0410.hla + DRB1*0413.hla = 1
DRB1*0410.hla + DRB1*0414.hla = 0
DRB1*0410.hla + DRB1*0415.hla = 5
DRB1*0410.hla + DRB1*0416.hla = 5
DRB1*0410.hla + DRB1*0417.hla = 0
DRB1*0410.hla + DRB1*0418.hla = 0
DRB1*0410.hla + DRB1*0419.hla = 2
DRB1*0410.hla + DRB1*0420.hla = 2
DRB1*0410.hla + DRB1*0421.hla = 2
DRB1*0410.hla + DRB1*0422.hla = 5
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 2
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 0
DRB1*0411.hla + DRB1*0420.hla = 0
DRB1*0411.hla + DRB1*0421.hla = 0
DRB1*0411.hla + DRB1*0422.hla = 2
DRB1*0412.hla + DRB1*0413.hla = 1
DRB1*0412.hla + DRB1*0414.hla = 0
DRB1*0412.hla + DRB1*0415.hla = 0
DRB1*0412.hla + DRB1*0416.hla = 5
DRB1*0412.hla + DRB1*0417.hla = 0
DRB1*0412.hla + DRB1*0418.hla = 0
DRB1*0412.hla + DRB1*0419.hla = 2
DRB1*0412.hla + DRB1*0420.hla = 0
DRB1*0412.hla + DRB1*0421.hla = 2
DRB1*0412.hla + DRB1*0422.hla = 5
DRB1*0413.hla + DRB1*0414.hla = 0
DRB1*0413.hla + DRB1*0415.hla = 2
DRB1*0413.hla + DRB1*0416.hla = 0
DRB1*0413.hla + DRB1*0417.hla = 0
DRB1*0413.hla + DRB1*0418.hla = 0
DRB1*0413.hla + DRB1*0419.hla = 1
DRB1*0413.hla + DRB1*0420.hla = 1
DRB1*0413.hla + DRB1*0421.hla = 0
DRB1*0413.hla + DRB1*0422.hla = 0

Appendix 1 (cont'd)

DRB1*0414.hla + DRB1*0415.hla = 0
DRB1*0414.hla + DRB1*0416.hla = 0
DRB1*0414.hla + DRB1*0417.hla = 0
DRB1*0414.hla + DRB1*0418.hla = 0
DRB1*0414.hla + DRB1*0419.hla = 0
DRB1*0414.hla + DRB1*0420.hla = 0
DRB1*0414.hla + DRB1*0421.hla = 0
DRB1*0414.hla + DRB1*0422.hla = 0
DRB1*0415.hla + DRB1*0416.hla = 3
DRB1*0415.hla + DRB1*0417.hla = 5
DRB1*0415.hla + DRB1*0418.hla = 0
DRB1*0415.hla + DRB1*0419.hla = 8
DRB1*0415.hla + DRB1*0420.hla = 8
DRB1*0415.hla + DRB1*0421.hla = 4
DRB1*0415.hla + DRB1*0422.hla = 5
DRB1*0416.hla + DRB1*0417.hla = 0
DRB1*0416.hla + DRB1*0418.hla = 0
DRB1*0416.hla + DRB1*0419.hla = 1
DRB1*0416.hla + DRB1*0420.hla = 0
DRB1*0416.hla + DRB1*0421.hla = 0
DRB1*0416.hla + DRB1*0422.hla = 1
DRB1*0417.hla + DRB1*0418.hla = 0
DRB1*0417.hla + DRB1*0419.hla = 0
DRB1*0417.hla + DRB1*0420.hla = 0
DRB1*0417.hla + DRB1*0421.hla = 2
DRB1*0417.hla + DRB1*0422.hla = 5
DRB1*0418.hla + DRB1*0419.hla = 0
DRB1*0418.hla + DRB1*0420.hla = 0
DRB1*0418.hla + DRB1*0421.hla = 1
DRB1*0418.hla + DRB1*0422.hla = 1
DRB1*0419.hla + DRB1*0420.hla = 1
DRB1*0419.hla + DRB1*0421.hla = 4
DRB1*0419.hla + DRB1*0422.hla = 8
DRB1*0420.hla + DRB1*0421.hla = 4
DRB1*0420.hla + DRB1*0422.hla = 8
DRB1*0421.hla + DRB1*0422.hla = 0

Unique Sequences using CG:

DRB1*0401.hla + DRB1*0402.hla = 1
DRB1*0401.hla + DRB1*0403.hla = 2
DRB1*0401.hla + DRB1*0404.hla = 1
DRB1*0401.hla + DRB1*0405.hla = 1
DRB1*0401.hla + DRB1*0406.hla = 2
DRB1*0401.hla + DRB1*0407.hla = 1
DRB1*0401.hla + DRB1*0408.hla = 1
DRB1*0401.hla + DRB1*0409.hla = 1
DRB1*0401.hla + DRB1*0410.hla = 1
DRB1*0401.hla + DRB1*0411.hla = 1
DRB1*0401.hla + DRB1*0412.hla = 1
DRB1*0401.hla + DRB1*0413.hla = 1
DRB1*0401.hla + DRB1*0414.hla = 1
DRB1*0401.hla + DRB1*0415.hla = 1
DRB1*0401.hla + DRB1*0416.hla = 1
DRB1*0401.hla + DRB1*0417.hla = 2
DRB1*0401.hla + DRB1*0418.hla = 1
DRB1*0401.hla + DRB1*0419.hla = 0
DRB1*0401.hla + DRB1*0420.hla = 0
DRB1*0401.hla + DRB1*0421.hla = 0
DRB1*0401.hla + DRB1*0422.hla = 1
DRB1*0402.hla + DRB1*0403.hla = 1

Appendix 1 (cont'd)

DRB1*0402.hla + DRB1*0404.hla = 0
DRB1*0402.hla + DRB1*0405.hla = 0
DRB1*0402.hla + DRB1*0406.hla = 1
DRB1*0402.hla + DRB1*0407.hla = 0
DRB1*0402.hla + DRB1*0408.hla = 1
DRB1*0402.hla + DRB1*0409.hla = 1
DRB1*0402.hla + DRB1*0410.hla = 0
DRB1*0402.hla + DRB1*0411.hla = 0
DRB1*0402.hla + DRB1*0412.hla = 0
DRB1*0402.hla + DRB1*0413.hla = 0
DRB1*0402.hla + DRB1*0414.hla = 0
DRB1*0402.hla + DRB1*0415.hla = 0
DRB1*0402.hla + DRB1*0416.hla = 0
DRB1*0402.hla + DRB1*0417.hla = 0
DRB1*0402.hla + DRB1*0418.hla = 0
DRB1*0402.hla + DRB1*0419.hla = 0
DRB1*0402.hla + DRB1*0420.hla = 2
DRB1*0402.hla + DRB1*0421.hla = 1
DRB1*0402.hla + DRB1*0422.hla = 0
DRB1*0403.hla + DRB1*0404.hla = 2
DRB1*0403.hla + DRB1*0405.hla = 2
DRB1*0403.hla + DRB1*0406.hla = 2
DRB1*0403.hla + DRB1*0407.hla = 2
DRB1*0403.hla + DRB1*0408.hla = 3
DRB1*0403.hla + DRB1*0409.hla = 1
DRB1*0403.hla + DRB1*0410.hla = 1
DRB1*0403.hla + DRB1*0411.hla = 2
DRB1*0403.hla + DRB1*0412.hla = 2
DRB1*0403.hla + DRB1*0413.hla = 1
DRB1*0403.hla + DRB1*0414.hla = 2
DRB1*0403.hla + DRB1*0415.hla = 1
DRB1*0403.hla + DRB1*0416.hla = 1
DRB1*0403.hla + DRB1*0417.hla = 3
DRB1*0403.hla + DRB1*0418.hla = 2
DRB1*0403.hla + DRB1*0419.hla = 0
DRB1*0403.hla + DRB1*0420.hla = 3
DRB1*0403.hla + DRB1*0421.hla = 2
DRB1*0403.hla + DRB1*0422.hla = 1
DRB1*0404.hla + DRB1*0405.hla = 0
DRB1*0404.hla + DRB1*0406.hla = 2
DRB1*0404.hla + DRB1*0407.hla = 2
DRB1*0404.hla + DRB1*0408.hla = 0
DRB1*0404.hla + DRB1*0409.hla = 0
DRB1*0404.hla + DRB1*0410.hla = 0
DRB1*0404.hla + DRB1*0411.hla = 2
DRB1*0404.hla + DRB1*0412.hla = 2
DRB1*0404.hla + DRB1*0413.hla = 0
DRB1*0404.hla + DRB1*0414.hla = 1
DRB1*0404.hla + DRB1*0415.hla = 0
DRB1*0404.hla + DRB1*0416.hla = 0
DRB1*0404.hla + DRB1*0417.hla = 3
DRB1*0404.hla + DRB1*0418.hla = 2
DRB1*0404.hla + DRB1*0419.hla = 0
DRB1*0404.hla + DRB1*0420.hla = 3
DRB1*0404.hla + DRB1*0421.hla = 1
DRB1*0404.hla + DRB1*0422.hla = 0
DRB1*0405.hla + DRB1*0406.hla = 2
DRB1*0405.hla + DRB1*0407.hla = 0
DRB1*0405.hla + DRB1*0408.hla = 0
DRB1*0405.hla + DRB1*0409.hla = 0
DRB1*0405.hla + DRB1*0410.hla = 0

Appendix 1 (cont'd)

DRB1*0405.hla + DRB1*0411.hla = 0
DRB1*0405.hla + DRB1*0412.hla = 0
DRB1*0405.hla + DRB1*0413.hla = 0
DRB1*0405.hla + DRB1*0414.hla = 0
DRB1*0405.hla + DRB1*0415.hla = 0
DRB1*0405.hla + DRB1*0416.hla = 0
DRB1*0405.hla + DRB1*0417.hla = 0
DRB1*0405.hla + DRB1*0418.hla = 0
DRB1*0405.hla + DRB1*0419.hla = 0
DRB1*0405.hla + DRB1*0420.hla = 1
DRB1*0405.hla + DRB1*0421.hla = 1
DRB1*0405.hla + DRB1*0422.hla = 0
DRB1*0406.hla + DRB1*0407.hla = 2
DRB1*0406.hla + DRB1*0408.hla = 3
DRB1*0406.hla + DRB1*0409.hla = 1
DRB1*0406.hla + DRB1*0410.hla = 1
DRB1*0406.hla + DRB1*0411.hla = 2
DRB1*0406.hla + DRB1*0412.hla = 2
DRB1*0406.hla + DRB1*0413.hla = 1
DRB1*0406.hla + DRB1*0414.hla = 2
DRB1*0406.hla + DRB1*0415.hla = 1
DRB1*0406.hla + DRB1*0416.hla = 1
DRB1*0406.hla + DRB1*0417.hla = 3
DRB1*0406.hla + DRB1*0418.hla = 2
DRB1*0406.hla + DRB1*0419.hla = 0
DRB1*0406.hla + DRB1*0420.hla = 0
DRB1*0406.hla + DRB1*0421.hla = 0
DRB1*0406.hla + DRB1*0422.hla = 1
DRB1*0407.hla + DRB1*0408.hla = 1
DRB1*0407.hla + DRB1*0409.hla = 2
DRB1*0407.hla + DRB1*0410.hla = 2
DRB1*0407.hla + DRB1*0411.hla = 0
DRB1*0407.hla + DRB1*0412.hla = 0
DRB1*0407.hla + DRB1*0413.hla = 0
DRB1*0407.hla + DRB1*0414.hla = 0
DRB1*0407.hla + DRB1*0415.hla = 0
DRB1*0407.hla + DRB1*0416.hla = 0
DRB1*0407.hla + DRB1*0417.hla = 1
DRB1*0407.hla + DRB1*0418.hla = 0
DRB1*0407.hla + DRB1*0419.hla = 0
DRB1*0407.hla + DRB1*0420.hla = 1
DRB1*0407.hla + DRB1*0421.hla = 1
DRB1*0407.hla + DRB1*0422.hla = 0
DRB1*0408.hla + DRB1*0409.hla = 1
DRB1*0408.hla + DRB1*0410.hla = 0
DRB1*0408.hla + DRB1*0411.hla = 1
DRB1*0408.hla + DRB1*0412.hla = 1
DRB1*0408.hla + DRB1*0413.hla = 0
DRB1*0408.hla + DRB1*0414.hla = 1
DRB1*0408.hla + DRB1*0415.hla = 0
DRB1*0408.hla + DRB1*0416.hla = 1
DRB1*0408.hla + DRB1*0417.hla = 2
DRB1*0408.hla + DRB1*0418.hla = 2
DRB1*0408.hla + DRB1*0419.hla = 0
DRB1*0408.hla + DRB1*0420.hla = 0
DRB1*0408.hla + DRB1*0421.hla = 1
DRB1*0408.hla + DRB1*0422.hla = 0
DRB1*0409.hla + DRB1*0410.hla = 0
DRB1*0409.hla + DRB1*0411.hla = 0
DRB1*0409.hla + DRB1*0412.hla = 0
DRB1*0409.hla + DRB1*0413.hla = 0

- 114 -

Appendix 1 (cont'd)

```
DRB1*0409.hla + DRB1*0414.hla = 0
DRB1*0409.hla + DRB1*0415.hla = 0
DRB1*0409.hla + DRB1*0416.hla = 0
DRB1*0409.hla + DRB1*0417.hla = 0
DRB1*0409.hla + DRB1*0418.hla = 0
DRB1*0409.hla + DRB1*0419.hla = 1
DRB1*0409.hla + DRB1*0420.hla = 0
DRB1*0409.hla + DRB1*0421.hla = 1
DRB1*0409.hla + DRB1*0422.hla = 0
DRB1*0410.hla + DRB1*0411.hla = 0
DRB1*0410.hla + DRB1*0412.hla = 0
DRB1*0410.hla + DRB1*0413.hla = 0
DRB1*0410.hla + DRB1*0414.hla = 1
DRB1*0410.hla + DRB1*0415.hla = 0
DRB1*0410.hla + DRB1*0416.hla = 0
DRB1*0410.hla + DRB1*0417.hla = 0
DRB1*0410.hla + DRB1*0418.hla = 0
DRB1*0410.hla + DRB1*0419.hla = 0
DRB1*0410.hla + DRB1*0420.hla = 3
DRB1*0410.hla + DRB1*0421.hla = 1
DRB1*0410.hla + DRB1*0422.hla = 0
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 0
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 0
DRB1*0411.hla + DRB1*0420.hla = 1
DRB1*0411.hla + DRB1*0421.hla = 1
DRB1*0411.hla + DRB1*0422.hla = 0
DRB1*0412.hla + DRB1*0413.hla = 0
DRB1*0412.hla + DRB1*0414.hla = 0
DRB1*0412.hla + DRB1*0415.hla = 0
DRB1*0412.hla + DRB1*0416.hla = 0
DRB1*0412.hla + DRB1*0417.hla = 0
DRB1*0412.hla + DRB1*0418.hla = 0
DRB1*0412.hla + DRB1*0419.hla = 0
DRB1*0412.hla + DRB1*0420.hla = 1
DRB1*0412.hla + DRB1*0421.hla = 1
DRB1*0412.hla + DRB1*0422.hla = 0
DRB1*0413.hla + DRB1*0414.hla = 0
DRB1*0413.hla + DRB1*0415.hla = 0
DRB1*0413.hla + DRB1*0416.hla = 0
DRB1*0413.hla + DRB1*0417.hla = 0
DRB1*0413.hla + DRB1*0418.hla = 0
DRB1*0413.hla + DRB1*0419.hla = 0
DRB1*0413.hla + DRB1*0420.hla = 0
DRB1*0413.hla + DRB1*0421.hla = 1
DRB1*0413.hla + DRB1*0422.hla = 0
DRB1*0414.hla + DRB1*0415.hla = 0
DRB1*0414.hla + DRB1*0416.hla = 0
DRB1*0414.hla + DRB1*0417.hla = 0
DRB1*0414.hla + DRB1*0418.hla = 0
DRB1*0414.hla + DRB1*0419.hla = 1
DRB1*0414.hla + DRB1*0420.hla = 0
DRB1*0414.hla + DRB1*0421.hla = 1
DRB1*0414.hla + DRB1*0422.hla = 0
DRB1*0415.hla + DRB1*0416.hla = 0
DRB1*0415.hla + DRB1*0417.hla = 0
```

Appendix 1 (cont'd)

DRB1*0415.hla + DRB1*0418.hla = 0
DRB1*0415.hla + DRB1*0419.hla = 0
DRB1*0415.hla + DRB1*0420.hla = 0
DRB1*0415.hla + DRB1*0421.hla = 1
DRB1*0415.hla + DRB1*0422.hla = 0
DRB1*0416.hla + DRB1*0417.hla = 0
DRB1*0416.hla + DRB1*0418.hla = 0
DRB1*0416.hla + DRB1*0419.hla = 1
DRB1*0416.hla + DRB1*0420.hla = 0
DRB1*0416.hla + DRB1*0421.hla = 1
DRB1*0416.hla + DRB1*0422.hla = 0
DRB1*0417.hla + DRB1*0418.hla = 0
DRB1*0417.hla + DRB1*0419.hla = 2
DRB1*0417.hla + DRB1*0420.hla = 2
DRB1*0417.hla + DRB1*0421.hla = 2
DRB1*0417.hla + DRB1*0422.hla = 0
DRB1*0418.hla + DRB1*0419.hla = 2
DRB1*0418.hla + DRB1*0420.hla = 2
DRB1*0418.hla + DRB1*0421.hla = 1
DRB1*0418.hla + DRB1*0422.hla = 0
DRB1*0419.hla + DRB1*0420.hla = 0
DRB1*0419.hla + DRB1*0421.hla = 0
DRB1*0419.hla + DRB1*0422.hla = 0
DRB1*0420.hla + DRB1*0421.hla = 0
DRB1*0420.hla + DRB1*0422.hla = 0
DRB1*0421.hla + DRB1*0422.hla = 1

Unique Sequences using CT:

DRB1*0401.hla + DRB1*0402.hla = 2
DRB1*0401.hla + DRB1*0403.hla = 7
DRB1*0401.hla + DRB1*0404.hla = 4
DRB1*0401.hla + DRB1*0405.hla = 2
DRB1*0401.hla + DRB1*0406.hla = 7
DRB1*0401.hla + DRB1*0407.hla = 2
DRB1*0401.hla + DRB1*0408.hla = 3
DRB1*0401.hla + DRB1*0409.hla = 3
DRB1*0401.hla + DRB1*0410.hla = 4
DRB1*0401.hla + DRB1*0411.hla = 6
DRB1*0401.hla + DRB1*0412.hla = 2
DRB1*0401.hla + DRB1*0413.hla = 4
DRB1*0401.hla + DRB1*0414.hla = 1
DRB1*0401.hla + DRB1*0415.hla = 2
DRB1*0401.hla + DRB1*0416.hla = 3
DRB1*0401.hla + DRB1*0417.hla = 4
DRB1*0401.hla + DRB1*0418.hla = 1
DRB1*0401.hla + DRB1*0419.hla = 1
DRB1*0401.hla + DRB1*0420.hla = 3
DRB1*0401.hla + DRB1*0421.hla = 1
DRB1*0401.hla + DRB1*0422.hla = 3
DRB1*0402.hla + DRB1*0403.hla = 1
DRB1*0402.hla + DRB1*0404.hla = 1
DRB1*0402.hla + DRB1*0405.hla = 0
DRB1*0402.hla + DRB1*0406.hla = 1
DRB1*0402.hla + DRB1*0407.hla = 0
DRB1*0402.hla + DRB1*0408.hla = 2
DRB1*0402.hla + DRB1*0409.hla = 1
DRB1*0402.hla + DRB1*0410.hla = 0
DRB1*0402.hla + DRB1*0411.hla = 2
DRB1*0402.hla + DRB1*0412.hla = 0
DRB1*0402.hla + DRB1*0413.hla = 1

Appendix 1 (cont'd)

DRB1*0402.hla + DRB1*0414.hla = 0
DRB1*0402.hla + DRB1*0415.hla = 0
DRB1*0402.hla + DRB1*0416.hla = 2
DRB1*0402.hla + DRB1*0417.hla = 2
DRB1*0402.hla + DRB1*0418.hla = 0
DRB1*0402.hla + DRB1*0419.hla = 2
DRB1*0402.hla + DRB1*0420.hla = 3
DRB1*0402.hla + DRB1*0421.hla = 2
DRB1*0402.hla + DRB1*0422.hla = 0
DRB1*0403.hla + DRB1*0404.hla = 4
DRB1*0403.hla + DRB1*0405.hla = 6
DRB1*0403.hla + DRB1*0406.hla = 4
DRB1*0403.hla + DRB1*0407.hla = 7
DRB1*0403.hla + DRB1*0408.hla = 5
DRB1*0403.hla + DRB1*0409.hla = 8
DRB1*0403.hla + DRB1*0410.hla = 5
DRB1*0403.hla + DRB1*0411.hla = 5
DRB1*0403.hla + DRB1*0412.hla = 2
DRB1*0403.hla + DRB1*0413.hla = 4
DRB1*0403.hla + DRB1*0414.hla = 3
DRB1*0403.hla + DRB1*0415.hla = 1
DRB1*0403.hla + DRB1*0416.hla = 5
DRB1*0403.hla + DRB1*0417.hla = 8
DRB1*0403.hla + DRB1*0418.hla = 1
DRB1*0403.hla + DRB1*0419.hla = 7
DRB1*0403.hla + DRB1*0420.hla = 5
DRB1*0403.hla + DRB1*0421.hla = 7
DRB1*0403.hla + DRB1*0422.hla = 3
DRB1*0404.hla + DRB1*0405.hla = 4
DRB1*0404.hla + DRB1*0406.hla = 4
DRB1*0404.hla + DRB1*0407.hla = 7
DRB1*0404.hla + DRB1*0408.hla = 1
DRB1*0404.hla + DRB1*0409.hla = 2
DRB1*0404.hla + DRB1*0410.hla = 1
DRB1*0404.hla + DRB1*0411.hla = 5
DRB1*0404.hla + DRB1*0412.hla = 1
DRB1*0404.hla + DRB1*0413.hla = 0
DRB1*0404.hla + DRB1*0414.hla = 2
DRB1*0404.hla + DRB1*0415.hla = 1
DRB1*0404.hla + DRB1*0416.hla = 1
DRB1*0404.hla + DRB1*0417.hla = 8
DRB1*0404.hla + DRB1*0418.hla = 0
DRB1*0404.hla + DRB1*0419.hla = 4
DRB1*0404.hla + DRB1*0420.hla = 5
DRB1*0404.hla + DRB1*0421.hla = 4
DRB1*0404.hla + DRB1*0422.hla = 3
DRB1*0405.hla + DRB1*0406.hla = 6
DRB1*0405.hla + DRB1*0407.hla = 0
DRB1*0405.hla + DRB1*0408.hla = 3
DRB1*0405.hla + DRB1*0409.hla = 0
DRB1*0405.hla + DRB1*0410.hla = 0
DRB1*0405.hla + DRB1*0411.hla = 0
DRB1*0405.hla + DRB1*0412.hla = 0
DRB1*0405.hla + DRB1*0413.hla = 4
DRB1*0405.hla + DRB1*0414.hla = 0
DRB1*0405.hla + DRB1*0415.hla = 0
DRB1*0405.hla + DRB1*0416.hla = 3
DRB1*0405.hla + DRB1*0417.hla = 0
DRB1*0405.hla + DRB1*0418.hla = 2
DRB1*0405.hla + DRB1*0419.hla = 2
DRB1*0405.hla + DRB1*0420.hla = 4

- 117 -

Appendix 1 (cont'd)

DRB1*0405.hla + DRB1*0421.hla = 2
DRB1*0405.hla + DRB1*0422.hla = 0
DRB1*0406.hla + DRB1*0407.hla = 7
DRB1*0406.hla + DRB1*0408.hla = 5
DRB1*0406.hla + DRB1*0409.hla = 8
DRB1*0406.hla + DRB1*0410.hla = 5
DRB1*0406.hla + DRB1*0411.hla = 5
DRB1*0406.hla + DRB1*0412.hla = 2
DRB1*0406.hla + DRB1*0413.hla = 4
DRB1*0406.hla + DRB1*0414.hla = 3
DRB1*0406.hla + DRB1*0415.hla = 1
DRB1*0406.hla + DRB1*0416.hla = 5
DRB1*0406.hla + DRB1*0417.hla = 8
DRB1*0406.hla + DRB1*0418.hla = 1
DRB1*0406.hla + DRB1*0419.hla = 1
DRB1*0406.hla + DRB1*0420.hla = 0
DRB1*0406.hla + DRB1*0421.hla = 1
DRB1*0406.hla + DRB1*0422.hla = 3
DRB1*0407.hla + DRB1*0408.hla = 3
DRB1*0407.hla + DRB1*0409.hla = 4
DRB1*0407.hla + DRB1*0410.hla = 6
DRB1*0407.hla + DRB1*0411.hla = 6
DRB1*0407.hla + DRB1*0412.hla = 0
DRB1*0407.hla + DRB1*0413.hla = 7
DRB1*0407.hla + DRB1*0414.hla = 0
DRB1*0407.hla + DRB1*0415.hla = 0
DRB1*0407.hla + DRB1*0416.hla = 3
DRB1*0407.hla + DRB1*0417.hla = 4
DRB1*0407.hla + DRB1*0418.hla = 3
DRB1*0407.hla + DRB1*0419.hla = 2
DRB1*0407.hla + DRB1*0420.hla = 3
DRB1*0407.hla + DRB1*0421.hla = 2
DRB1*0407.hla + DRB1*0422.hla = 3
DRB1*0408.hla + DRB1*0409.hla = 0
DRB1*0408.hla + DRB1*0410.hla = 2
DRB1*0408.hla + DRB1*0411.hla = 8
DRB1*0408.hla + DRB1*0412.hla = 2
DRB1*0408.hla + DRB1*0413.hla = 1
DRB1*0408.hla + DRB1*0414.hla = 0
DRB1*0408.hla + DRB1*0415.hla = 1
DRB1*0408.hla + DRB1*0416.hla = 0
DRB1*0408.hla + DRB1*0417.hla = 3
DRB1*0408.hla + DRB1*0418.hla = 0
DRB1*0408.hla + DRB1*0419.hla = 1
DRB1*0408.hla + DRB1*0420.hla = 1
DRB1*0408.hla + DRB1*0421.hla = 3
DRB1*0408.hla + DRB1*0422.hla = 2
DRB1*0409.hla + DRB1*0410.hla = 0
DRB1*0409.hla + DRB1*0411.hla = 2
DRB1*0409.hla + DRB1*0412.hla = 0
DRB1*0409.hla + DRB1*0413.hla = 0
DRB1*0409.hla + DRB1*0414.hla = 0
DRB1*0409.hla + DRB1*0415.hla = 0
DRB1*0409.hla + DRB1*0416.hla = 0
DRB1*0409.hla + DRB1*0417.hla = 0
DRB1*0409.hla + DRB1*0418.hla = 0
DRB1*0409.hla + DRB1*0419.hla = 0
DRB1*0409.hla + DRB1*0420.hla = 3
DRB1*0409.hla + DRB1*0421.hla = 3
DRB1*0409.hla + DRB1*0422.hla = 1
DRB1*0410.hla + DRB1*0411.hla = 0

- 118 -

Appendix 1 (cont'd)

```
DRB1*0410.hla + DRB1*0412.hla = 0
DRB1*0410.hla + DRB1*0413.hla = 1
DRB1*0410.hla + DRB1*0414.hla = 1
DRB1*0410.hla + DRB1*0415.hla = 0
DRB1*0410.hla + DRB1*0416.hla = 2
DRB1*0410.hla + DRB1*0417.hla = 2
DRB1*0410.hla + DRB1*0418.hla = 0
DRB1*0410.hla + DRB1*0419.hla = 4
DRB1*0410.hla + DRB1*0420.hla = 8
DRB1*0410.hla + DRB1*0421.hla = 4
DRB1*0410.hla + DRB1*0422.hla = 1
DRB1*0411.hla + DRB1*0412.hla = 0
DRB1*0411.hla + DRB1*0413.hla = 5
DRB1*0411.hla + DRB1*0414.hla = 2
DRB1*0411.hla + DRB1*0415.hla = 0
DRB1*0411.hla + DRB1*0416.hla = 8
DRB1*0411.hla + DRB1*0417.hla = 2
DRB1*0411.hla + DRB1*0418.hla = 0
DRB1*0411.hla + DRB1*0419.hla = 6
DRB1*0411.hla + DRB1*0420.hla = 8
DRB1*0411.hla + DRB1*0421.hla = 6
DRB1*0411.hla + DRB1*0422.hla = 1
DRB1*0412.hla + DRB1*0413.hla = 1
DRB1*0412.hla + DRB1*0414.hla = 0
DRB1*0412.hla + DRB1*0415.hla = 0
DRB1*0412.hla + DRB1*0416.hla = 2
DRB1*0412.hla + DRB1*0417.hla = 0
DRB1*0412.hla + DRB1*0418.hla = 0
DRB1*0412.hla + DRB1*0419.hla = 2
DRB1*0412.hla + DRB1*0420.hla = 2
DRB1*0412.hla + DRB1*0421.hla = 2
DRB1*0412.hla + DRB1*0422.hla = 0
DRB1*0413.hla + DRB1*0414.hla = 0
DRB1*0413.hla + DRB1*0415.hla = 1
DRB1*0413.hla + DRB1*0416.hla = 1
DRB1*0413.hla + DRB1*0417.hla = 0
DRB1*0413.hla + DRB1*0418.hla = 0
DRB1*0413.hla + DRB1*0419.hla = 0
DRB1*0413.hla + DRB1*0420.hla = 0
DRB1*0413.hla + DRB1*0421.hla = 4
DRB1*0413.hla + DRB1*0422.hla = 3
DRB1*0414.hla + DRB1*0415.hla = 0
DRB1*0414.hla + DRB1*0416.hla = 0
DRB1*0414.hla + DRB1*0417.hla = 0
DRB1*0414.hla + DRB1*0418.hla = 0
DRB1*0414.hla + DRB1*0419.hla = 0
DRB1*0414.hla + DRB1*0420.hla = 0
DRB1*0414.hla + DRB1*0421.hla = 1
DRB1*0414.hla + DRB1*0422.hla = 0
DRB1*0415.hla + DRB1*0416.hla = 1
DRB1*0415.hla + DRB1*0417.hla = 0
DRB1*0415.hla + DRB1*0418.hla = 0
DRB1*0415.hla + DRB1*0419.hla = 2
DRB1*0415.hla + DRB1*0420.hla = 0
DRB1*0415.hla + DRB1*0421.hla = 2
DRB1*0415.hla + DRB1*0422.hla = 0
DRB1*0416.hla + DRB1*0417.hla = 3
DRB1*0416.hla + DRB1*0418.hla = 0
DRB1*0416.hla + DRB1*0419.hla = 1
DRB1*0416.hla + DRB1*0420.hla = 1
DRB1*0416.hla + DRB1*0421.hla = 3
```

- 119 -

Appendix 1 (cont'd)

DRB1*0416.hla + DRB1*0422.hla = 2
DRB1*0417.hla + DRB1*0418.hla = 0
DRB1*0417.hla + DRB1*0419.hla = 0
DRB1*0417.hla + DRB1*0420.hla = 3
DRB1*0417.hla + DRB1*0421.hla = 4
DRB1*0417.hla + DRB1*0422.hla = 1
DRB1*0418.hla + DRB1*0419.hla = 0
DRB1*0418.hla + DRB1*0420.hla = 0
DRB1*0418.hla + DRB1*0421.hla = 1
DRB1*0418.hla + DRB1*0422.hla = 0
DRB1*0419.hla + DRB1*0420.hla = 0
DRB1*0419.hla + DRB1*0421.hla = 0
DRB1*0419.hla + DRB1*0422.hla = 3
DRB1*0420.hla + DRB1*0421.hla = 0
DRB1*0420.hla + DRB1*0422.hla = 2
DRB1*0421.hla + DRB1*0422.hla = 3

Unique Sequences using GT:

DRB1*0401.hla + DRB1*0402.hla = 4
DRB1*0401.hla + DRB1*0403.hla = 5
DRB1*0401.hla + DRB1*0404.hla = 5
DRB1*0401.hla + DRB1*0405.hla = 1
DRB1*0401.hla + DRB1*0406.hla = 5
DRB1*0401.hla + DRB1*0407.hla = 2
DRB1*0401.hla + DRB1*0408.hla = 5
DRB1*0401.hla + DRB1*0409.hla = 4
DRB1*0401.hla + DRB1*0410.hla = 1
DRB1*0401.hla + DRB1*0411.hla = 1
DRB1*0401.hla + DRB1*0412.hla = 1
DRB1*0401.hla + DRB1*0413.hla = 2
DRB1*0401.hla + DRB1*0414.hla = 2
DRB1*0401.hla + DRB1*0415.hla = 4
DRB1*0401.hla + DRB1*0416.hla = 2
DRB1*0401.hla + DRB1*0417.hla = 4
DRB1*0401.hla + DRB1*0418.hla = 1
DRB1*0401.hla + DRB1*0419.hla = 5
DRB1*0401.hla + DRB1*0420.hla = 5
DRB1*0401.hla + DRB1*0421.hla = 2
DRB1*0401.hla + DRB1*0422.hla = 2
DRB1*0402.hla + DRB1*0403.hla = 2
DRB1*0402.hla + DRB1*0404.hla = 2
DRB1*0402.hla + DRB1*0405.hla = 0
DRB1*0402.hla + DRB1*0406.hla = 2
DRB1*0402.hla + DRB1*0407.hla = 4
DRB1*0402.hla + DRB1*0408.hla = 5
DRB1*0402.hla + DRB1*0409.hla = 3
DRB1*0402.hla + DRB1*0410.hla = 0
DRB1*0402.hla + DRB1*0411.hla = 0
DRB1*0402.hla + DRB1*0412.hla = 0
DRB1*0402.hla + DRB1*0413.hla = 1
DRB1*0402.hla + DRB1*0414.hla = 0
DRB1*0402.hla + DRB1*0415.hla = 0
DRB1*0402.hla + DRB1*0416.hla = 1
DRB1*0402.hla + DRB1*0417.hla = 3
DRB1*0402.hla + DRB1*0418.hla = 0
DRB1*0402.hla + DRB1*0419.hla = 5
DRB1*0402.hla + DRB1*0420.hla = 5
DRB1*0402.hla + DRB1*0421.hla = 4
DRB1*0402.hla + DRB1*0422.hla = 1
DRB1*0403.hla + DRB1*0404.hla = 2

- 120 -

Appendix 1 (cont'd)

DRB1*0403.hla + DRB1*0405.hla = 3
DRB1*0403.hla + DRB1*0406.hla = 2
DRB1*0403.hla + DRB1*0407.hla = 2
DRB1*0403.hla + DRB1*0408.hla = 8
DRB1*0403.hla + DRB1*0409.hla = 3
DRB1*0403.hla + DRB1*0410.hla = 2
DRB1*0403.hla + DRB1*0411.hla = 2
DRB1*0403.hla + DRB1*0412.hla = 2
DRB1*0403.hla + DRB1*0413.hla = 2
DRB1*0403.hla + DRB1*0414.hla = 5
DRB1*0403.hla + DRB1*0415.hla = 2
DRB1*0403.hla + DRB1*0416.hla = 2
DRB1*0403.hla + DRB1*0417.hla = 5
DRB1*0403.hla + DRB1*0418.hla = 2
DRB1*0403.hla + DRB1*0419.hla = 8
DRB1*0403.hla + DRB1*0420.hla = 8
DRB1*0403.hla + DRB1*0421.hla = 5
DRB1*0403.hla + DRB1*0422.hla = 2
DRB1*0404.hla + DRB1*0405.hla = 3
DRB1*0404.hla + DRB1*0406.hla = 2
DRB1*0404.hla + DRB1*0407.hla = 2
DRB1*0404.hla + DRB1*0408.hla = 8
DRB1*0404.hla + DRB1*0409.hla = 3
DRB1*0404.hla + DRB1*0410.hla = 2
DRB1*0404.hla + DRB1*0411.hla = 2
DRB1*0404.hla + DRB1*0412.hla = 2
DRB1*0404.hla + DRB1*0413.hla = 2
DRB1*0404.hla + DRB1*0414.hla = 5
DRB1*0404.hla + DRB1*0415.hla = 2
DRB1*0404.hla + DRB1*0416.hla = 2
DRB1*0404.hla + DRB1*0417.hla = 5
DRB1*0404.hla + DRB1*0418.hla = 2
DRB1*0404.hla + DRB1*0419.hla = 8
DRB1*0404.hla + DRB1*0420.hla = 8
DRB1*0404.hla + DRB1*0421.hla = 5
DRB1*0404.hla + DRB1*0422.hla = 2
DRB1*0405.hla + DRB1*0406.hla = 3
DRB1*0405.hla + DRB1*0407.hla = 0
DRB1*0405.hla + DRB1*0408.hla = 3
DRB1*0405.hla + DRB1*0409.hla = 0
DRB1*0405.hla + DRB1*0410.hla = 0
DRB1*0405.hla + DRB1*0411.hla = 0
DRB1*0405.hla + DRB1*0412.hla = 0
DRB1*0405.hla + DRB1*0413.hla = 3
DRB1*0405.hla + DRB1*0414.hla = 0
DRB1*0405.hla + DRB1*0415.hla = 0
DRB1*0405.hla + DRB1*0416.hla = 0
DRB1*0405.hla + DRB1*0417.hla = 0
DRB1*0405.hla + DRB1*0418.hla = 0
DRB1*0405.hla + DRB1*0419.hla = 3
DRB1*0405.hla + DRB1*0420.hla = 3
DRB1*0405.hla + DRB1*0421.hla = 1
DRB1*0405.hla + DRB1*0422.hla = 0
DRB1*0406.hla + DRB1*0407.hla = 2
DRB1*0406.hla + DRB1*0408.hla = 8
DRB1*0406.hla + DRB1*0409.hla = 3
DRB1*0406.hla + DRB1*0410.hla = 2
DRB1*0406.hla + DRB1*0411.hla = 2
DRB1*0406.hla + DRB1*0412.hla = 2
DRB1*0406.hla + DRB1*0413.hla = 2
DRB1*0406.hla + DRB1*0414.hla = 5

- 121 -

Appendix 1 (cont'd)

DRB1*0406.hla + DRB1*0415.hla = 2
DRB1*0406.hla + DRB1*0416.hla = 2
DRB1*0406.hla + DRB1*0417.hla = 5
DRB1*0406.hla + DRB1*0418.hla = 2
DRB1*0406.hla + DRB1*0419.hla = 8
DRB1*0406.hla + DRB1*0420.hla = 8
DRB1*0406.hla + DRB1*0421.hla = 5
DRB1*0406.hla + DRB1*0422.hla = 2
DRB1*0407.hla + DRB1*0408.hla = 2
DRB1*0407.hla + DRB1*0409.hla = 4
DRB1*0407.hla + DRB1*0410.hla = 3
DRB1*0407.hla + DRB1*0411.hla = 0
DRB1*0407.hla + DRB1*0412.hla = 0
DRB1*0407.hla + DRB1*0413.hla = 2
DRB1*0407.hla + DRB1*0414.hla = 2
DRB1*0407.hla + DRB1*0415.hla = 0
DRB1*0407.hla + DRB1*0416.hla = 2
DRB1*0407.hla + DRB1*0417.hla = 3
DRB1*0407.hla + DRB1*0418.hla = 0
DRB1*0407.hla + DRB1*0419.hla = 2
DRB1*0407.hla + DRB1*0420.hla = 2
DRB1*0407.hla + DRB1*0421.hla = 2
DRB1*0407.hla + DRB1*0422.hla = 2
DRB1*0408.hla + DRB1*0409.hla = 0
DRB1*0408.hla + DRB1*0410.hla = 5
DRB1*0408.hla + DRB1*0411.hla = 2
DRB1*0408.hla + DRB1*0412.hla = 2
DRB1*0408.hla + DRB1*0413.hla = 2
DRB1*0408.hla + DRB1*0414.hla = 0
DRB1*0408.hla + DRB1*0415.hla = 2
DRB1*0408.hla + DRB1*0416.hla = 1
DRB1*0408.hla + DRB1*0417.hla = 1
DRB1*0408.hla + DRB1*0418.hla = 0
DRB1*0408.hla + DRB1*0419.hla = 1
DRB1*0408.hla + DRB1*0420.hla = 0
DRB1*0408.hla + DRB1*0421.hla = 5
DRB1*0408.hla + DRB1*0422.hla = 2
DRB1*0409.hla + DRB1*0410.hla = 0
DRB1*0409.hla + DRB1*0411.hla = 0
DRB1*0409.hla + DRB1*0412.hla = 0
DRB1*0409.hla + DRB1*0413.hla = 1
DRB1*0409.hla + DRB1*0414.hla = 0
DRB1*0409.hla + DRB1*0415.hla = 3
DRB1*0409.hla + DRB1*0416.hla = 1
DRB1*0409.hla + DRB1*0417.hla = 0
DRB1*0409.hla + DRB1*0418.hla = 0
DRB1*0409.hla + DRB1*0419.hla = 0
DRB1*0409.hla + DRB1*0420.hla = 0
DRB1*0409.hla + DRB1*0421.hla = 4
DRB1*0409.hla + DRB1*0422.hla = 1
DRB1*0410.hla + DRB1*0411.hla = 0
DRB1*0410.hla + DRB1*0412.hla = 0
DRB1*0410.hla + DRB1*0413.hla = 0
DRB1*0410.hla + DRB1*0414.hla = 3
DRB1*0410.hla + DRB1*0415.hla = 0
DRB1*0410.hla + DRB1*0416.hla = 0
DRB1*0410.hla + DRB1*0417.hla = 0
DRB1*0410.hla + DRB1*0418.hla = 0
DRB1*0410.hla + DRB1*0419.hla = 5
DRB1*0410.hla + DRB1*0420.hla = 5
DRB1*0410.hla + DRB1*0421.hla = 1

Appendix 1 (cont'd)

DRB1*0410.hla + DRB1*0422.hla = 0
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 0
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 2
DRB1*0411.hla + DRB1*0420.hla = 2
DRB1*0411.hla + DRB1*0421.hla = 1
DRB1*0411.hla + DRB1*0422.hla = 0
DRB1*0412.hla + DRB1*0413.hla = 0
DRB1*0412.hla + DRB1*0414.hla = 0
DRB1*0412.hla + DRB1*0415.hla = 0
DRB1*0412.hla + DRB1*0416.hla = 0
DRB1*0412.hla + DRB1*0417.hla = 0
DRB1*0412.hla + DRB1*0418.hla = 0
DRB1*0412.hla + DRB1*0419.hla = 2
DRB1*0412.hla + DRB1*0420.hla = 2
DRB1*0412.hla + DRB1*0421.hla = 1
DRB1*0412.hla + DRB1*0422.hla = 0
DRB1*0413.hla + DRB1*0414.hla = 0
DRB1*0413.hla + DRB1*0415.hla = 1
DRB1*0413.hla + DRB1*0416.hla = 0
DRB1*0413.hla + DRB1*0417.hla = 1
DRB1*0413.hla + DRB1*0418.hla = 0
DRB1*0413.hla + DRB1*0419.hla = 2
DRB1*0413.hla + DRB1*0420.hla = 2
DRB1*0413.hla + DRB1*0421.hla = 2
DRB1*0413.hla + DRB1*0422.hla = 0
DRB1*0414.hla + DRB1*0415.hla = 0
DRB1*0414.hla + DRB1*0416.hla = 0
DRB1*0414.hla + DRB1*0417.hla = 0
DRB1*0414.hla + DRB1*0418.hla = 0
DRB1*0414.hla + DRB1*0419.hla = 0
DRB1*0414.hla + DRB1*0420.hla = 0
DRB1*0414.hla + DRB1*0421.hla = 2
DRB1*0414.hla + DRB1*0422.hla = 0
DRB1*0415.hla + DRB1*0416.hla = 1
DRB1*0415.hla + DRB1*0417.hla = 0
DRB1*0415.hla + DRB1*0418.hla = 0
DRB1*0415.hla + DRB1*0419.hla = 2
DRB1*0415.hla + DRB1*0420.hla = 2
DRB1*0415.hla + DRB1*0421.hla = 4
DRB1*0415.hla + DRB1*0422.hla = 1
DRB1*0416.hla + DRB1*0417.hla = 1
DRB1*0416.hla + DRB1*0418.hla = 0
DRB1*0416.hla + DRB1*0419.hla = 0
DRB1*0416.hla + DRB1*0420.hla = 1
DRB1*0416.hla + DRB1*0421.hla = 2
DRB1*0416.hla + DRB1*0422.hla = 0
DRB1*0417.hla + DRB1*0418.hla = 0
DRB1*0417.hla + DRB1*0419.hla = 0
DRB1*0417.hla + DRB1*0420.hla = 1
DRB1*0417.hla + DRB1*0421.hla = 4
DRB1*0417.hla + DRB1*0422.hla = 1
DRB1*0418.hla + DRB1*0419.hla = 0
DRB1*0418.hla + DRB1*0420.hla = 0
DRB1*0418.hla + DRB1*0421.hla = 1
DRB1*0418.hla + DRB1*0422.hla = 0

Appendix 1 (cont'd)

DRB1*0419.hla + DRB1*0420.hla = 1
DRB1*0419.hla + DRB1*0421.hla = 5
DRB1*0419.hla + DRB1*0422.hla = 2
DRB1*0420.hla + DRB1*0421.hla = 5
DRB1*0420.hla + DRB1*0422.hla = 2
DRB1*0421.hla + DRB1*0422.hla = 2

Unique Sequences using ACG:

DRB1*0401.hla + DRB1*0402.hla = 0
DRB1*0401.hla + DRB1*0403.hla = 0
DRB1*0401.hla + DRB1*0404.hla = 0
DRB1*0401.hla + DRB1*0405.hla = 0
DRB1*0401.hla + DRB1*0406.hla = 1
DRB1*0401.hla + DRB1*0407.hla = 0
DRB1*0401.hla + DRB1*0408.hla = 0
DRB1*0401.hla + DRB1*0409.hla = 0
DRB1*0401.hla + DRB1*0410.hla = 0
DRB1*0401.hla + DRB1*0411.hla = 0
DRB1*0401.hla + DRB1*0412.hla = 0
DRB1*0401.hla + DRB1*0413.hla = 0
DRB1*0401.hla + DRB1*0414.hla = 0
DRB1*0401.hla + DRB1*0415.hla = 0
DRB1*0401.hla + DRB1*0416.hla = 0
DRB1*0401.hla + DRB1*0417.hla = 0
DRB1*0401.hla + DRB1*0418.hla = 0
DRB1*0401.hla + DRB1*0419.hla = 0
DRB1*0401.hla + DRB1*0420.hla = 0
DRB1*0401.hla + DRB1*0421.hla = 0
DRB1*0401.hla + DRB1*0422.hla = 0
DRB1*0402.hla + DRB1*0403.hla = 0
DRB1*0402.hla + DRB1*0404.hla = 0
DRB1*0402.hla + DRB1*0405.hla = 0
DRB1*0402.hla + DRB1*0406.hla = 0
DRB1*0402.hla + DRB1*0407.hla = 0
DRB1*0402.hla + DRB1*0408.hla = 1
DRB1*0402.hla + DRB1*0409.hla = 0
DRB1*0402.hla + DRB1*0410.hla = 0
DRB1*0402.hla + DRB1*0411.hla = 0
DRB1*0402.hla + DRB1*0412.hla = 0
DRB1*0402.hla + DRB1*0413.hla = 0
DRB1*0402.hla + DRB1*0414.hla = 0
DRB1*0402.hla + DRB1*0415.hla = 0
DRB1*0402.hla + DRB1*0416.hla = 0
DRB1*0402.hla + DRB1*0417.hla = 0
DRB1*0402.hla + DRB1*0418.hla = 0
DRB1*0402.hla + DRB1*0419.hla = 0
DRB1*0402.hla + DRB1*0420.hla = 0
DRB1*0402.hla + DRB1*0421.hla = 0
DRB1*0402.hla + DRB1*0422.hla = 0
DRB1*0403.hla + DRB1*0404.hla = 0
DRB1*0403.hla + DRB1*0405.hla = 1
DRB1*0403.hla + DRB1*0406.hla = 0
DRB1*0403.hla + DRB1*0407.hla = 0
DRB1*0403.hla + DRB1*0408.hla = 0
DRB1*0403.hla + DRB1*0409.hla = 0
DRB1*0403.hla + DRB1*0410.hla = 0
DRB1*0403.hla + DRB1*0411.hla = 0
DRB1*0403.hla + DRB1*0412.hla = 1
DRB1*0403.hla + DRB1*0413.hla = 0
DRB1*0403.hla + DRB1*0414.hla = 0

Appendix 1 (cont'd)

DRB1*0403.hla + DRB1*0415.hla = 0
DRB1*0403.hla + DRB1*0416.hla = 0
DRB1*0403.hla + DRB1*0417.hla = 0
DRB1*0403.hla + DRB1*0418.hla = 1
DRB1*0403.hla + DRB1*0419.hla = 0
DRB1*0403.hla + DRB1*0420.hla = 0
DRB1*0403.hla + DRB1*0421.hla = 1
DRB1*0403.hla + DRB1*0422.hla = 0
DRB1*0404.hla + DRB1*0405.hla = 0
DRB1*0404.hla + DRB1*0406.hla = 0
DRB1*0404.hla + DRB1*0407.hla = 0
DRB1*0404.hla + DRB1*0408.hla = 0
DRB1*0404.hla + DRB1*0409.hla = 0
DRB1*0404.hla + DRB1*0410.hla = 0
DRB1*0404.hla + DRB1*0411.hla = 0
DRB1*0404.hla + DRB1*0412.hla = 1
DRB1*0404.hla + DRB1*0413.hla = 0
DRB1*0404.hla + DRB1*0414.hla = 1
DRB1*0404.hla + DRB1*0415.hla = 0
DRB1*0404.hla + DRB1*0416.hla = 0
DRB1*0404.hla + DRB1*0417.hla = 0
DRB1*0404.hla + DRB1*0418.hla = 1
DRB1*0404.hla + DRB1*0419.hla = 0
DRB1*0404.hla + DRB1*0420.hla = 0
DRB1*0404.hla + DRB1*0421.hla = 0
DRB1*0404.hla + DRB1*0422.hla = 0
DRB1*0405.hla + DRB1*0406.hla = 0
DRB1*0405.hla + DRB1*0407.hla = 0
DRB1*0405.hla + DRB1*0408.hla = 0
DRB1*0405.hla + DRB1*0409.hla = 0
DRB1*0405.hla + DRB1*0410.hla = 0
DRB1*0405.hla + DRB1*0411.hla = 0
DRB1*0405.hla + DRB1*0412.hla = 0
DRB1*0405.hla + DRB1*0413.hla = 0
DRB1*0405.hla + DRB1*0414.hla = 0
DRB1*0405.hla + DRB1*0415.hla = 0
DRB1*0405.hla + DRB1*0416.hla = 0
DRB1*0405.hla + DRB1*0417.hla = 0
DRB1*0405.hla + DRB1*0418.hla = 0
DRB1*0405.hla + DRB1*0419.hla = 0
DRB1*0405.hla + DRB1*0420.hla = 0
DRB1*0405.hla + DRB1*0421.hla = 0
DRB1*0405.hla + DRB1*0422.hla = 0
DRB1*0406.hla + DRB1*0407.hla = 0
DRB1*0406.hla + DRB1*0408.hla = 0
DRB1*0406.hla + DRB1*0409.hla = 0
DRB1*0406.hla + DRB1*0410.hla = 0
DRB1*0406.hla + DRB1*0411.hla = 0
DRB1*0406.hla + DRB1*0412.hla = 0
DRB1*0406.hla + DRB1*0413.hla = 0
DRB1*0406.hla + DRB1*0414.hla = 0
DRB1*0406.hla + DRB1*0415.hla = 0
DRB1*0406.hla + DRB1*0416.hla = 0
DRB1*0406.hla + DRB1*0417.hla = 0
DRB1*0406.hla + DRB1*0418.hla = 0
DRB1*0406.hla + DRB1*0419.hla = 0
DRB1*0406.hla + DRB1*0420.hla = 0
DRB1*0406.hla + DRB1*0421.hla = 0
DRB1*0406.hla + DRB1*0422.hla = 0
DRB1*0407.hla + DRB1*0408.hla = 0
DRB1*0407.hla + DRB1*0409.hla = 0

Appendix 1 (cont'd)

```
DRB1*0407.hla + DRB1*0410.hla = 1
DRB1*0407.hla + DRB1*0411.hla = 0
DRB1*0407.hla + DRB1*0412.hla = 0
DRB1*0407.hla + DRB1*0413.hla = 0
DRB1*0407.hla + DRB1*0414.hla = 0
DRB1*0407.hla + DRB1*0415.hla = 0
DRB1*0407.hla + DRB1*0416.hla = 0
DRB1*0407.hla + DRB1*0417.hla = 0
DRB1*0407.hla + DRB1*0418.hla = 0
DRB1*0407.hla + DRB1*0419.hla = 0
DRB1*0407.hla + DRB1*0420.hla = 0
DRB1*0407.hla + DRB1*0421.hla = 0
DRB1*0407.hla + DRB1*0422.hla = 0
DRB1*0408.hla + DRB1*0409.hla = 0
DRB1*0408.hla + DRB1*0410.hla = 0
DRB1*0408.hla + DRB1*0411.hla = 0
DRB1*0408.hla + DRB1*0412.hla = 0
DRB1*0408.hla + DRB1*0413.hla = 0
DRB1*0408.hla + DRB1*0414.hla = 0
DRB1*0408.hla + DRB1*0415.hla = 0
DRB1*0408.hla + DRB1*0416.hla = 0
DRB1*0408.hla + DRB1*0417.hla = 0
DRB1*0408.hla + DRB1*0418.hla = 0
DRB1*0408.hla + DRB1*0419.hla = 0
DRB1*0408.hla + DRB1*0420.hla = 0
DRB1*0408.hla + DRB1*0421.hla = 0
DRB1*0408.hla + DRB1*0422.hla = 0
DRB1*0409.hla + DRB1*0410.hla = 0
DRB1*0409.hla + DRB1*0411.hla = 0
DRB1*0409.hla + DRB1*0412.hla = 0
DRB1*0409.hla + DRB1*0413.hla = 0
DRB1*0409.hla + DRB1*0414.hla = 0
DRB1*0409.hla + DRB1*0415.hla = 0
DRB1*0409.hla + DRB1*0416.hla = 0
DRB1*0409.hla + DRB1*0417.hla = 0
DRB1*0409.hla + DRB1*0418.hla = 0
DRB1*0409.hla + DRB1*0419.hla = 0
DRB1*0409.hla + DRB1*0420.hla = 0
DRB1*0409.hla + DRB1*0421.hla = 0
DRB1*0409.hla + DRB1*0422.hla = 0
DRB1*0410.hla + DRB1*0411.hla = 0
DRB1*0410.hla + DRB1*0412.hla = 0
DRB1*0410.hla + DRB1*0413.hla = 0
DRB1*0410.hla + DRB1*0414.hla = 0
DRB1*0410.hla + DRB1*0415.hla = 0
DRB1*0410.hla + DRB1*0416.hla = 0
DRB1*0410.hla + DRB1*0417.hla = 0
DRB1*0410.hla + DRB1*0418.hla = 0
DRB1*0410.hla + DRB1*0419.hla = 0
DRB1*0410.hla + DRB1*0420.hla = 0
DRB1*0410.hla + DRB1*0421.hla = 0
DRB1*0410.hla + DRB1*0422.hla = 0
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 0
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 0
DRB1*0411.hla + DRB1*0420.hla = 0
```

- 126 -

Appendix 1 (cont'd)

DRB1*0411.hla + DRB1*0421.hla = 0
DRB1*0411.hla + DRB1*0422.hla = 0
DRB1*0412.hla + DRB1*0413.hla = 0
DRB1*0412.hla + DRB1*0414.hla = 0
DRB1*0412.hla + DRB1*0415.hla = 0
DRB1*0412.hla + DRB1*0416.hla = 0
DRB1*0412.hla + DRB1*0417.hla = 0
DRB1*0412.hla + DRB1*0418.hla = 0
DRB1*0412.hla + DRB1*0419.hla = 0
DRB1*0412.hla + DRB1*0420.hla = 0
DRB1*0412.hla + DRB1*0421.hla = 0
DRB1*0412.hla + DRB1*0422.hla = 0
DRB1*0413.hla + DRB1*0414.hla = 0
DRB1*0413.hla + DRB1*0415.hla = 0
DRB1*0413.hla + DRB1*0416.hla = 0
DRB1*0413.hla + DRB1*0417.hla = 0
DRB1*0413.hla + DRB1*0418.hla = 0
DRB1*0413.hla + DRB1*0419.hla = 0
DRB1*0413.hla + DRB1*0420.hla = 0
DRB1*0413.hla + DRB1*0421.hla = 0
DRB1*0413.hla + DRB1*0422.hla = 0
DRB1*0414.hla + DRB1*0415.hla = 0
DRB1*0414.hla + DRB1*0416.hla = 0
DRB1*0414.hla + DRB1*0417.hla = 0
DRB1*0414.hla + DRB1*0418.hla = 0
DRB1*0414.hla + DRB1*0419.hla = 0
DRB1*0414.hla + DRB1*0420.hla = 0
DRB1*0414.hla + DRB1*0421.hla = 0
DRB1*0414.hla + DRB1*0422.hla = 0
DRB1*0415.hla + DRB1*0416.hla = 0
DRB1*0415.hla + DRB1*0417.hla = 0
DRB1*0415.hla + DRB1*0418.hla = 0
DRB1*0415.hla + DRB1*0419.hla = 0
DRB1*0415.hla + DRB1*0420.hla = 0
DRB1*0415.hla + DRB1*0421.hla = 0
DRB1*0415.hla + DRB1*0422.hla = 0
DRB1*0416.hla + DRB1*0417.hla = 0
DRB1*0416.hla + DRB1*0418.hla = 0
DRB1*0416.hla + DRB1*0419.hla = 0
DRB1*0416.hla + DRB1*0420.hla = 0
DRB1*0416.hla + DRB1*0421.hla = 0
DRB1*0416.hla + DRB1*0422.hla = 0
DRB1*0417.hla + DRB1*0418.hla = 0
DRB1*0417.hla + DRB1*0419.hla = 0
DRB1*0417.hla + DRB1*0420.hla = 0
DRB1*0417.hla + DRB1*0421.hla = 0
DRB1*0417.hla + DRB1*0422.hla = 0
DRB1*0418.hla + DRB1*0419.hla = 1
DRB1*0418.hla + DRB1*0420.hla = 1
DRB1*0418.hla + DRB1*0421.hla = 0
DRB1*0418.hla + DRB1*0422.hla = 0
DRB1*0419.hla + DRB1*0420.hla = 0
DRB1*0419.hla + DRB1*0421.hla = 0
DRB1*0419.hla + DRB1*0422.hla = 0
DRB1*0420.hla + DRB1*0421.hla = 0
DRB1*0420.hla + DRB1*0422.hla = 0
DRB1*0421.hla + DRB1*0422.hla = 0

Unique Sequences using ACT:

DRB1*0401.hla + DRB1*0402.hla = 0

Appendix 1 (cont'd)

```
DRB1*0401.hla + DRB1*0403.hla = 1
DRB1*0401.hla + DRB1*0404.hla = 0
DRB1*0401.hla + DRB1*0405.hla = 0
DRB1*0401.hla + DRB1*0406.hla = 1
DRB1*0401.hla + DRB1*0407.hla = 0
DRB1*0401.hla + DRB1*0408.hla = 0
DRB1*0401.hla + DRB1*0409.hla = 0
DRB1*0401.hla + DRB1*0410.hla = 1
DRB1*0401.hla + DRB1*0411.hla = 0
DRB1*0401.hla + DRB1*0412.hla = 0
DRB1*0401.hla + DRB1*0413.hla = 0
DRB1*0401.hla + DRB1*0414.hla = 0
DRB1*0401.hla + DRB1*0415.hla = 0
DRB1*0401.hla + DRB1*0416.hla = 0
DRB1*0401.hla + DRB1*0417.hla = 0
DRB1*0401.hla + DRB1*0418.hla = 0
DRB1*0401.hla + DRB1*0419.hla = 0
DRB1*0401.hla + DRB1*0420.hla = 0
DRB1*0401.hla + DRB1*0421.hla = 0
DRB1*0401.hla + DRB1*0422.hla = 0
DRB1*0402.hla + DRB1*0403.hla = 0
DRB1*0402.hla + DRB1*0404.hla = 0
DRB1*0402.hla + DRB1*0405.hla = 0
DRB1*0402.hla + DRB1*0406.hla = 0
DRB1*0402.hla + DRB1*0407.hla = 0
DRB1*0402.hla + DRB1*0408.hla = 1
DRB1*0402.hla + DRB1*0409.hla = 0
DRB1*0402.hla + DRB1*0410.hla = 0
DRB1*0402.hla + DRB1*0411.hla = 0
DRB1*0402.hla + DRB1*0412.hla = 0
DRB1*0402.hla + DRB1*0413.hla = 0
DRB1*0402.hla + DRB1*0414.hla = 0
DRB1*0402.hla + DRB1*0415.hla = 0
DRB1*0402.hla + DRB1*0416.hla = 0
DRB1*0402.hla + DRB1*0417.hla = 0
DRB1*0402.hla + DRB1*0418.hla = 0
DRB1*0402.hla + DRB1*0419.hla = 0
DRB1*0402.hla + DRB1*0420.hla = 0
DRB1*0402.hla + DRB1*0421.hla = 0
DRB1*0402.hla + DRB1*0422.hla = 0
DRB1*0403.hla + DRB1*0404.hla = 0
DRB1*0403.hla + DRB1*0405.hla = 1
DRB1*0403.hla + DRB1*0406.hla = 0
DRB1*0403.hla + DRB1*0407.hla = 0
DRB1*0403.hla + DRB1*0408.hla = 0
DRB1*0403.hla + DRB1*0409.hla = 0
DRB1*0403.hla + DRB1*0410.hla = 0
DRB1*0403.hla + DRB1*0411.hla = 0
DRB1*0403.hla + DRB1*0412.hla = 0
DRB1*0403.hla + DRB1*0413.hla = 0
DRB1*0403.hla + DRB1*0414.hla = 0
DRB1*0403.hla + DRB1*0415.hla = 0
DRB1*0403.hla + DRB1*0416.hla = 0
DRB1*0403.hla + DRB1*0417.hla = 0
DRB1*0403.hla + DRB1*0418.hla = 0
DRB1*0403.hla + DRB1*0419.hla = 0
DRB1*0403.hla + DRB1*0420.hla = 0
DRB1*0403.hla + DRB1*0421.hla = 1
DRB1*0403.hla + DRB1*0422.hla = 1
DRB1*0404.hla + DRB1*0405.hla = 1
DRB1*0404.hla + DRB1*0406.hla = 0
```

Appendix 1 (cont'd)

DRB1*0404.hla + DRB1*0407.hla = 1
DRB1*0404.hla + DRB1*0408.hla = 0
DRB1*0404.hla + DRB1*0409.hla = 1
DRB1*0404.hla + DRB1*0410.hla = 0
DRB1*0404.hla + DRB1*0411.hla = 0
DRB1*0404.hla + DRB1*0412.hla = 0
DRB1*0404.hla + DRB1*0413.hla = 0
DRB1*0404.hla + DRB1*0414.hla = 1
DRB1*0404.hla + DRB1*0415.hla = 0
DRB1*0404.hla + DRB1*0416.hla = 0
DRB1*0404.hla + DRB1*0417.hla = 0
DRB1*0404.hla + DRB1*0418.hla = 0
DRB1*0404.hla + DRB1*0419.hla = 0
DRB1*0404.hla + DRB1*0420.hla = 1
DRB1*0404.hla + DRB1*0421.hla = 0
DRB1*0404.hla + DRB1*0422.hla = 1
DRB1*0405.hla + DRB1*0406.hla = 0
DRB1*0405.hla + DRB1*0407.hla = 0
DRB1*0405.hla + DRB1*0408.hla = 0
DRB1*0405.hla + DRB1*0409.hla = 0
DRB1*0405.hla + DRB1*0410.hla = 0
DRB1*0405.hla + DRB1*0411.hla = 0
DRB1*0405.hla + DRB1*0412.hla = 0
DRB1*0405.hla + DRB1*0413.hla = 0
DRB1*0405.hla + DRB1*0414.hla = 0
DRB1*0405.hla + DRB1*0415.hla = 0
DRB1*0405.hla + DRB1*0416.hla = 0
DRB1*0405.hla + DRB1*0417.hla = 0
DRB1*0405.hla + DRB1*0418.hla = 1
DRB1*0405.hla + DRB1*0419.hla = 0
DRB1*0405.hla + DRB1*0420.hla = 1
DRB1*0405.hla + DRB1*0421.hla = 0
DRB1*0405.hla + DRB1*0422.hla = 0
DRB1*0406.hla + DRB1*0407.hla = 0
DRB1*0406.hla + DRB1*0408.hla = 0
DRB1*0406.hla + DRB1*0409.hla = 0
DRB1*0406.hla + DRB1*0410.hla = 0
DRB1*0406.hla + DRB1*0411.hla = 0
DRB1*0406.hla + DRB1*0412.hla = 0
DRB1*0406.hla + DRB1*0413.hla = 0
DRB1*0406.hla + DRB1*0414.hla = 0
DRB1*0406.hla + DRB1*0415.hla = 0
DRB1*0406.hla + DRB1*0416.hla = 1
DRB1*0406.hla + DRB1*0417.hla = 0
DRB1*0406.hla + DRB1*0418.hla = 0
DRB1*0406.hla + DRB1*0419.hla = 0
DRB1*0406.hla + DRB1*0420.hla = 0
DRB1*0406.hla + DRB1*0421.hla = 0
DRB1*0406.hla + DRB1*0422.hla = 0
DRB1*0407.hla + DRB1*0408.hla = 0
DRB1*0407.hla + DRB1*0409.hla = 0
DRB1*0407.hla + DRB1*0410.hla = 1
DRB1*0407.hla + DRB1*0411.hla = 0
DRB1*0407.hla + DRB1*0412.hla = 0
DRB1*0407.hla + DRB1*0413.hla = 0
DRB1*0407.hla + DRB1*0414.hla = 0
DRB1*0407.hla + DRB1*0415.hla = 0
DRB1*0407.hla + DRB1*0416.hla = 0
DRB1*0407.hla + DRB1*0417.hla = 0
DRB1*0407.hla + DRB1*0418.hla = 0
DRB1*0407.hla + DRB1*0419.hla = 0

- 129 -

Appendix 1 (cont'd)

DRB1*0407.hla + DRB1*0420.hla = 0
DRB1*0407.hla + DRB1*0421.hla = 0
DRB1*0407.hla + DRB1*0422.hla = 0
DRB1*0408.hla + DRB1*0409.hla = 0
DRB1*0408.hla + DRB1*0410.hla = 1
DRB1*0408.hla + DRB1*0411.hla = 0
DRB1*0408.hla + DRB1*0412.hla = 1
DRB1*0408.hla + DRB1*0413.hla = 0
DRB1*0408.hla + DRB1*0414.hla = 0
DRB1*0408.hla + DRB1*0415.hla = 0
DRB1*0408.hla + DRB1*0416.hla = 0
DRB1*0408.hla + DRB1*0417.hla = 0
DRB1*0408.hla + DRB1*0418.hla = 0
DRB1*0408.hla + DRB1*0419.hla = 0
DRB1*0408.hla + DRB1*0420.hla = 0
DRB1*0408.hla + DRB1*0421.hla = 0
DRB1*0408.hla + DRB1*0422.hla = 0
DRB1*0409.hla + DRB1*0410.hla = 0
DRB1*0409.hla + DRB1*0411.hla = 0
DRB1*0409.hla + DRB1*0412.hla = 0
DRB1*0409.hla + DRB1*0413.hla = 0
DRB1*0409.hla + DRB1*0414.hla = 0
DRB1*0409.hla + DRB1*0415.hla = 0
DRB1*0409.hla + DRB1*0416.hla = 0
DRB1*0409.hla + DRB1*0417.hla = 0
DRB1*0409.hla + DRB1*0418.hla = 0
DRB1*0409.hla + DRB1*0419.hla = 0
DRB1*0409.hla + DRB1*0420.hla = 0
DRB1*0409.hla + DRB1*0421.hla = 0
DRB1*0409.hla + DRB1*0422.hla = 0
DRB1*0410.hla + DRB1*0411.hla = 0
DRB1*0410.hla + DRB1*0412.hla = 0
DRB1*0410.hla + DRB1*0413.hla = 0
DRB1*0410.hla + DRB1*0414.hla = 0
DRB1*0410.hla + DRB1*0415.hla = 0
DRB1*0410.hla + DRB1*0416.hla = 0
DRB1*0410.hla + DRB1*0417.hla = 0
DRB1*0410.hla + DRB1*0418.hla = 0
DRB1*0410.hla + DRB1*0419.hla = 0
DRB1*0410.hla + DRB1*0420.hla = 0
DRB1*0410.hla + DRB1*0421.hla = 0
DRB1*0410.hla + DRB1*0422.hla = 0
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 0
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 0
DRB1*0411.hla + DRB1*0420.hla = 0
DRB1*0411.hla + DRB1*0421.hla = 0
DRB1*0411.hla + DRB1*0422.hla = 0
DRB1*0412.hla + DRB1*0413.hla = 0
DRB1*0412.hla + DRB1*0414.hla = 0
DRB1*0412.hla + DRB1*0415.hla = 0
DRB1*0412.hla + DRB1*0416.hla = 0
DRB1*0412.hla + DRB1*0417.hla = 0
DRB1*0412.hla + DRB1*0418.hla = 0
DRB1*0412.hla + DRB1*0419.hla = 0
DRB1*0412.hla + DRB1*0420.hla = 0

- 130 -

Appendix 1 (cont'd)

DRB1*0412.hla + DRB1*0421.hla = 0
DRB1*0412.hla + DRB1*0422.hla = 0
DRB1*0413.hla + DRB1*0414.hla = 0
DRB1*0413.hla + DRB1*0415.hla = 0
DRB1*0413.hla + DRB1*0416.hla = 0
DRB1*0413.hla + DRB1*0417.hla = 0
DRB1*0413.hla + DRB1*0418.hla = 0
DRB1*0413.hla + DRB1*0419.hla = 0
DRB1*0413.hla + DRB1*0420.hla = 0
DRB1*0413.hla + DRB1*0421.hla = 0
DRB1*0413.hla + DRB1*0422.hla = 0
DRB1*0414.hla + DRB1*0415.hla = 0
DRB1*0414.hla + DRB1*0416.hla = 0
DRB1*0414.hla + DRB1*0417.hla = 0
DRB1*0414.hla + DRB1*0418.hla = 0
DRB1*0414.hla + DRB1*0419.hla = 0
DRB1*0414.hla + DRB1*0420.hla = 0
DRB1*0414.hla + DRB1*0421.hla = 0
DRB1*0414.hla + DRB1*0422.hla = 0
DRB1*0415.hla + DRB1*0416.hla = 0
DRB1*0415.hla + DRB1*0417.hla = 0
DRB1*0415.hla + DRB1*0418.hla = 0
DRB1*0415.hla + DRB1*0419.hla = 0
DRB1*0415.hla + DRB1*0420.hla = 0
DRB1*0415.hla + DRB1*0421.hla = 0
DRB1*0415.hla + DRB1*0422.hla = 0
DRB1*0416.hla + DRB1*0417.hla = 0
DRB1*0416.hla + DRB1*0418.hla = 0
DRB1*0416.hla + DRB1*0419.hla = 0
DRB1*0416.hla + DRB1*0420.hla = 0
DRB1*0416.hla + DRB1*0421.hla = 0
DRB1*0416.hla + DRB1*0422.hla = 0
DRB1*0417.hla + DRB1*0418.hla = 0
DRB1*0417.hla + DRB1*0419.hla = 0
DRB1*0417.hla + DRB1*0420.hla = 0
DRB1*0417.hla + DRB1*0421.hla = 1
DRB1*0417.hla + DRB1*0422.hla = 0
DRB1*0418.hla + DRB1*0419.hla = 0
DRB1*0418.hla + DRB1*0420.hla = 0
DRB1*0418.hla + DRB1*0421.hla = 0
DRB1*0418.hla + DRB1*0422.hla = 0
DRB1*0419.hla + DRB1*0420.hla = 0
DRB1*0419.hla + DRB1*0421.hla = 0
DRB1*0419.hla + DRB1*0422.hla = 0
DRB1*0420.hla + DRB1*0421.hla = 0
DRB1*0420.hla + DRB1*0422.hla = 0
DRB1*0421.hla + DRB1*0422.hla = 0

Unique Sequences using AGT:

DRB1*0401.hla + DRB1*0402.hla = 0
DRB1*0401.hla + DRB1*0403.hla = 1
DRB1*0401.hla + DRB1*0404.hla = 1
DRB1*0401.hla + DRB1*0405.hla = 0
DRB1*0401.hla + DRB1*0406.hla = 3
DRB1*0401.hla + DRB1*0407.hla = 0
DRB1*0401.hla + DRB1*0408.hla = 0
DRB1*0401.hla + DRB1*0409.hla = 0
DRB1*0401.hla + DRB1*0410.hla = 0
DRB1*0401.hla + DRB1*0411.hla = 0
DRB1*0401.hla + DRB1*0412.hla = 0

- 131 -

Appendix 1 (cont'd)

DRB1*0401.hla + DRB1*0413.hla = 0
DRB1*0401.hla + DRB1*0414.hla = 0
DRB1*0401.hla + DRB1*0415.hla = 0
DRB1*0401.hla + DRB1*0416.hla = 0
DRB1*0401.hla + DRB1*0417.hla = 0
DRB1*0401.hla + DRB1*0418.hla = 0
DRB1*0401.hla + DRB1*0419.hla = 3
DRB1*0401.hla + DRB1*0420.hla = 3
DRB1*0401.hla + DRB1*0421.hla = 0
DRB1*0401.hla + DRB1*0422.hla = 0
DRB1*0402.hla + DRB1*0403.hla = 1
DRB1*0402.hla + DRB1*0404.hla = 1
DRB1*0402.hla + DRB1*0405.hla = 0
DRB1*0402.hla + DRB1*0406.hla = 0
DRB1*0402.hla + DRB1*0407.hla = 0
DRB1*0402.hla + DRB1*0408.hla = 2
DRB1*0402.hla + DRB1*0409.hla = 0
DRB1*0402.hla + DRB1*0410.hla = 0
DRB1*0402.hla + DRB1*0411.hla = 0
DRB1*0402.hla + DRB1*0412.hla = 0
DRB1*0402.hla + DRB1*0413.hla = 0
DRB1*0402.hla + DRB1*0414.hla = 0
DRB1*0402.hla + DRB1*0415.hla = 0
DRB1*0402.hla + DRB1*0416.hla = 0
DRB1*0402.hla + DRB1*0417.hla = 0
DRB1*0402.hla + DRB1*0418.hla = 0
DRB1*0402.hla + DRB1*0419.hla = 1
DRB1*0402.hla + DRB1*0420.hla = 1
DRB1*0402.hla + DRB1*0421.hla = 0
DRB1*0402.hla + DRB1*0422.hla = 0
DRB1*0403.hla + DRB1*0404.hla = 0
DRB1*0403.hla + DRB1*0405.hla = 2
DRB1*0403.hla + DRB1*0406.hla = 0
DRB1*0403.hla + DRB1*0407.hla = 0
DRB1*0403.hla + DRB1*0408.hla = 1
DRB1*0403.hla + DRB1*0409.hla = 1
DRB1*0403.hla + DRB1*0410.hla = 1
DRB1*0403.hla + DRB1*0411.hla = 0
DRB1*0403.hla + DRB1*0412.hla = 0
DRB1*0403.hla + DRB1*0413.hla = 1
DRB1*0403.hla + DRB1*0414.hla = 2
DRB1*0403.hla + DRB1*0415.hla = 1
DRB1*0403.hla + DRB1*0416.hla = 1
DRB1*0403.hla + DRB1*0417.hla = 0
DRB1*0403.hla + DRB1*0418.hla = 0
DRB1*0403.hla + DRB1*0419.hla = 3
DRB1*0403.hla + DRB1*0420.hla = 1
DRB1*0403.hla + DRB1*0421.hla = 3
DRB1*0403.hla + DRB1*0422.hla = 0
DRB1*0404.hla + DRB1*0405.hla = 2
DRB1*0404.hla + DRB1*0406.hla = 0
DRB1*0404.hla + DRB1*0407.hla = 0
DRB1*0404.hla + DRB1*0408.hla = 1
DRB1*0404.hla + DRB1*0409.hla = 1
DRB1*0404.hla + DRB1*0410.hla = 1
DRB1*0404.hla + DRB1*0411.hla = 0
DRB1*0404.hla + DRB1*0412.hla = 0
DRB1*0404.hla + DRB1*0413.hla = 1
DRB1*0404.hla + DRB1*0414.hla = 2
DRB1*0404.hla + DRB1*0415.hla = 1
DRB1*0404.hla + DRB1*0416.hla = 1

Appendix 1 (cont'd)

```
DRB1*0404.hla + DRB1*0417.hla = 0
DRB1*0404.hla + DRB1*0418.hla = 0
DRB1*0404.hla + DRB1*0419.hla = 3
DRB1*0404.hla + DRB1*0420.hla = 3
DRB1*0404.hla + DRB1*0421.hla = 3
DRB1*0404.hla + DRB1*0422.hla = 0
DRB1*0405.hla + DRB1*0406.hla = 0
DRB1*0405.hla + DRB1*0407.hla = 0
DRB1*0405.hla + DRB1*0408.hla = 0
DRB1*0405.hla + DRB1*0409.hla = 0
DRB1*0405.hla + DRB1*0410.hla = 0
DRB1*0405.hla + DRB1*0411.hla = 0
DRB1*0405.hla + DRB1*0412.hla = 0
DRB1*0405.hla + DRB1*0413.hla = 0
DRB1*0405.hla + DRB1*0414.hla = 0
DRB1*0405.hla + DRB1*0415.hla = 0
DRB1*0405.hla + DRB1*0416.hla = 0
DRB1*0405.hla + DRB1*0417.hla = 0
DRB1*0405.hla + DRB1*0418.hla = 0
DRB1*0405.hla + DRB1*0419.hla = 1
DRB1*0405.hla + DRB1*0420.hla = 1
DRB1*0405.hla + DRB1*0421.hla = 0
DRB1*0405.hla + DRB1*0422.hla = 0
DRB1*0406.hla + DRB1*0407.hla = 0
DRB1*0406.hla + DRB1*0408.hla = 0
DRB1*0406.hla + DRB1*0409.hla = 0
DRB1*0406.hla + DRB1*0410.hla = 0
DRB1*0406.hla + DRB1*0411.hla = 0
DRB1*0406.hla + DRB1*0412.hla = 0
DRB1*0406.hla + DRB1*0413.hla = 0
DRB1*0406.hla + DRB1*0414.hla = 0
DRB1*0406.hla + DRB1*0415.hla = 0
DRB1*0406.hla + DRB1*0416.hla = 0
DRB1*0406.hla + DRB1*0417.hla = 0
DRB1*0406.hla + DRB1*0418.hla = 0
DRB1*0406.hla + DRB1*0419.hla = 3
DRB1*0406.hla + DRB1*0420.hla = 1
DRB1*0406.hla + DRB1*0421.hla = 3
DRB1*0406.hla + DRB1*0422.hla = 0
DRB1*0407.hla + DRB1*0408.hla = 0
DRB1*0407.hla + DRB1*0409.hla = 0
DRB1*0407.hla + DRB1*0410.hla = 2
DRB1*0407.hla + DRB1*0411.hla = 0
DRB1*0407.hla + DRB1*0412.hla = 0
DRB1*0407.hla + DRB1*0413.hla = 0
DRB1*0407.hla + DRB1*0414.hla = 0
DRB1*0407.hla + DRB1*0415.hla = 0
DRB1*0407.hla + DRB1*0416.hla = 0
DRB1*0407.hla + DRB1*0417.hla = 0
DRB1*0407.hla + DRB1*0418.hla = 0
DRB1*0407.hla + DRB1*0419.hla = 0
DRB1*0407.hla + DRB1*0420.hla = 0
DRB1*0407.hla + DRB1*0421.hla = 0
DRB1*0407.hla + DRB1*0422.hla = 0
DRB1*0408.hla + DRB1*0409.hla = 0
DRB1*0408.hla + DRB1*0410.hla = 0
DRB1*0408.hla + DRB1*0411.hla = 0
DRB1*0408.hla + DRB1*0412.hla = 0
DRB1*0408.hla + DRB1*0413.hla = 0
DRB1*0408.hla + DRB1*0414.hla = 0
DRB1*0408.hla + DRB1*0415.hla = 0
```

- 133 -

Appendix 1 (cont'd)

```
DRB1*0408.hla + DRB1*0416.hla = 0
DRB1*0408.hla + DRB1*0417.hla = 0
DRB1*0408.hla + DRB1*0418.hla = 0
DRB1*0408.hla + DRB1*0419.hla = 0
DRB1*0408.hla + DRB1*0420.hla = 0
DRB1*0408.hla + DRB1*0421.hla = 0
DRB1*0408.hla + DRB1*0422.hla = 0
DRB1*0409.hla + DRB1*0410.hla = 0
DRB1*0409.hla + DRB1*0411.hla = 0
DRB1*0409.hla + DRB1*0412.hla = 0
DRB1*0409.hla + DRB1*0413.hla = 0
DRB1*0409.hla + DRB1*0414.hla = 0
DRB1*0409.hla + DRB1*0415.hla = 0
DRB1*0409.hla + DRB1*0416.hla = 0
DRB1*0409.hla + DRB1*0417.hla = 0
DRB1*0409.hla + DRB1*0418.hla = 0
DRB1*0409.hla + DRB1*0419.hla = 0
DRB1*0409.hla + DRB1*0420.hla = 0
DRB1*0409.hla + DRB1*0421.hla = 0
DRB1*0409.hla + DRB1*0422.hla = 0
DRB1*0410.hla + DRB1*0411.hla = 0
DRB1*0410.hla + DRB1*0412.hla = 0
DRB1*0410.hla + DRB1*0413.hla = 0
DRB1*0410.hla + DRB1*0414.hla = 0
DRB1*0410.hla + DRB1*0415.hla = 0
DRB1*0410.hla + DRB1*0416.hla = 0
DRB1*0410.hla + DRB1*0417.hla = 0
DRB1*0410.hla + DRB1*0418.hla = 0
DRB1*0410.hla + DRB1*0419.hla = 1
DRB1*0410.hla + DRB1*0420.hla = 1
DRB1*0410.hla + DRB1*0421.hla = 0
DRB1*0410.hla + DRB1*0422.hla = 0
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 0
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 0
DRB1*0411.hla + DRB1*0420.hla = 0
DRB1*0411.hla + DRB1*0421.hla = 0
DRB1*0411.hla + DRB1*0422.hla = 0
DRB1*0412.hla + DRB1*0413.hla = 0
DRB1*0412.hla + DRB1*0414.hla = 0
DRB1*0412.hla + DRB1*0415.hla = 0
DRB1*0412.hla + DRB1*0416.hla = 0
DRB1*0412.hla + DRB1*0417.hla = 0
DRB1*0412.hla + DRB1*0418.hla = 0
DRB1*0412.hla + DRB1*0419.hla = 0
DRB1*0412.hla + DRB1*0420.hla = 0
DRB1*0412.hla + DRB1*0421.hla = 0
DRB1*0412.hla + DRB1*0422.hla = 0
DRB1*0413.hla + DRB1*0414.hla = 0
DRB1*0413.hla + DRB1*0415.hla = 0
DRB1*0413.hla + DRB1*0416.hla = 0
DRB1*0413.hla + DRB1*0417.hla = 0
DRB1*0413.hla + DRB1*0418.hla = 0
DRB1*0413.hla + DRB1*0419.hla = 1
DRB1*0413.hla + DRB1*0420.hla = 1
DRB1*0413.hla + DRB1*0421.hla = 0
```

- 134 -

Appendix 1 (cont'd)

DRB1*0413.hla + DRB1*0422.hla = 0
DRB1*0414.hla + DRB1*0415.hla = 0
DRB1*0414.hla + DRB1*0416.hla = 0
DRB1*0414.hla + DRB1*0417.hla = 0
DRB1*0414.hla + DRB1*0418.hla = 0
DRB1*0414.hla + DRB1*0419.hla = 0
DRB1*0414.hla + DRB1*0420.hla = 0
DRB1*0414.hla + DRB1*0421.hla = 0
DRB1*0414.hla + DRB1*0422.hla = 0
DRB1*0415.hla + DRB1*0416.hla = 0
DRB1*0415.hla + DRB1*0417.hla = 0
DRB1*0415.hla + DRB1*0418.hla = 0
DRB1*0415.hla + DRB1*0419.hla = 1
DRB1*0415.hla + DRB1*0420.hla = 1
DRB1*0415.hla + DRB1*0421.hla = 0
DRB1*0415.hla + DRB1*0422.hla = 0
DRB1*0416.hla + DRB1*0417.hla = 0
DRB1*0416.hla + DRB1*0418.hla = 0
DRB1*0416.hla + DRB1*0419.hla = 0
DRB1*0416.hla + DRB1*0420.hla = 0
DRB1*0416.hla + DRB1*0421.hla = 0
DRB1*0416.hla + DRB1*0422.hla = 0
DRB1*0417.hla + DRB1*0418.hla = 0
DRB1*0417.hla + DRB1*0419.hla = 0
DRB1*0417.hla + DRB1*0420.hla = 0
DRB1*0417.hla + DRB1*0421.hla = 0
DRB1*0417.hla + DRB1*0422.hla = 0
DRB1*0418.hla + DRB1*0419.hla = 0
DRB1*0418.hla + DRB1*0420.hla = 0
DRB1*0418.hla + DRB1*0421.hla = 0
DRB1*0418.hla + DRB1*0422.hla = 0
DRB1*0419.hla + DRB1*0420.hla = 0
DRB1*0419.hla + DRB1*0421.hla = 3
DRB1*0419.hla + DRB1*0422.hla = 0
DRB1*0420.hla + DRB1*0421.hla = 3
DRB1*0420.hla + DRB1*0422.hla = 0
DRB1*0421.hla + DRB1*0422.hla = 0

Unique Sequences using ACGT:

DRB1*0401.hla + DRB1*0402.hla = 0
DRB1*0401.hla + DRB1*0403.hla = 0
DRB1*0401.hla + DRB1*0404.hla = 0
DRB1*0401.hla + DRB1*0405.hla = 0
DRB1*0401.hla + DRB1*0406.hla = 1
DRB1*0401.hla + DRB1*0407.hla = 0
DRB1*0401.hla + DRB1*0408.hla = 0
DRB1*0401.hla + DRB1*0409.hla = 0
DRB1*0401.hla + DRB1*0410.hla = 0
DRB1*0401.hla + DRB1*0411.hla = 0
DRB1*0401.hla + DRB1*0412.hla = 0
DRB1*0401.hla + DRB1*0413.hla = 0
DRB1*0401.hla + DRB1*0414.hla = 0
DRB1*0401.hla + DRB1*0415.hla = 0
DRB1*0401.hla + DRB1*0416.hla = 0
DRB1*0401.hla + DRB1*0417.hla = 0
DRB1*0401.hla + DRB1*0418.hla = 0
DRB1*0401.hla + DRB1*0419.hla = 0
DRB1*0401.hla + DRB1*0420.hla = 0
DRB1*0401.hla + DRB1*0421.hla = 0
DRB1*0401.hla + DRB1*0422.hla = 0

Appendix 1 (cont'd)

DRB1*0402.hla + DRB1*0403.hla = 0
DRB1*0402.hla + DRB1*0404.hla = 0
DRB1*0402.hla + DRB1*0405.hla = 0
DRB1*0402.hla + DRB1*0406.hla = 0
DRB1*0402.hla + DRB1*0407.hla = 0
DRB1*0402.hla + DRB1*0408.hla = 1
DRB1*0402.hla + DRB1*0409.hla = 0
DRB1*0402.hla + DRB1*0410.hla = 0
DRB1*0402.hla + DRB1*0411.hla = 0
DRB1*0402.hla + DRB1*0412.hla = 0
DRB1*0402.hla + DRB1*0413.hla = 0
DRB1*0402.hla + DRB1*0414.hla = 0
DRB1*0402.hla + DRB1*0415.hla = 0
DRB1*0402.hla + DRB1*0416.hla = 0
DRB1*0402.hla + DRB1*0417.hla = 0
DRB1*0402.hla + DRB1*0418.hla = 0
DRB1*0402.hla + DRB1*0419.hla = 0
DRB1*0402.hla + DRB1*0420.hla = 0
DRB1*0402.hla + DRB1*0421.hla = 0
DRB1*0402.hla + DRB1*0422.hla = 0
DRB1*0403.hla + DRB1*0404.hla = 0
DRB1*0403.hla + DRB1*0405.hla = 1
DRB1*0403.hla + DRB1*0406.hla = 0
DRB1*0403.hla + DRB1*0407.hla = 0
DRB1*0403.hla + DRB1*0408.hla = 0
DRB1*0403.hla + DRB1*0409.hla = 0
DRB1*0403.hla + DRB1*0410.hla = 0
DRB1*0403.hla + DRB1*0411.hla = 0
DRB1*0403.hla + DRB1*0412.hla = 0
DRB1*0403.hla + DRB1*0413.hla = 0
DRB1*0403.hla + DRB1*0414.hla = 0
DRB1*0403.hla + DRB1*0415.hla = 0
DRB1*0403.hla + DRB1*0416.hla = 0
DRB1*0403.hla + DRB1*0417.hla = 0
DRB1*0403.hla + DRB1*0418.hla = 0
DRB1*0403.hla + DRB1*0419.hla = 0
DRB1*0403.hla + DRB1*0420.hla = 0
DRB1*0403.hla + DRB1*0421.hla = 1
DRB1*0403.hla + DRB1*0422.hla = 0
DRB1*0404.hla + DRB1*0405.hla = 0
DRB1*0404.hla + DRB1*0406.hla = 0
DRB1*0404.hla + DRB1*0407.hla = 0
DRB1*0404.hla + DRB1*0408.hla = 0
DRB1*0404.hla + DRB1*0409.hla = 0
DRB1*0404.hla + DRB1*0410.hla = 0
DRB1*0404.hla + DRB1*0411.hla = 0
DRB1*0404.hla + DRB1*0412.hla = 0
DRB1*0404.hla + DRB1*0413.hla = 0
DRB1*0404.hla + DRB1*0414.hla = 1
DRB1*0404.hla + DRB1*0415.hla = 0
DRB1*0404.hla + DRB1*0416.hla = 0
DRB1*0404.hla + DRB1*0417.hla = 0
DRB1*0404.hla + DRB1*0418.hla = 0
DRB1*0404.hla + DRB1*0419.hla = 0
DRB1*0404.hla + DRB1*0420.hla = 0
DRB1*0404.hla + DRB1*0421.hla = 0
DRB1*0404.hla + DRB1*0422.hla = 0
DRB1*0405.hla + DRB1*0406.hla = 0
DRB1*0405.hla + DRB1*0407.hla = 0
DRB1*0405.hla + DRB1*0408.hla = 0
DRB1*0405.hla + DRB1*0409.hla = 0

Appendix 1 (cont'd)

DRB1*0405.hla + DRB1*0410.hla = 0
DRB1*0405.hla + DRB1*0411.hla = 0
DRB1*0405.hla + DRB1*0412.hla = 0
DRB1*0405.hla + DRB1*0413.hla = 0
DRB1*0405.hla + DRB1*0414.hla = 0
DRB1*0405.hla + DRB1*0415.hla = 0
DRB1*0405.hla + DRB1*0416.hla = 0
DRB1*0405.hla + DRB1*0417.hla = 0
DRB1*0405.hla + DRB1*0418.hla = 0
DRB1*0405.hla + DRB1*0419.hla = 0
DRB1*0405.hla + DRB1*0420.hla = 0
DRB1*0405.hla + DRB1*0421.hla = 0
DRB1*0405.hla + DRB1*0422.hla = 0
DRB1*0406.hla + DRB1*0407.hla = 0
DRB1*0406.hla + DRB1*0408.hla = 0
DRB1*0406.hla + DRB1*0409.hla = 0
DRB1*0406.hla + DRB1*0410.hla = 0
DRB1*0406.hla + DRB1*0411.hla = 0
DRB1*0406.hla + DRB1*0412.hla = 0
DRB1*0406.hla + DRB1*0413.hla = 0
DRB1*0406.hla + DRB1*0414.hla = 0
DRB1*0406.hla + DRB1*0415.hla = 0
DRB1*0406.hla + DRB1*0416.hla = 0
DRB1*0406.hla + DRB1*0417.hla = 0
DRB1*0406.hla + DRB1*0418.hla = 0
DRB1*0406.hla + DRB1*0419.hla = 0
DRB1*0406.hla + DRB1*0420.hla = 0
DRB1*0406.hla + DRB1*0421.hla = 0
DRB1*0406.hla + DRB1*0422.hla = 0
DRB1*0407.hla + DRB1*0408.hla = 0
DRB1*0407.hla + DRB1*0409.hla = 0
DRB1*0407.hla + DRB1*0410.hla = 1
DRB1*0407.hla + DRB1*0411.hla = 0
DRB1*0407.hla + DRB1*0412.hla = 0
DRB1*0407.hla + DRB1*0413.hla = 0
DRB1*0407.hla + DRB1*0414.hla = 0
DRB1*0407.hla + DRB1*0415.hla = 0
DRB1*0407.hla + DRB1*0416.hla = 0
DRB1*0407.hla + DRB1*0417.hla = 0
DRB1*0407.hla + DRB1*0418.hla = 0
DRB1*0407.hla + DRB1*0419.hla = 0
DRB1*0407.hla + DRB1*0420.hla = 0
DRB1*0407.hla + DRB1*0421.hla = 0
DRB1*0407.hla + DRB1*0422.hla = 0
DRB1*0408.hla + DRB1*0409.hla = 0
DRB1*0408.hla + DRB1*0410.hla = 0
DRB1*0408.hla + DRB1*0411.hla = 0
DRB1*0408.hla + DRB1*0412.hla = 0
DRB1*0408.hla + DRB1*0413.hla = 0
DRB1*0408.hla + DRB1*0414.hla = 0
DRB1*0408.hla + DRB1*0415.hla = 0
DRB1*0408.hla + DRB1*0416.hla = 0
DRB1*0408.hla + DRB1*0417.hla = 0
DRB1*0408.hla + DRB1*0418.hla = 0
DRB1*0408.hla + DRB1*0419.hla = 0
DRB1*0408.hla + DRB1*0420.hla = 0
DRB1*0408.hla + DRB1*0421.hla = 0
DRB1*0408.hla + DRB1*0422.hla = 0
DRB1*0409.hla + DRB1*0410.hla = 0
DRB1*0409.hla + DRB1*0411.hla = 0
DRB1*0409.hla + DRB1*0412.hla = 0

Appendix 1 (cont'd)

DRB1*0409.hla + DRB1*0413.hla = 0
DRB1*0409.hla + DRB1*0414.hla = 0
DRB1*0409.hla + DRB1*0415.hla = 0
DRB1*0409.hla + DRB1*0416.hla = 0
DRB1*0409.hla + DRB1*0417.hla = 0
DRB1*0409.hla + DRB1*0418.hla = 0
DRB1*0409.hla + DRB1*0419.hla = 0
DRB1*0409.hla + DRB1*0420.hla = 0
DRB1*0409.hla + DRB1*0421.hla = 0
DRB1*0409.hla + DRB1*0422.hla = 0
DRB1*0410.hla + DRB1*0411.hla = 0
DRB1*0410.hla + DRB1*0412.hla = 0
DRB1*0410.hla + DRB1*0413.hla = 0
DRB1*0410.hla + DRB1*0414.hla = 0
DRB1*0410.hla + DRB1*0415.hla = 0
DRB1*0410.hla + DRB1*0416.hla = 0
DRB1*0410.hla + DRB1*0417.hla = 0
DRB1*0410.hla + DRB1*0418.hla = 0
DRB1*0410.hla + DRB1*0419.hla = 0
DRB1*0410.hla + DRB1*0420.hla = 0
DRB1*0410.hla + DRB1*0421.hla = 0
DRB1*0410.hla + DRB1*0422.hla = 0
DRB1*0411.hla + DRB1*0412.hla = 0
DRB1*0411.hla + DRB1*0413.hla = 0
DRB1*0411.hla + DRB1*0414.hla = 0
DRB1*0411.hla + DRB1*0415.hla = 0
DRB1*0411.hla + DRB1*0416.hla = 0
DRB1*0411.hla + DRB1*0417.hla = 0
DRB1*0411.hla + DRB1*0418.hla = 0
DRB1*0411.hla + DRB1*0419.hla = 0
DRB1*0411.hla + DRB1*0420.hla = 0
DRB1*0411.hla + DRB1*0421.hla = 0
DRB1*0411.hla + DRB1*0422.hla = 0
DRB1*0412.hla + DRB1*0413.hla = 0
DRB1*0412.hla + DRB1*0414.hla = 0
DRB1*0412.hla + DRB1*0415.hla = 0
DRB1*0412.hla + DRB1*0416.hla = 0
DRB1*0412.hla + DRB1*0417.hla = 0
DRB1*0412.hla + DRB1*0418.hla = 0
DRB1*0412.hla + DRB1*0419.hla = 0
DRB1*0412.hla + DRB1*0420.hla = 0
DRB1*0412.hla + DRB1*0421.hla = 0
DRB1*0412.hla + DRB1*0422.hla = 0
DRB1*0413.hla + DRB1*0414.hla = 0
DRB1*0413.hla + DRB1*0415.hla = 0
DRB1*0413.hla + DRB1*0416.hla = 0
DRB1*0413.hla + DRB1*0417.hla = 0
DRB1*0413.hla + DRB1*0418.hla = 0
DRB1*0413.hla + DRB1*0419.hla = 0
DRB1*0413.hla + DRB1*0420.hla = 0
DRB1*0413.hla + DRB1*0421.hla = 0
DRB1*0413.hla + DRB1*0422.hla = 0
DRB1*0414.hla + DRB1*0415.hla = 0
DRB1*0414.hla + DRB1*0416.hla = 0
DRB1*0414.hla + DRB1*0417.hla = 0
DRB1*0414.hla + DRB1*0418.hla = 0
DRB1*0414.hla + DRB1*0419.hla = 0
DRB1*0414.hla + DRB1*0420.hla = 0
DRB1*0414.hla + DRB1*0421.hla = 0
DRB1*0414.hla + DRB1*0422.hla = 0
DRB1*0415.hla + DRB1*0416.hla = 0

DRB1*0415.hla + DRB1*0417.hla = 0
DRB1*0415.hla + DRB1*0418.hla = 0
DRB1*0415.hla + DRB1*0419.hla = 0
DRB1*0415.hla + DRB1*0420.hla = 0
DRB1*0415.hla + DRB1*0421.hla = 0
DRB1*0415.hla + DRB1*0422.hla = 0
DRB1*0416.hla + DRB1*0417.hla = 0
DRB1*0416.hla + DRB1*0418.hla = 0
DRB1*0416.hla + DRB1*0419.hla = 0
DRB1*0416.hla + DRB1*0420.hla = 0
DRB1*0416.hla + DRB1*0421.hla = 0
DRB1*0416.hla + DRB1*0422.hla = 0
DRB1*0417.hla + DRB1*0418.hla = 0
DRB1*0417.hla + DRB1*0419.hla = 0
DRB1*0417.hla + DRB1*0420.hla = 0
DRB1*0417.hla + DRB1*0421.hla = 0
DRB1*0417.hla + DRB1*0422.hla = 0
DRB1*0418.hla + DRB1*0419.hla = 0
DRB1*0418.hla + DRB1*0420.hla = 0
DRB1*0418.hla + DRB1*0421.hla = 0
DRB1*0418.hla + DRB1*0422.hla = 0
DRB1*0419.hla + DRB1*0420.hla = 0
DRB1*0419.hla + DRB1*0421.hla = 0
DRB1*0419.hla + DRB1*0422.hla = 0
DRB1*0420.hla + DRB1*0421.hla = 0
DRB1*0420.hla + DRB1*0422.hla = 0
DRB1*0421.hla + DRB1*0422.hla = 0

Appendix 2

HLA Class I C locus: allele analysis on the basis of exons 2 and 3.

Sequences obtained from the Strasbourg Data Base
Internet Address = ftp://FTP.EMBL-Heidelberg.DE/pub/databases

35 known alleles for HLA Class I C locus.

1: Cw*0101.hla
2: Cw*0102.hla
3: Cw*0201.hla
4: Cw*02021.hla
5: Cw*02022.hla
6: Cw*0301.hla
7: Cw*0302.hla
8: Cw*0303.hla
9: Cw*0304.hla
10: Cw*0401.hla
11: Cw*0402.hla
12: Cw*0501.hla
13: Cw*0602.hla
14: Cw*0702.hla
15: Cw*0701.hla
16: Cw*0703.hla
17: Cw*0704.hla
18: Cw*0801.hla
19: Cw*0802.hla
20: Cw*0803.hla
21: Cw*1201.hla
22: Cw*12021.hla
23: Cw*12022.hla
24: Cw*1203.hla
25: Cw*1301.hla
26: Cw*1402.hla
27: Cw*1403.hla 28: Cw*1501.hla
29: Cw*1502.hla
30: Cw*1503.hla
31: Cw*1505.hla
32: Cw*1504.hla
33: Cw*1601.hla
34: Cw*1602.hla
35: Cw*1701.hla

35 alleles may be combined as 35 homozygous pairs or 630 heterozygous pairs.

Homozygous pairs may be distinguished by single nucleotide sequencing in the following order:

Non-Unique Sequences using A:
Cw*0102.hla = (Cw*0102.hla)
Cw*0101.hla = (Cw*0101.hla)
Cw*0701.hla = (Cw*0701.hla)
Cw*0702.hla = (Cw*0702.hla)
Cw*12022.hla = (Cw*12022.hla, Cw*1203.hla) Cw*12021.hla = (Cw*12021.hla, Cw*1203.hla) Cw*12021.hla = (Cw*12021.hla, Cw*12022.hla) Cw*1503.hla = (Cw*1503.hla)
Cw*1502.hla = (Cw*1502.hla)
Cw*1504.hla = (Cw*1504.hla)
Cw*1505.hla = (Cw*1505.hla)

Unique Sequences using A:
1: Cw*0201.hla
2: Cw*02021.hla
3: Cw*02022.hla
4: Cw*0301.hla
5: Cw*0302.hla
6: Cw*0303.hla
7: Cw*0304.hla
8: Cw*0401.hla
9: Cw*0402.hla
10: Cw*0501.hla
11: Cw*0602.hla
12: Cw*0703.hla
13: Cw*0704.hla
14: Cw*0801.hla
15: Cw*0802.hla
16: Cw*0803.hla
17: Cw*1201.hla
18: Cw*1301.hla
19: Cw*1402.hla
20: Cw*1403.hla
21: Cw*1501.hla
22: Cw*1601.hla
23: Cw*1602.hla 24: Cw*1701.hla Non-Unique Sequences using C:
Cw*02022.hla = (Cw*02022.hla)
Cw*02021.hla = (Cw*02021.hla)
Cw*0304.hla = (Cw*0304.hla)
Cw*0303.hla = (Cw*0303.hla)
Cw*0802.hla = (Cw*0802.hla)
Cw*0803.hla = (Cw*0803.hla)
Cw*0501.hla = (Cw*0501.hla)
Cw*0801.hla = (Cw*0801.hla)
Cw*12022.hla = (Cw*12022.hla)
Cw*12021.hla = (Cw*12021.hla)
Cw*1504.hla = (Cw*1504.hla)
Cw*1403.hla = (Cw*1403.hla)
Cw*1402.hla = (Cw*1402.hla)
Cw*1503.hla = (Cw*1503.hla, Cw*1505.hla) Cw*1502.hla = (Cw*1502.hla, Cw*1505.hla) Cw*1502.hla = (Cw*1502.hla, Cw*1503.hla) Cw*1203.hla = (Cw*1203.hla)
Cw*1602.hla = (Cw*1602.hla)
Cw*1601.hla = (Cw*1601.hla)

Unique Sequences using C:
1: Cw*0101.hla
2: Cw*0102.hla
3: Cw*0201.hla
4: Cw*0301.hla
5: Cw*0302.hla
6: Cw*0401.hla
7: Cw*0402.hla
8: Cw*0602.hla
9: Cw*0702.hla
10: Cw*0701.hla
11: Cw*0703.hla
12: Cw*0704.hla
13: Cw*1201.hla
14: Cw*1301.hla
15: Cw*1501.hla
16: Cw*1701.hla Non-Unique Sequences using G:

Cw*02022.hla = (Cw*02022.hla)
Cw*02021.hla = (Cw*02021.hla)
Cw*0303.hla = (Cw*0303.hla, Cw*0304.hla, Cw*0801.hla, Cw*0803.hla, Cw*1601.hla, Cw*1602.hla)
Cw*0302.hla = (Cw*0302.hla, Cw*0304.hla, Cw*0801.hla, Cw*0803.hla, Cw*1601.hla, Cw*1602.hla)
Cw*0302.hla = (Cw*0302.hla, Cw*0303.hla, Cw*0801.hla, Cw*0803.hla, Cw*1601.hla, Cw*1602.hla)
Cw*12021.hla = (Cw*12021.hla, Cw*12022.hla, Cw*1203.hla, Cw*1301.hla)
Cw*0302.hla = (Cw*0302.hla, Cw*0303.hla, Cw*0304.hla, Cw*0803.hla, Cw*1601.hla, Cw*1602.hla)
Cw*1402.hla = (Cw*1402.hla, Cw*1403.hla) Cw*0302.hla = (Cw*0302.hla, Cw*0303.hla, Cw*0304.hla, Cw*0801.hla, Cw*1601.hla, Cw*1602.hla)
Cw*0401.hla = (Cw*0401.hla, Cw*12022.hla, Cw*1203.hla, Cw*1301.hla)
Cw*0401.hla = (Cw*0401.hla, Cw*12021.hla, Cw*1203.hla, Cw*1301.hla)
Cw*0401.hla = (Cw*0401.hla, Cw*12021.hla, Cw*12022.hla, Cw*1301.hla)
Cw*0401.hla = (Cw*0401.hla, Cw*12021.hla, Cw*12022.hla, Cw*1203.hla)
Cw*0802.hla = (Cw*0802.hla, Cw*1403.hla) Cw*0802.hla = (Cw*0802.hla, Cw*1402.hla) Cw*1502.hla = (Cw*1502.hla, Cw*1505.hla, Cw*1504.hla)
Cw*1501.hla = (Cw*1501.hla, Cw*1505.hla, Cw*1504.hla) Cw*1501.hla = (Cw*1501.hla, Cw*1502.hla, Cw*1504.hla) Cw*1501.hla = (Cw*1501.hla, Cw*1502.hla, Cw*1505.hla) Cw*0302.hla = (Cw*0302.hla, Cw*0303.hla, Cw*0304.hla, Cw*0801.hla, Cw*0803.hla, Cw*1602.hla)
Cw*0302.hla = (Cw*0302.hla, Cw*0303.hla, Cw*0304.hla, Cw*0801.hla, Cw*0803.hla, Cw*1601.hla)

Unique Sequences using G:
1: Cw*0101.hla
2: Cw*0102.hla
3: Cw*0201.hla
4: Cw*0301.hla
5: Cw*0402.hla
6: Cw*0501.hla
7: Cw*0602.hla
8: Cw*0702.hla
9: Cw*0701.hla
10: Cw*0703.hla
11: Cw*0704.hla
12: Cw*1201.hla
13: Cw*1503.hla
14: Cw*1701.hla

- 144 -

Non-Unique Sequences using T:
Cw*0102.hla = (Cw*0102.hla)
Cw*0101.hla = (Cw*0101.hla)
Cw*02021.hla = (Cw*02021.hla, Cw*02022.hla) Cw*0201.hla = (Cw*0201.hla,
Cw*02022.hla) Cw*0201.hla = (Cw*0201.hla, Cw*02021.hla) Cw*0303.hla =
(Cw*0303.hla, Cw*0304.hla) Cw*0302.hla = (Cw*0302.hla, Cw*0304.hla)
Cw*0302.hla = (Cw*0302.hla, Cw*0303.hla) Cw*0402.hla = (Cw*0402.hla)
Cw*0401.hla = (Cw*0401.hla)
Cw*0801.hla = (Cw*0801.hla, Cw*0802.hla, Cw*0803.hla) Cw*0701.hla =
(Cw*0701.hla)
Cw*0702.hla = (Cw*0702.hla)
Cw*0501.hla = (Cw*0501.hla, Cw*0802.hla, Cw*0803.hla) Cw*0501.hla =
(Cw*0501.hla, Cw*0801.hla, Cw*0803.hla) Cw*0501.hla = (Cw*0501.hla,
Cw*0801.hla, Cw*0802.hla) Cw*12022.hla = (Cw*12022.hla, Cw*1301.hla)
Cw*12021.hla = (Cw*12021.hla, Cw*1301.hla) Cw*12021.hla = (Cw*12021.hla,
Cw*12022.hla) Cw*1403.hla = (Cw*1403.hla)
Cw*1402.hla = (Cw*1402.hla)
Cw*1503.hla = (Cw*1503.hla, Cw*1505.hla) Cw*1502.hla = (Cw*1502.hla,
Cw*1505.hla) Cw*1502.hla = (Cw*1502.hla, Cw*1503.hla) Cw*1602.hla =
(Cw*1602.hla)
Cw*1601.hla = (Cw*1601.hla)

Unique Sequences using T:
1: Cw*0301.hla
2: Cw*0602.hla
3: Cw*0703.hla
4: Cw*0704.hla
5: Cw*1201.hla
6: Cw*1203.hla
7: Cw*1501.hla
8: Cw*1504.hla
9: Cw*1701.hla

Non-Unique Sequences using AC:
Cw*12022.hla = (Cw*12022.hla)
Cw*12021.hla = (Cw*12021.hla)
Cw*1503.hla = (Cw*1503.hla)
Cw*1502.hla = (Cw*1502.hla)

Unique Sequences using AC:

1: Cw*0101.hla
2: Cw*0102.hla
3: Cw*0201.hla
4: Cw*02021.hla
5: Cw*02022.hla
6: Cw*0301.hla
7: Cw*0302.hla
8: Cw*0303.hla
9: Cw*0304.hla
10: Cw*0401.hla
11: Cw*0402.hla
12: Cw*0501.hla
13: Cw*0602.hla
14: Cw*0702.hla
15: Cw*0701.hla
16: Cw*0703.hla
17: Cw*0704.hla
18: Cw*0801.hla
19: Cw*0802.hla
20: Cw*0803.hla
21: Cw*1201.hla
22: Cw*1203.hla
23: Cw*1301.hla
24: Cw*1402.hla
25: Cw*1403.hla
26: Cw*1501.hla
27: Cw*1505.hla
28: Cw*1504.hla
29: Cw*1601.hla
30: Cw*1602.hla
31: Cw*1701.hla

Non-Unique Sequences using AG:
Cw*12022.hla = (Cw*12022.hla, Cw*1203.hla) Cw*12021.hla = (Cw*12021.hla, Cw*1203.hla) Cw*12021.hla = (Cw*12021.hla, Cw*12022.hla) Cw*1504.hla = (Cw*1504.hla)
Cw*1505.hla = (Cw*1505.hla)

Unique Sequences using AG:
1: Cw*0101.hla
2: Cw*0102.hla

3: Cw*0201.hla
4: Cw*02021.hla
5: Cw*02022.hla
6: Cw*0301.hla
7: Cw*0302.hla
8: Cw*0303.hla
9: Cw*0304.hla
10: Cw*0401.hla
11: Cw*0402.hla
12: Cw*0501.hla
13: Cw*0602.hla
14: Cw*0702.hla
15: Cw*0701.hla
16: Cw*0703.hla
17: Cw*0704.hla
18: Cw*0801.hla
19: Cw*0802.hla
20: Cw*0803.hla
21: Cw*1201.hla
22: Cw*1301.hla
23: Cw*1402.hla
24: Cw*1403.hla
25: Cw*1501.hla
26: Cw*1502.hla
27: Cw*1503.hla
28: Cw*1601.hla
29: Cw*1602.hla
30: Cw*1701.hla Non-Unique Sequences using AT:
Cw*0102.hla = (Cw*0102.hla)
Cw*0101.hla = (Cw*0101.hla)
Cw*0701.hla = (Cw*0701.hla)
Cw*0702.hla = (Cw*0702.hla)
Cw*12022.hla = (Cw*12022.hla)
Cw*12021.hla = (Cw*12021.hla)
Cw*1503.hla = (Cw*1503.hla)
Cw*1502.hla = (Cw*1502.hla)

Unique Sequences using AT:
1: Cw*0201.hla

2: Cw*02021.hla
3: Cw*02022.hla
4: Cw*0301.hla
5: Cw*0302.hla
6: Cw*0303.hla
7: Cw*0304.hla
8: Cw*0401.hla
9: Cw*0402.hla
10: Cw*0501.hla
11: Cw*0602.hla
12: Cw*0703.hla
13: Cw*0704.hla
14: Cw*0801.hla
15: Cw*0802.hla
16: Cw*0803.hla
17: Cw*1201.hla
18: Cw*1203.hla
19: Cw*1301.hla
20: Cw*1402.hla
21: Cw*1403.hla
22: Cw*1501.hla
23: Cw*1505.hla
24: Cw*1504.hla
25: Cw*1601.hla
26: Cw*1602.hla
27: Cw*1701.hla Non-Unique Sequences using CG:
Cw*02022.hla = (Cw*02022.hla)
Cw*02021.hla = (Cw*02021.hla)
Cw*0304.hla = (Cw*0304.hla)
Cw*0303.hla = (Cw*0303.hla)
Cw*0803.hla = (Cw*0803.hla)
Cw*0801.hla = (Cw*0801.hla)
Cw*12022.hla = (Cw*12022.hla)
Cw*12021.hla = (Cw*12021.hla)
Cw*1403.hla = (Cw*1403.hla)
Cw*1402.hla = (Cw*1402.hla)
Cw*1505.hla = (Cw*1505.hla)
Cw*1502.hla = (Cw*1502.hla)
Cw*1602.hla = (Cw*1602.hla)

Cw*1601.hla = (Cw*1601.hla)

Unique Sequences using CG:
1: Cw*0101.hla
2: Cw*0102.hla
3: Cw*0201.hla
4: Cw*0301.hla
5: Cw*0302.hla
6: Cw*0401.hla
7: Cw*0402.hla
8: Cw*0501.hla
9: Cw*0602.hla
10: Cw*0702.hla
11: Cw*0701.hla
12: Cw*0703.hla
13: Cw*0704.hla
14: Cw*0802.hla
15: Cw*1201.hla
16: Cw*1203.hla
17: Cw*1301.hla
18: Cw*1501.hla
19: Cw*1503.hla
20: Cw*1504.hla
21: Cw*1701.hla

Non-Unique Sequences using CT:
Cw*02022.hla = (Cw*02022.hla)
Cw*02021.hla = (Cw*02021.hla)
Cw*0304.hla = (Cw*0304.hla)
Cw*0303.hla = (Cw*0303.hla)
Cw*0802.hla = (Cw*0802.hla)
Cw*0803.hla = (Cw*0803.hla)
Cw*0501.hla = (Cw*0501.hla)
Cw*0801.hla = (Cw*0801.hla)
Cw*12022.hla = (Cw*12022.hla)
Cw*12021.hla = (Cw*12021.hla)
Cw*1403.hla = (Cw*1403.hla)
Cw*1402.hla = (Cw*1402.hla)
Cw*1503.hla = (Cw*1503.hla, Cw*1505.hla) Cw*1502.hla = (Cw*1502.hla, Cw*1505.hla) Cw*1502.hla = (Cw*1502.hla, Cw*1503.hla) Cw*1602.hla = (Cw*1602.hla)

Cw*1601.hla = (Cw*1601.hla)

Unique Sequences using CT:
1: Cw*0101.hla
2: Cw*0102.hla
3: Cw*0201.hla
4: Cw*0301.hla
5: Cw*0302.hla
6: Cw*0401.hla
7: Cw*0402.hla
8: Cw*0602.hla
9: Cw*0702.hla
10: Cw*0701.hla
11: Cw*0703.hla
12: Cw*0704.hla
13: Cw*1201.hla
14: Cw*1203.hla
15: Cw*1301.hla
16: Cw*1501.hla
17: Cw*1504.hla
18: Cw*1701.hla

Non-Unique Sequences using GT:
Cw*02022.hla = (Cw*02022.hla)
Cw*02021.hla = (Cw*02021.hla)
Cw*0303.hla = (Cw*0303.hla, Cw*0304.hla) Cw*0302.hla = (Cw*0302.hla, Cw*0304.hla) Cw*0302.hla = (Cw*0302.hla, Cw*0303.hla) Cw*0803.hla = (Cw*0803.hla)
Cw*0801.hla = (Cw*0801.hla)
Cw*12022.hla = (Cw*12022.hla, Cw*1301.hla) Cw*12021.hla = (Cw*12021.hla, Cw*1301.hla) Cw*12021.hla = (Cw*12021.hla, Cw*12022.hla) Cw*1403.hla = (Cw*1403.hla)
Cw*1402.hla = (Cw*1402.hla)
Cw*1505.hla = (Cw*1505.hla)
Cw*1502.hla = (Cw*1502.hla)
Cw*1602.hla = (Cw*1602.hla)
Cw*1601.hla = (Cw*1601.hla)

Unique Sequences using GT:
1: Cw*0101.hla
2: Cw*0102.hla

3: Cw*0201.hla
4: Cw*0301.hla
5: Cw*0401.hla
6: Cw*0402.hla
7: Cw*0501.hla
8: Cw*0602.hla
9: Cw*0702.hla
10: Cw*0701.hla
11: Cw*0703.hla
12: Cw*0704.hla
13: Cw*0802.hla
14: Cw*1201.hla
15: Cw*1203.hla
16: Cw*1501.hla
17: Cw*1503.hla
18: Cw*1504.hla
19: Cw*1701.hla

Non-Unique Sequences using ACG:
Cw*12022.hla = (Cw*12022.hla)
Cw*12021.hla = (Cw*12021.hla)

Unique Sequences using ACG:
1: Cw*0101.hla
2: Cw*0102.hla
3: Cw*0201.hla
4: Cw*02021.hla
5: Cw*02022.hla
6: Cw*0301.hla
7: Cw*0302.hla
8: Cw*0303.hla
9: Cw*0304.hla
10: Cw*0401.hla
11: Cw*0402.hla
12: Cw*0501.hla
13: Cw*0602.hla
14: Cw*0702.hla
15: Cw*0701.hla
16: Cw*0703.hla
17: Cw*0704.hla
18: Cw*0801.hla 19: Cw*0802.hla
20: Cw*0803.hla
21: Cw*1201.hla
22: Cw*1203.hla
23: Cw*1301.hla
24: Cw*1402.hla
25: Cw*1403.hla
26: Cw*1501.hla
27: Cw*1502.hla
28: Cw*1503.hla
29: Cw*1505.hla
30: Cw*1504.hla
31: Cw*1601.hla
32: Cw*1602.hla
33: Cw*1701.hla

Non-Unique Sequences using ACT:
Cw*12022.hla = (Cw*12022.hla)
Cw*12021.hla = (Cw*12021.hla)
Cw*1503.hla = (Cw*1503.hla)
Cw*1502.hla = (Cw*1502.hla)

Unique Sequences using ACT:
1: Cw*0101.hla
2: Cw*0102.hla
3: Cw*0201.hla
4: Cw*02021.hla
5: Cw*02022.hla
6: Cw*0301.hla
7: Cw*0302.hla
8: Cw*0303.hla
9: Cw*0304.hla
10: Cw*0401.hla
11: Cw*0402.hla
12: Cw*0501.hla
13: Cw*0602.hla
14: Cw*0702.hla
15: Cw*0701.hla
16: Cw*0703.hla
17: Cw*0704.hla
18: Cw*0801.hla 19: Cw*0802.hla
20: Cw*0803.hla
21: Cw*1201.hla
22: Cw*1203.hla
23: Cw*1301.hla
24: Cw*1402.hla
25: Cw*1403.hla
26: Cw*1501.hla
27: Cw*1505.hla
28: Cw*1504.hla
29: Cw*1601.hla
30: Cw*1602.hla
31: Cw*1701.hla

Non-Unique Sequences using AGT:
Cw*12022.hla = (Cw*12022.hla)
Cw*12021.hla = (Cw*12021.hla)

Unique Sequences using AGT:
1: Cw*0101.hla
2: Cw*0102.hla
3: Cw*0201.hla
4: Cw*02021.hla
5: Cw*02022.hla
6: Cw*0301.hla
7: Cw*0302.hla
8: Cw*0303.hla
9: Cw*0304.hla
10: Cw*0401.hla
11: Cw*0402.hla
12: Cw*0501.hla
13: Cw*0602.hla
14: Cw*0702.hla
15: Cw*0701.hla
16: Cw*0703.hla
17: Cw*0704.hla
18: Cw*0801.hla
19: Cw*0802.hla
20: Cw*0803.hla
21: Cw*1201.hla
22: Cw*1203.hla 23: Cw*1301.hla
24: Cw*1402.hla
25: Cw*1403.hla
26: Cw*1501.hla
27: Cw*1502.hla
28: Cw*1503.hla
29: Cw*1505.hla
30: Cw*1504.hla
31: Cw*1601.hla
32: Cw*1602.hla
33: Cw*1701.hla Non-Unique Sequences using CGT:
Cw*02022.hla = (Cw*02022.hla)
Cw*02021.hla = (Cw*02021.hla)
Cw*0304.hla = (Cw*0304.hla)
Cw*0303.hla = (Cw*0303.hla)
Cw*0803.hla = (Cw*0803.hla)
Cw*0801.hla = (Cw*0801.hla)
Cw*12022.hla = (Cw*12022.hla)
Cw*12021.hla = (Cw*12021.hla)
Cw*1403.hla = (Cw*1403.hla)
Cw*1402.hla = (Cw*1402.hla)
Cw*1505.hla = (Cw*1505.hla)
Cw*1502.hla = (Cw*1502.hla)
Cw*1602.hla = (Cw*1602.hla)
Cw*1601.hla = (Cw*1601.hla)

Unique Sequences using CGT:
1: Cw*0101.hla
2: Cw*0102.hla
3: Cw*0201.hla
4: Cw*0301.hla
5: Cw*0302.hla
6: Cw*0401.hla
7: Cw*0402.hla
8: Cw*0501.hla
9: Cw*0602.hla
10: Cw*0702.hla
11: Cw*0701.hla
12: Cw*0703.hla 13: Cw*0704.hla
14: Cw*0802.hla
15: Cw*1201.hla
16: Cw*1203.hla
17: Cw*1301.hla
18: Cw*1501.hla
19: Cw*1503.hla
20: Cw*1504.hla
21: Cw*1701.hla Non-Unique Sequences using ACGT:
Cw*12022.hla = (Cw*12021.hla)
Cw*12021.hla = (Cw*12022.hla)

Unique Sequences using ACGT:
1: Cw*0101.hla
2: Cw*0102.hla
3: Cw*0201.hla
4: Cw*02021.hla
5: Cw*02022.hla
6: Cw*0301.hla
7: Cw*0302.hla
8: Cw*0303.hla
9: Cw*0304.hla
10: Cw*0401.hla
11: Cw*0402.hla
12: Cw*0501.hla
13: Cw*0602.hla
14: Cw*0702.hla
15: Cw*0701.hla
16: Cw*0703.hla
17: Cw*0704.hla
18: Cw*0801.hla
19: Cw*0802.hla
20: Cw*0803.hla
21: Cw*1201.hla
22: Cw*1203.hla
23: Cw*1301.hla
24: Cw*1402.hla
25: Cw*1403.hla
26: Cw*1501.hla 27: Cw*1502.hla
28: Cw*1503.hla
29: Cw*1505.hla
30: Cw*1504.hla
31: Cw*1601.hla
32: Cw*1602.hla
33: Cw*1701.hla

Appendix 3

HLA Class 1C, Exon 3

Unique Sequences using A:
```
1: Cw*0201 ................................-A-.......................A.........................
   ........-A-.......................................................A..........................
2: Cw*0301 .........-A-........................................................A................
   ........A.......................................................................A...........
3: Cw*0302 ...........................-A-....................................................A..
4: Cw*0703 ..................-A-........................................A.....................
5: Cw*0704 ..............................................A.................................
   -A-.....................................................A.........................
6: Cw*0801 ............-A-.........................A.............................A...........
   -A-.....................................................................A...............
7: Cw*0803 ..................-A-............................A.....................A..........
8: Cw*1701 ...........-A-.......................A...............................A..............
```

Unique Sequences using C:
```
1: Cw*0101 ..................C..............C.....................C.....
2: Cw*0102 .........C.......................................................
```

Appendix 3: HLA Class I C locus Exon 3 (cont'd)

Appendix 3: HLA Class I C locus Exon 3 (cont'd)

Unique Sequences using G:
1: Cw*0101
2: Cw*0102
3: Cw*0402
4: Cw*0501
5: Cw*0704
6: Cw*1201
7: Cw*1701

Unique Sequences using T:
1: Cw*0301
2: Cw*0602

Appendix 3: HLA Class I C locus Exon 3 (cont'd)

```
                                               160
3: Cw*0703   ...........................................................................
             ...........................................................................
4: Cw*0704   .....T.................................................................
             ...........................................................................
5: Cw*1201   ...........................................................T.............
             ......T...................................................................
6: Cw*1203   ..................................................T.......T.............
             ...T........................................................................
7: Cw*1504   ........T..................................................T.............
             ...........................................................................
8: Cw*1701   .........T..............T.................................................
             ...T........................................................................

Unique Sequences using AC:
1: Cw*0101   ........C...................C........A.................................
             .....C......................................................................
2: Cw*0102   ........C...................C........A.................................
             ...........................................................................
3: Cw*0201   ........C...................C........A..............C..................A
             ........A..................................................................
4: Cw*0301   ...........................................................................

- 160 -
```

Appendix 3: HLA Class I C locus Exon 3 (cont'd)

```
                                                                                                                    A
     .....A........................................C...............A.................C........................
     ....C.....A........................................................................................C........
 5: Cw*0302
     .......C........................................C.................A.........................C................
 6: Cw*0702
     ....C...........................C...............C..................C..............C.........................
 7: Cw*0701
     ....C...........................C................................C..............C..........................
 8: Cw*0703
     ....C...........................C................................C..............C......AC....................
 9: Cw*0704
     ....C...........................C................C...............C..........AC...........................
10: Cw*0801
     .A..............................C................A..........A.............................................
11: Cw*0803
     .A..C...........................C................AC.............A..............A............................A
12: Cw*1201
     .A..............................C................AC..............A............................................
13: Cw*1501
     ....C.....A.....................C.................................A..............C...............A..........
     ....C...........................C.................................................................C............
14: Cw*1505
```

- 161 -

Appendix 3: HLA Class I C locus Exon 3 (cont'd)

Appendix 3: HLA Class I C locus Exon 3 (cont'd)

```
8:  Cw*0501  ................................A........A.G...A..................
9:  Cw*0703  .....A..........................A........A..G......G...............
10: Cw*0704  ..A.............................A........GA........................
11: Cw*0801  ................................A........A.........................
12: Cw*0802  ..A.............................A........A..G......A...............
13: Cw*0803  ..A.............................A........A.........................A..
14: Cw*1201  ..A.............................A........A...G.....G...............
15: Cw*1701  ..A.............................A........A.........GA.............G...
```

We claim:

1. A method for identification of allelic type of a known polymorphic genetic locus in a sample comprising the steps of:
   (a) combining the sample with one or more sequencing reaction mixtures containing a template-dependent nucleic acid polymerase, A, T, G and C nucleotide feedstocks, at least one type of chain terminating nucleotide and a sequencing primer under conditions suitable for template dependant primer extension to form a plurality of oligonucleotide fragments of differing lengths, the lengths of said fragments indicating the positions of the type of base corresponding to the chain terminating nucleotide incorporated in the extended primer, wherein the sample is concurrently combined with one or more sequencing reaction mixtures containing at most three different types of chain terminating nucleotides; and
   (b) evaluating the length of the oligonucleotide fragments formed in the one or more sequencing reaction mixtures.

2. The method of claim 1, wherein the sample is combined with a single sequencing reaction mixture containing two chain terminating nucleotides.

3. The method of claim 1, wherein the sample is combined with a single first sequencing reaction mixture containing only one chain terminating nucleotide, further comprising the step of combining the sample with a second sequencing reaction mixture containing a different chain terminating nucleotide after the lengths of the oligonucleotide fragments produced in the first sequencing reaction mixture are evaluated if identification of the allelic type of the locus cannot be made from the lengths of the oligonucleotide fragments produced in the first sequencing reaction.

4. The method of claim 1, wherein the sample is amplified prior to combining it with the sequencing reaction mixture to enrich the amount of the polymorphic genetic locus.

5. The method of claim 4, wherein the amplification is performed using polymerase chain reaction amplification.

6. A kit for identification of allelic type of a polymorphic genetic locus in a sample comprising, in packaged combination, (a) a sequencing primer having a sequence such that it hybridizes with genetic material in the sample near the polymorphic genetic locus to permit the generation of chain extension oligonucleotide products spanning the polymorphic genetic locus; and
   (b) four chain terminating nucleotides, wherein a first of said chain terminating nucleotides is provided in an amount which is five or more times greater than the amount of each one of the other three chain terminating nucleotides.

7. The kit of claim 6, wherein the first chain terminating nucleotide is dideoxyadenosine.

8. The kit of claim 6, wherein the first chain terminating nucleotide is dideoxycytosine.

9. The kit of claim 6, wherein the first chain terminating nucleotide is dideoxythymine.

10. The kit of claim 6, wherein the first chain terminating nucleotide is dideoxyguanosine.

11. A method for determining the allelic type of an HLA gene in a sample comprising the steps of:

(a) combining a first aliquot of the sample with a first sequencing reaction mixture containing a template-dependent nucleic acid polymerase, A, T, G and C nucleotide feedstocks, a first species of chain terminating nucleotide and a sequencing primer under conditions suitable for template dependant primer extension to form a plurality of oligonucleotide fragments of differing lengths, the lengths of said fragments indicating the positions of the species of base corresponding to the first species of chain terminating nucleotide in the extended primer;

(b) evaluating the length of the oligonucleotide fragments to determine the positions of the species of base corresponding to the first species of chain terminating nucleotide in the extended primer; and (c) comparing the positions of the species of base corresponding to the first species of chain terminating nucleotide in the extended primer to the positions found in known alleles of the HLA gene whereby the sample can either be assigned as being of a particular allelic type or is assigned as ambiguous for further evaluation.

12. The method of claim 11, wherein the sample is ambiguous after comparing the positions of the species of base corresponding to the first species of chain terminating nucleotide in the extended primer to the positions found in known alleles of the HLA gene, further comprising the steps of combining a second aliquot of the sample with a second sequencing reaction mixture containing a template-dependent nucleic acid polymerase, A, T, G and C nucleotide feedstocks, a second species of chain terminating nucleotide, different from said first species, and a sequencing primer under conditions suitable for template dependant primer extension to form a plurality of oligonucleotide fragments of differing lengths, the lengths of said fragments indicating the positions of the species of base corresponding to the second species of chain terminating nucleotide in the extended primer;

evaluating the length of the oligonucleotide fragments to determine the positions of the species of base corresponding to the second type of chain terminating nucleotide in the extended primer; and comparing the positions of the species of base corresponding to the first and second species of chain terminating nucleotide in the extended primer to the positions found in known alleles of the HLA gene whereby the sample can either be assigned as being of a particular allelic type or is assigned as ambiguous for further evaluation.

13. The method of claim 12, wherein the sample is ambiguous after comparing the positions of the species of base corresponding to the first and second species of chain terminating nucleotide in the extended primer to the positions found in known alleles of the HLA gene, further comprising the steps of combining a third aliquot of the sample with a third sequencing reaction mixture containing a template-dependent nucleic acid polymerase, A, T, G and C nucleotide feedstocks, a third species of chain terminating nucleotide, different from said first and second species, and a sequencing primer under conditions suitable for template dependant primer extension to form a plurality of oligonucleotide fragments of differing lengths, the lengths of said fragments indicating the positions of the species of base corresponding to the third species of chain terminating nucleotide in the extended primer;

evaluating the length of the oligonucleotide fragments to determine the positions of the species of base corresponding to the third species of chain terminating nucleotide in the extended primer; and comparing the positions of the species of base corresponding to the first, second and third species of chain terminating nucleotide in the extended primer to the positions found in known alleles of the HLA gene whereby the sample can either be assigned as being of a particular allelic type or is assigned as ambiguous for further evaluation.

14. The method of claim 13, wherein the sample is ambiguous after comparing the positions of the species of base corresponding to the first, second and third species of chain terminating nucleotide in the extended primer to the positions found in known alleles of the HLA gene, further comprising the steps of combining a fourth aliquot of the sample with a fourth sequencing reaction mixture containing a template-dependent nucleic acid polymerase, A, T, G and C nucleotide feedstocks, a fourth species of chain terminating nucleotide, different from said first, second and third species, and a sequencing primer under conditions suitable for template dependant primer extension to form a plurality of oligonucleotide fragments of differing lengths, the lengths of said fragments indicating the positions of the species of base corresponding to the fourth species of chain terminating nucleotide in the extended primer;

evaluating the length of the oligonucleotide fragments to determine the positions of the species of base corresponding to the fourth species of chain terminating nucleotide in the extended primer; and comparing the positions of the species of base corresponding to the first, second, third and fourth types of chain terminating nucleotide in the extended primer to the positions found in known alleles of the HLA gene whereby the sample can either be assigned as being of a particular allelic type or is assigned as ambiguous for further evaluation.

15. The method of claim 11, further comprising the step of determining the serological HLA subtype of the sample prior to performing combining the first aliquot with the first sequencing reaction mixture.

16. The method of claim 11, wherein the sample is amplified prior to combining it with the sequencing reaction mixture to enrich the amount of the polymorphic genetic locus.

17. The method of claim 16, wherein the amplification is performed using polymerase chain reaction amplification.

18. The method of claim 11, wherein the gene is an HLA Class I gene.

19. The method of claim 11, wherein the gene is an HLA Class II gene.

20. A method for determining the allelic type of a polymorphic gene in a sample comprising the steps of:
(a) combining a first aliquot of the sample with a first sequencing reaction mixture containing a template-dependent nucleic acid polymerase, A, T, G and C nucleotide feedstocks, a first species of chain terminating nucleotide and a sequencing primer under conditions suitable for template dependant primer extension to form a plurality of oligonucleotide fragments of differing lengths, the lengths of said fragments indicating the positions of the species of base corresponding to the first species of chain terminating nucleotide in the extended primer;
(b) evaluating the length of the oligonucleotide fragments to determine the positions of the species of base corresponding to the first species of chain terminating nucleotide in the extended primer; and
(c) comparing the positions of the species of base corresponding to the first species of chain terminating nucleotide in the extended primer to the positions found in known alleles of the gene whereby the sample can either be assigned as being of a particular allelic type or is assigned as ambiguous for further evaluation.

21. The method of claim 20, wherein the sample is ambiguous after comparing the positions of the species of base corresponding to the first species of chain terminating nucleotide in the extended primer to the positions found in known alleles of the gene, further comprising the steps of combining a second aliquot of the sample with a second sequencing reaction mixture containing a template-dependent nucleic acid polymerase, A, T, G and C nucleotide feedstocks, a second species of chain terminating nucleotide, different from said first species, and a sequencing primer under conditions suitable for template dependant primer extension to form a plurality of oligonucleotide fragments of differing lengths, the lengths of said fragments indicating the positions of the species of base corresponding to the second species of chain terminating nucleotide in the extended primer;
evaluating the length of the oligonucleotide fragments to determine the positions of the species of base corresponding to the second type of chain terminating nucleotide in the extended primer; and
comparing the positions of the species of base corresponding to the first and second species of chain terminating nucleotide in the extended primer to the positions found in known alleles of the gene whereby the sample can either be assigned as being of a particular allelic type or is assigned as ambiguous for further evaluation.

22. The method of claim 21, wherein the sample is ambiguous after comparing the positions of the species of base corresponding to the first and second species of chain terminating nucleotide in the extended primer to the positions found in known alleles of the gene, further comprising the steps of combining a third aliquot of the sample with a third sequencing reaction mixture containing a template-dependent nucleic acid polymerase, A, T, G and C nucleotide feedstocks, a third species of chain terminating nucleotide, different from said first and second species, and a sequencing primer under conditions suitable for template dependant primer extension to form a plurality of oligonucleotide fragments of differing lengths, the lengths of said fragments indicating the positions of the type of base corresponding to the third species of chain terminating nucleotide in the extended primer;
evaluating the length of the oligonucleotide fragments to determine the positions of the species of base corresponding to the third species of chain terminating nucleotide in the extended primer; and
comparing the positions of the species of base corresponding to the first, second and third species of chain terminating nucleotide in the extended primer to the positions found in known alleles of the gene whereby the sample can either be assigned as being of a particular allelic type or is assigned as ambiguous for further evaluation.

23. The method of claim 22, wherein the sample is ambiguous after comparing the positions of the species of base corresponding to the first, second and third species of chain terminating nucleotide in the extended primer to the positions found in known alleles of the gene, further comprising the steps of combining a fourth aliquot of the sample with a fourth sequencing reaction mixture containing a template-dependent nucleic acid polymerase, A, T, G and C nucleotide feedstocks, a fourth species of chain terminating nucleotide, different from said first, second and third species, and a sequencing primer under conditions suitable for template dependant primer extension to form a plurality of oligonucleotide fragments of differing lengths, the lengths of said fragments indicating the positions of the species of base corresponding to the fourth species of chain terminating nucleotide in the extended primer;
evaluating the length of the oligonucleotide fragments to determine the positions of the species of base corresponding to the fourth species of chain terminating nucleotide in the extended primer; and
comparing the positions of the species of base corresponding to the first, second, third and fourth species of chain terminating nucleotide in the extended primer to the positions found in known alleles of the gene whereby the sample can either be assigned as being of a particular allelic type or is assigned as ambiguous for further evaluation.

24. The method of claim 20, wherein the sample is amplified prior to combining it with the sequencing reaction mixture to enrich the amount of the polymorphic genetic locus.

25. The method of claim 20, wherein the amplification is performed using polymerase chain reaction amplification.

26. The method of claim 1, wherein the oligonucleotide fragments are evaluated by separation on a denaturing electrophoresis gel.

* * * * *